US012752113B2

(12) United States Patent
Smith

(10) Patent No.: US 12,752,113 B2
(45) Date of Patent: Oct. 6, 2026

(54) MAGNET REMOVAL AND REPLACEMENT APPARATUS AND METHODS FOR USE WITH COCHLEAR IMPLANTS

(71) Applicant: ADVANCED BIONICS AG, Staefa (CH)

(72) Inventor: James George elcoate Smith, Santa Clarita, CA (US)

(73) Assignee: Advanced Bionics AG, Staefa (CH)

( * ) Notice: Subject to any disclaimer, the term of this patent is extended or adjusted under 35 U.S.C. 154(b) by 1088 days.

(21) Appl. No.: 17/680,217

(22) Filed: Feb. 24, 2022

(65) Prior Publication Data

US 2022/0273948 A1 Sep. 1, 2022

Related U.S. Application Data

(62) Division of application No. 16/101,390, filed on Aug. 10, 2018, now abandoned.

(60) Provisional application No. 62/560,282, filed on Sep. 19, 2017, provisional application No. 62/543,798, filed on Aug. 10, 2017.

(51) Int. Cl.

| | |
|---|---|
| ***A61N 1/36*** | (2006.01) |
| ***A61N 1/05*** | (2006.01) |
| ***A61N 1/08*** | (2006.01) |
| ***A61N 1/375*** | (2006.01) |
| ***H01H 36/00*** | (2006.01) |

(52) U.S. Cl.

CPC ....... *A61N 1/36038* (2017.08); *A61N 1/0541* (2013.01); *A61N 1/08* (2013.01); *A61N 1/375* (2013.01); *H01H 36/0073* (2013.01)

(58) Field of Classification Search

CPC ........ A61N 1/08; A61N 1/0541; A61N 1/375; A61N 1/36038; A61N 36/0073

USPC .................................................. 128/897–899

See application file for complete search history.

(56) References Cited

U.S. PATENT DOCUMENTS

| | | | |
|---|---|---|---|
| 4,214,366 | A | 7/1980 | Laban |
| 4,352,960 | A | 10/1982 | Dormer et al. |
| 4,595,390 | A | 6/1986 | Hakim et al. |
| 4,606,329 | A | 8/1986 | Hough |
| 4,612,915 | A | 9/1986 | Hough et al. |
| 4,618,949 | A | 10/1986 | Lister |
| RE32,947 | E | 6/1989 | Dormer et al. |
| 5,290,281 | A | 3/1994 | Tschakaloff |
| 5,755,762 | A | 5/1998 | Bush |
| 5,824,022 | A | 10/1998 | Zilberman et al. |
| 5,945,762 | A | 8/1999 | Chen et al. |
| 6,032,677 | A | 3/2000 | Blechman et al. |
| 6,178,353 | B1 | 1/2001 | Griffith et al. |
| 6,190,305 | B1 | 2/2001 | Ball et al. |

(Continued)

FOREIGN PATENT DOCUMENTS

| | | | |
|---|---|---|---|
| CN | 212542072 | U | 2/2021 |
| DE | 202006017662 | U1 | 9/2007 |

(Continued)

OTHER PUBLICATIONS

U.S. Appl. No. 15/568,469, filed Oct. 21, 2017, 20180110985 A1.

(Continued)

*Primary Examiner* — Sunita Reddy

(74) *Attorney, Agent, or Firm* — Henricks Slavin LLP

(57) ABSTRACT

Apparatus and methods for installing a MR-compatible magnet apparatus into a cochlear implant.

13 Claims, 40 Drawing Sheets

(56) References Cited

U.S. PATENT DOCUMENTS

| | | | |
|---|---|---|---|
| 6,217,508 | B1 | 4/2001 | Ball et al. |
| 6,227,820 | B1 | 5/2001 | Jarvik |
| 6,292,678 | B1 | 9/2001 | Hall et al. |
| 6,348,070 | B1 | 2/2002 | Teissl et al. |
| 6,358,281 | B1 | 3/2002 | Berrang et al. |
| 6,461,288 | B1 | 10/2002 | Holcomb |
| 6,599,321 | B2 | 7/2003 | Hyde, Jr. |
| 6,838,963 | B2 | 1/2005 | Zimmerling |
| 7,091,806 | B2 | 8/2006 | Zimmerling et al. |
| 7,190,247 | B2 | 3/2007 | Zimmerling |
| 7,266,208 | B2 | 9/2007 | Charvin et al. |
| 7,566,296 | B2 | 7/2009 | Zimmerling et al. |
| 7,609,061 | B2 | 10/2009 | Hochmair |
| 7,642,887 | B2 | 1/2010 | Zimmerling |
| 7,680,525 | B1 | 3/2010 | Damadian |
| 7,729,774 | B1 | 6/2010 | Lynch et al. |
| 7,774,069 | B2 | 8/2010 | Olson et al. |
| 7,856,986 | B2 | 12/2010 | Darley |
| 7,881,800 | B2 | 2/2011 | Daly et al. |
| 7,976,453 | B2 | 7/2011 | Zimmerling et al. |
| 8,013,699 | B2 | 9/2011 | Zimmerling |
| 8,027,735 | B1 | 9/2011 | Tziviskos et al. |
| 8,118,725 | B2 | 2/2012 | Zimmerling et al. |
| 8,255,058 | B2 | 8/2012 | Gibson et al. |
| 8,340,774 | B2 | 12/2012 | Hochmair et al. |
| 8,634,909 | B2 | 1/2014 | Zimmerling et al. |
| 8,733,494 | B1 | 5/2014 | Leigh |
| 8,734,475 | B2 | 5/2014 | Ekvall et al. |
| 8,744,106 | B2 | 6/2014 | Ball |
| 8,758,394 | B2 | 6/2014 | Zimmerling et al. |
| 8,787,608 | B2 | 7/2014 | Van Himbeeck et al. |
| 8,790,409 | B2 | 7/2014 | Van den Heuvel et al. |
| 8,825,171 | B1 | 9/2014 | Thenuwara et al. |
| 8,891,795 | B2 | 11/2014 | Andersson |
| 8,897,475 | B2 | 11/2014 | Ball et al. |
| RE45,701 | E | 9/2015 | Zimmerling et al. |
| 9,126,010 | B2 | 9/2015 | Shah et al. |
| 9,162,054 | B2 | 10/2015 | Dalton |
| 9,227,064 | B2 | 1/2016 | Duftner |
| 9,295,425 | B2 | 3/2016 | Ball |
| 9,314,625 | B2 | 4/2016 | Kasic, II et al. |
| 9,352,149 | B2 | 5/2016 | Thenuwara et al. |
| RE46,057 | E | 7/2016 | Zimmerling et al. |
| 9,392,382 | B1 | 7/2016 | Nagl et al. |
| 9,420,388 | B2 | 8/2016 | Ball |
| 9,549,267 | B2 | 1/2017 | Nagl et al. |
| 9,615,181 | B2 | 4/2017 | Nagl et al. |
| 9,656,065 | B2 | 5/2017 | Tourrel et al. |
| 9,919,154 | B2 | 3/2018 | Lee |
| 9,931,501 | B2 | 4/2018 | Smyth |
| 10,300,276 | B2 | 5/2019 | Lee et al. |
| 10,463,849 | B2 | 11/2019 | Lee et al. |
| 10,532,209 | B2 | 1/2020 | Lee et al. |
| 10,646,712 | B2 | 5/2020 | Smith et al. |
| 10,646,718 | B2 | 5/2020 | Smith et al. |
| 10,806,936 | B2 | 10/2020 | Crawford et al. |
| 10,821,279 | B2 | 11/2020 | Lee et al. |
| 11,097,095 | B2 | 8/2021 | Smith et al. |
| 11,287,495 | B2 | 3/2022 | Smith et al. |
| 11,304,015 | B2 | 4/2022 | Haagerup |
| 11,364,384 | B2 | 6/2022 | Smith et al. |
| 11,471,679 | B2 | 10/2022 | Smith et al. |
| 11,476,025 | B2 | 10/2022 | Lee et al. |
| 11,638,823 | B2 | 5/2023 | Brehm et al. |
| 11,752,338 | B2 | 9/2023 | Smith et al. |
| 11,779,754 | B2 | 10/2023 | Smith et al. |
| 11,986,656 | B2 | 5/2024 | Lee et al. |
| 12,350,493 | B2 | 7/2025 | Smith et al. |
| 12,364,857 | B2 | 7/2025 | Crawford et al. |
| 12,440,668 | B2 | 10/2025 | Lee et al. |
| 12,544,579 | B2 | 2/2026 | Smith et al. |
| 2004/0012470 | A1 | 1/2004 | Zimmerling et al. |
| 2004/0059423 | A1 | 3/2004 | Barnes et al. |
| 2004/0063072 | A1 | 4/2004 | Honkura et al. |
| 2004/0210103 | A1 | 10/2004 | Westerkull |
| 2004/0260362 | A1 | 12/2004 | Darley |
| 2005/0001703 | A1 | 1/2005 | Zimmerling |
| 2005/0004629 | A1 | 1/2005 | Gibson et al. |
| 2005/0062567 | A1 | 3/2005 | Zimmerling et al. |
| 2006/0015155 | A1 | 1/2006 | Charvin et al. |
| 2006/0116743 | A1 | 6/2006 | Gibson et al. |
| 2006/0244560 | A1 | 11/2006 | Zimmerling et al. |
| 2007/0053536 | A1 | 3/2007 | Westerkull |
| 2007/0126540 | A1 | 6/2007 | Zimmerling |
| 2008/0097496 | A1 | 4/2008 | Chang et al. |
| 2008/0103350 | A1 | 5/2008 | Farone |
| 2008/0192968 | A1 | 8/2008 | Ho et al. |
| 2008/0195178 | A1 | 8/2008 | Kuzma |
| 2009/0048580 | A1 | 2/2009 | Gibson |
| 2009/0099403 | A1 | 4/2009 | Zimmerling et al. |
| 2009/0134721 | A1 | 5/2009 | Zimmerling |
| 2009/0248155 | A1 | 10/2009 | Parker |
| 2009/0287278 | A1 | 11/2009 | Charvin |
| 2010/0004716 | A1 | 1/2010 | Zimmerling et al. |
| 2010/0036458 | A1 | 2/2010 | Duftner et al. |
| 2010/0046778 | A1 | 2/2010 | Crawford et al. |
| 2010/0046779 | A1 | 2/2010 | Crawford et al. |
| 2011/0009925 | A1 | 1/2011 | Leigh et al. |
| 2011/0022120 | A1 | 1/2011 | Ball et al. |
| 2011/0068885 | A1 | 3/2011 | Fullerton et al. |
| 2011/0178364 | A1* | 7/2011 | Ball .......................... A61F 2/18 600/25 |
| 2011/0218605 | A1 | 9/2011 | Cryer |
| 2011/0224756 | A1* | 9/2011 | Zimmerling ............. A61N 1/37 607/57 |
| 2011/0255731 | A1 | 10/2011 | Ball |
| 2011/0264172 | A1 | 10/2011 | Zimmerling et al. |
| 2012/0296155 | A1 | 11/2012 | Ball |
| 2013/0079749 | A1 | 3/2013 | Overstreet et al. |
| 2013/0150657 | A1 | 6/2013 | Leigh et al. |
| 2013/0184804 | A1 | 7/2013 | Dalton |
| 2013/0281764 | A1 | 10/2013 | Bjorn et al. |
| 2013/0343588 | A1 | 12/2013 | Karunasiri |
| 2014/0005750 | A1 | 1/2014 | Garnham et al. |
| 2014/0012069 | A1 | 1/2014 | Ball |
| 2014/0012070 | A1 | 1/2014 | Nagl et al. |
| 2014/0012071 | A1 | 1/2014 | Nagl et al. |
| 2014/0012349 | A1 | 1/2014 | Zimmerling |
| 2014/0121449 | A1 | 5/2014 | Kasic et al. |
| 2014/0121586 | A1 | 5/2014 | Bertrand et al. |
| 2014/0163692 | A1 | 6/2014 | Van den Heuvel et al. |
| 2014/0336447 | A1 | 11/2014 | Bjorn et al. |
| 2014/0343626 | A1 | 11/2014 | Thenuwara et al. |
| 2015/0025613 | A1 | 1/2015 | Nyberg, II et al. |
| 2015/0073205 | A1 | 3/2015 | Ball et al. |
| 2015/0087892 | A1 | 3/2015 | Tourrel et al. |
| 2015/0094521 | A1 | 4/2015 | Neuman et al. |
| 2015/0100109 | A1 | 4/2015 | Feldman et al. |
| 2015/0112407 | A1 | 4/2015 | Hartley et al. |
| 2015/0265842 | A1 | 9/2015 | Ridler |
| 2015/0320523 | A1 | 11/2015 | Way et al. |
| 2015/0367126 | A1 | 12/2015 | Smyth |
| 2015/0374989 | A1 | 12/2015 | Hazard et al. |
| 2015/0382114 | A1 | 12/2015 | Andersson et al. |
| 2016/0008596 | A1 | 1/2016 | Gibson et al. |
| 2016/0023006 | A1 | 1/2016 | Ridler et al. |
| 2016/0037273 | A1 | 2/2016 | Gustafsson |
| 2016/0144170 | A1 | 5/2016 | Gibson et al. |
| 2016/0205484 | A1 | 7/2016 | Nagl et al. |
| 2016/0213936 | A1 | 7/2016 | Heerlein et al. |
| 2016/0310737 | A1 | 10/2016 | Tourrel et al. |
| 2016/0361537 | A1 | 12/2016 | Leigh et al. |
| 2016/0381473 | A1 | 12/2016 | Gustafsson |
| 2016/0381474 | A1 | 12/2016 | Gustafsson et al. |
| 2017/0050027 | A1 | 2/2017 | Andersson et al. |
| 2017/0078808 | A1* | 3/2017 | Kennes ................ H04R 25/606 |
| 2017/0156010 | A1 | 6/2017 | Verma et al. |
| 2017/0173334 | A1 | 6/2017 | Zimmerling |
| 2017/0239476 | A1 | 8/2017 | Lee |
| 2017/0251312 | A1 | 8/2017 | Crawford et al. |
| 2017/0347208 | A1 | 11/2017 | Jurkiewicz |
| 2018/0028818 | A1 | 2/2018 | Anderson et al. |
| 2018/0056084 | A1 | 3/2018 | Alam |
| 2018/0110985 | A1 | 4/2018 | Walter |

(56) References Cited

U.S. PATENT DOCUMENTS

| | | | |
|---|---|---|---|
| 2018/0110986 | A1 | 4/2018 | Lee |
| 2018/0133486 | A1 | 5/2018 | Smith |
| 2018/0146308 | A1 | 5/2018 | Leigh et al. |
| 2018/0160241 | A1 | 6/2018 | Gustafsson et al. |
| 2018/0160242 | A1 | 6/2018 | Sriskandarajah |
| 2018/0185634 | A1 | 7/2018 | Smyth |
| 2018/0249262 | A1 | 8/2018 | Santek |
| 2018/0270591 | A1 | 9/2018 | Kennes |
| 2018/0296826 | A1 | 10/2018 | Lee et al. |
| 2018/0303602 | A1 | 10/2018 | Leigh |
| 2018/0304078 | A1 | 10/2018 | Crawford et al. |
| 2018/0369586 | A1 | 12/2018 | Lee et al. |
| 2019/0015662 | A1 | 1/2019 | Raje et al. |
| 2019/0046797 | A1 | 2/2019 | Calixto et al. |
| 2019/0053908 | A1 | 2/2019 | Cook et al. |
| 2019/0076649 | A1 | 3/2019 | Lee et al. |
| 2019/0255316 | A1 | 8/2019 | Lee et al. |
| 2019/0298417 | A1 | 10/2019 | Barrett et al. |
| 2020/0114151 | A1 | 4/2020 | Smith et al. |
| 2020/0230422 | A1 | 7/2020 | Gibson et al. |
| 2020/0238088 | A1 | 7/2020 | Smith et al. |
| 2020/0330777 | A1 | 10/2020 | Smith et al. |
| 2020/0391023 | A1 | 12/2020 | Lee et al. |
| 2021/0046311 | A1 | 2/2021 | Brehm et al. |
| 2021/0106815 | A1 | 4/2021 | Smith et al. |
| 2021/0156934 | A1 | 5/2021 | Smith et al. |
| 2021/0299456 | A1 | 9/2021 | Smith et al. |
| 2021/0316136 | A1 | 10/2021 | Smith et al. |
| 2021/0339021 | A1 | 11/2021 | Brehm et al. |
| 2022/0280793 | A1 | 9/2022 | Smith et al. |
| 2023/0032218 | A1 | 2/2023 | Smith et al. |
| 2023/0061335 | A1 | 3/2023 | Lee et al. |
| 2023/0115968 | A1 | 4/2023 | Lee et al. |
| 2024/0342473 | A1 | 10/2024 | Smith et al. |
| 2025/0001175 | A1 | 1/2025 | Lee et al. |
| 2025/0001186 | A1 | 1/2025 | Lee et al. |
| 2025/0050102 | A1 | 2/2025 | Smith et al. |
| 2026/0054068 | A1 | 2/2026 | Smith et al. |
| 2026/0077195 | A1 | 3/2026 | Alanis et al. |

FOREIGN PATENT DOCUMENTS

| | | | |
|---|---|---|---|
| EP | 0241307 | A2 | 10/1987 |
| EP | 2117489 | B1 | 5/2010 |
| EP | 2853287 | A1 | 4/2015 |
| EP | 2560730 | B1 | 11/2016 |
| EP | 3138605 | A1 | 3/2017 |
| EP | 2098198 | B1 | 9/2017 |
| EP | 3964259 | A1 | 3/2022 |
| RU | 2727227 | C1 | 7/2020 |
| WO | WO9858990 | A1 | 12/1998 |
| WO | WO03081976 | A2 | 10/2003 |
| WO | WO03092326 | A1 | 11/2003 |
| WO | WO2004004416 | A1 | 1/2004 |
| WO | WO2004014269 | A1 | 2/2004 |
| WO | WO2004014270 | A1 | 2/2004 |
| WO | WO2007024657 | A2 | 3/2007 |
| WO | WO2009124045 | A1 | 10/2009 |
| WO | WO2009124174 | A2 | 10/2009 |
| WO | WO2009149069 | A2 | 12/2009 |
| WO | WO2010000027 | A1 | 1/2010 |
| WO | WO2010083554 | A1 | 7/2010 |
| WO | WO2011011409 | A1 | 1/2011 |
| WO | WO2011109486 | A2 | 9/2011 |
| WO | WO2011133747 | A1 | 10/2011 |
| WO | WO2012010195 | A1 | 1/2012 |
| WO | WO2013043176 | A1 | 3/2013 |
| WO | WO2013063355 | A1 | 5/2013 |
| WO | WO2014011441 | A1 | 1/2014 |
| WO | WO2014011582 | A2 | 1/2014 |
| WO | WO2014046662 | A1 | 3/2014 |
| WO | WO2014164023 | A1 | 10/2014 |
| WO | WO2015065442 | A1 | 5/2015 |
| WO | WO2016016821 | A1 | 2/2016 |
| WO | WO2016190886 | A1 | 12/2016 |
| WO | WO2016191429 | A1 | 12/2016 |
| WO | WO2016207856 | A1 | 12/2016 |
| WO | WO2017027045 | A1 | 2/2017 |
| WO | WO2017027046 | A1 | 2/2017 |
| WO | WO2017029615 | A1 | 2/2017 |
| WO | WO2017034530 | A1 | 3/2017 |
| WO | WO2017046650 | A1 | 3/2017 |
| WO | WO2017087004 | A1 | 5/2017 |
| WO | WO2017105510 | A1 | 6/2017 |
| WO | WO2017105511 | A1 | 6/2017 |
| WO | WO2017105604 | A1 | 6/2017 |
| WO | WO2017172566 | A1 | 10/2017 |
| WO | WO2018190813 | A1 | 10/2018 |
| WO | WO2018191314 | A1 | 10/2018 |
| WO | WO2018199936 | A1 | 11/2018 |
| WO | WO2018200347 | A1 | 11/2018 |
| WO | WO2018217187 | A1 | 11/2018 |
| WO | WO2019027745 | A1 | 2/2019 |
| WO | WO2019083540 | A1 | 5/2019 |
| WO | WO2019160555 | A1 | 8/2019 |
| WO | WO2020092185 | A1 | 5/2020 |
| WO | WO2021201845 | A1 | 10/2021 |
| WO | WO2023063934 | A1 | 4/2023 |
| WO | WO2023063983 | A1 | 4/2023 |
| WO | WO2023064308 | A1 | 4/2023 |
| WO | WO2023113790 | A1 | 6/2023 |
| WO | WO2024043896 | A1 | 2/2024 |
| WO | WO2024080978 | A1 | 4/2024 |

OTHER PUBLICATIONS

U.S. Appl. No. 15/770,207, filed Apr. 22, 2018, U.S. Pat. No. 10,806,936.
U.S. Appl. No. 17/073,322, filed Oct. 17, 2020, 20210170167 A1.
U.S. Appl. No. 16/060,383, filed Jun. 7, 2018, U.S. Pat. No. 10,532,209.
U.S. Appl. No. 15/591,054, filed May 9, 2017, U.S. Pat. No. 9,919,154.
U.S. Appl. No. 16/009,600, filed Jun. 15, 2018, U.S. Pat. No. 10,821,279.
U.S. Appl. No. 16/403,582, filed May 5, 2019, U.S. Pat. No. 10,463,849.
U.S. Appl. No. 17/008,291, filed Aug. 31, 2020, U.S. Pat. No. 11,476,025.
U.S. Appl. No. 17/965,580, filed Oct. 13, 2022.
U.S. Appl. No. 16/610,502, filed Nov. 2, 2019, U.S. Pat. No. 11,287,495.
U.S. Appl. No. 15/568,470, filed Oct. 21, 2017, U.S. Pat. No. 10,300,276.
U.S. Appl. No. 16/101,390, filed Aug. 10, 2018, 20190046797 A1.
U.S. Appl. No. 17/680,217, filed Feb. 24, 2022, 20220273948 A1.
U.S. Appl. No. 15/703,808, filed Sep. 13, 2017, U.S. Pat. No. 10,646,712.
U.S. Appl. No. 15/805,025, filed Nov. 6, 2017, U.S. Pat. No. 10,646,718.
U.S. Appl. No. 16/852,457, filed Apr. 18, 2020, 20200238088 A1.
U.S. Appl. No. 16/499,311, filed Sep. 29, 2019, U.S. Pat. No. 11,097,095.
U.S. Appl. No. 17/355,225, filed Jun. 23, 2021, 20210316136 A1.
U.S. Appl. No. 16/603,868, filed Oct. 9, 2019, U.S. Pat. No. 11,364,384.
U.S. Appl. No. 17/750,352, filed May 22, 2022, 20220280793 A1.
U.S. Appl. No. 16/754,126, filed Apr. 6, 2020, U.S. Pat. No. 11,471,679.
U.S. Appl. No. 17/964,321, filed Oct. 12, 2022.
U.S. Appl. No. 17/335,161, filed Jun. 1, 2021, 20210339021 A1.
U.S. Appl. No. 17/346,343, filed Jun. 14, 2021, 20210299456 A1.
U.S. Appl. No. 17/499,813, filed Oct. 12, 2021.
U.S. Appl. No. 17/750,352, filed May 22, 2022.
U.S. Appl. No. 16/754,126, filed Apr. 6, 2020, 20200330777 A1.
U.S. Appl. No. 17/008,291, filed Aug. 31, 2020, 20200391023 A1.
U.S. Appl. No. 17/680,217, filed Feb. 24, 2022.
U.S. Appl. No. 16/603,868, filed Oct. 9, 2019, 20200114151 A1.

(56) References Cited

OTHER PUBLICATIONS

Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.

Teissl et al., "Magnetic Resonance Imaging and Cochlear Implants: Compatibility and Safety Aspects," Journal of Magnetic Resonance Imaging, Society For Magnetic Resonance Imaging, vol. 9, No. 1, pp. 26-38, Jan. 1, 1999.

U.S. Appl. No. 17/750,352, filed May 2022, 20220280793 A1.

U.S. Appl. No. 17/073,322, filed Oct. 17, 2020, U.S. Pat. No. 12,364,857.

U.S. Appl. No. 17/965,580, filed Oct. 13, 2022, U.S. Pat. No. 11,986,656.

U.S. Appl. No. 17/355,225, filed Jun. 23, 2021, U.S. Pat. No. 11,779,754.

U.S. Appl. No. 17/750,352, filed May 22, 2022, U.S. Pat. No. 11,752,338.

U.S. Appl. No. 17/964,321, filed Oct. 12, 2022, U.S. Pat. No. 12,350,493.

U.S. Appl. No. 17/335,161, filed Jun. 1, 2021, U.S. Pat. No. 11,638,823.

U.S. Appl. No. 18/691,947, filed Mar. 14, 2024, 20240342473 A1.

U.S. Appl. No. 18/718,442, filed Jun. 10, 2024, 20250050102 A1.

U.S. Appl. No. 18/701,147, filed Apr. 12, 2024, 20250001175 A1.

U.S. Appl. No. 19/105,388, filed Feb. 21, 2025.

U.S. Appl. No. 17/499,813, filed Oct. 12, 2021, U.S. Pat. No. 12,440,668.

U.S. Appl. No. 18/701,199, filed Apr. 12, 2024, 20250001186 A1.

U.S. Appl. No. 19/117,039, filed Mar. 29, 2025.

U.S. Appl. No. 18/885,649, filed Sep. 14, 2024.

U.S. Appl. No. 17/964,321, filed Oct. 12, 2022, 20230032218 A1.

U.S. Appl. No. 18/691,947, filed Mar. 14, 2024.

U.S. Appl. No. 18/701,147, filed Apr. 12, 2024.

U.S. Appl. No. 17/499,813, filed Oct. 12, 2021, 20230115968 A1.

U.S. Appl. No. 18/701,199, filed Apr. 12, 2024.

* cited by examiner

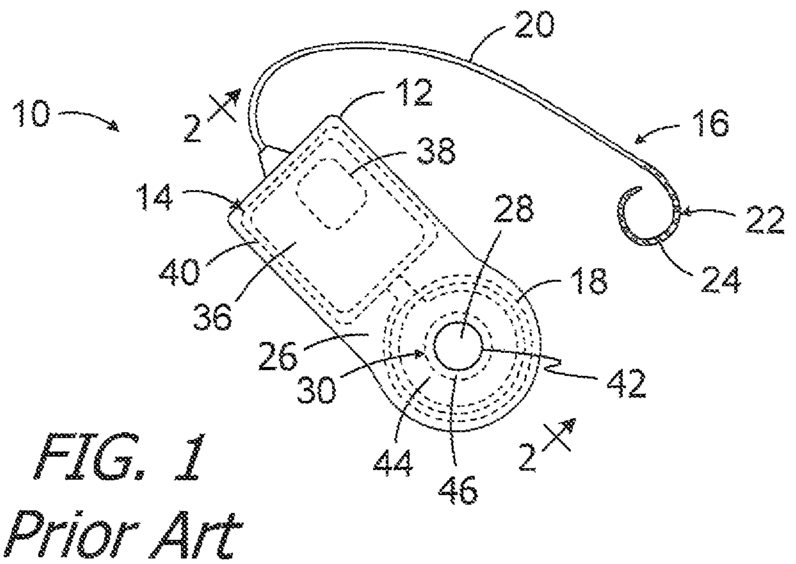
FIG. 1
Prior Art
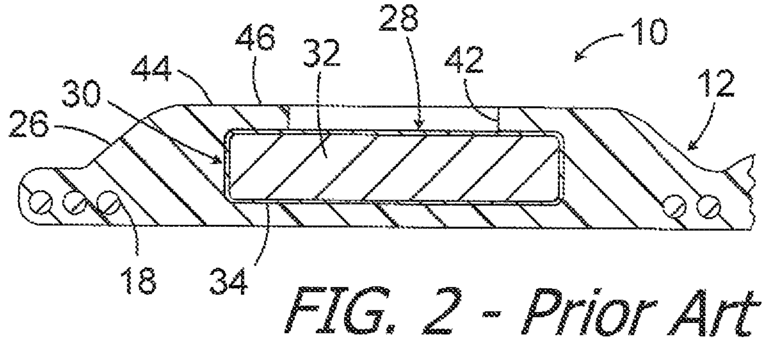
FIG. 2 - Prior Art
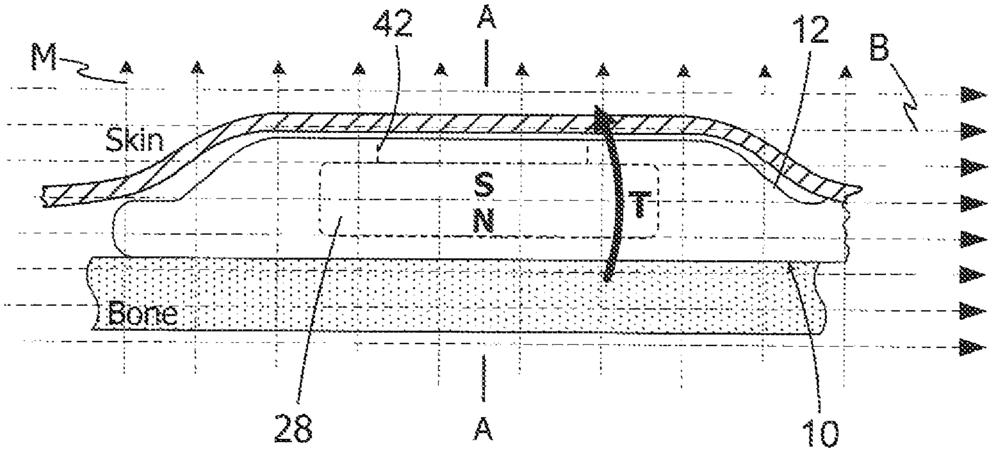
FIG. 3 - Prior Art

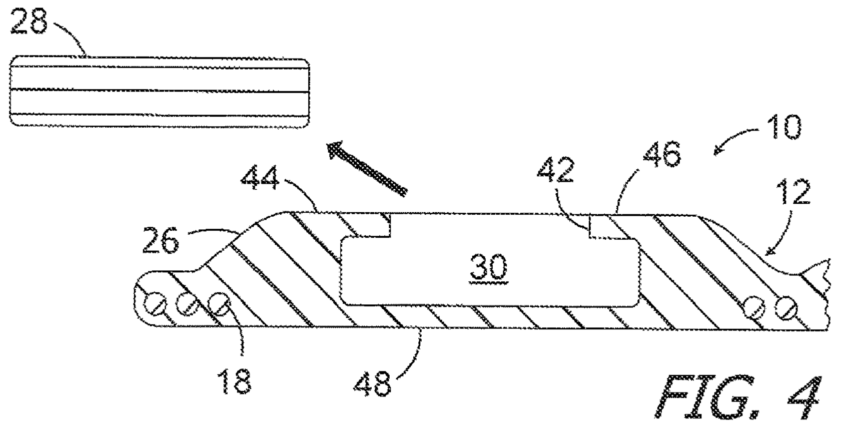
FIG. 4
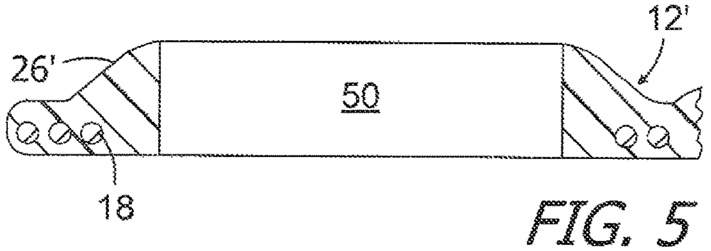
FIG. 5
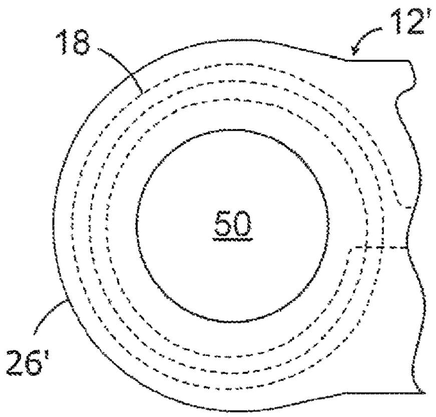
FIG. 6
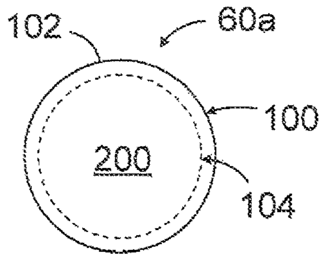
FIG. 7A
FIG. 7B
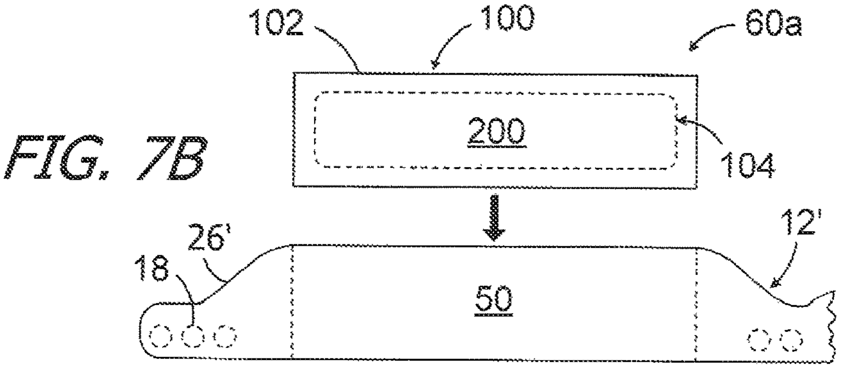

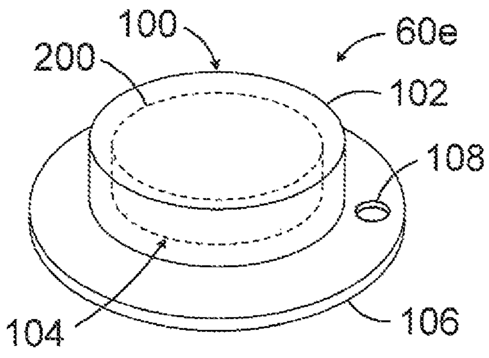
FIG. 17
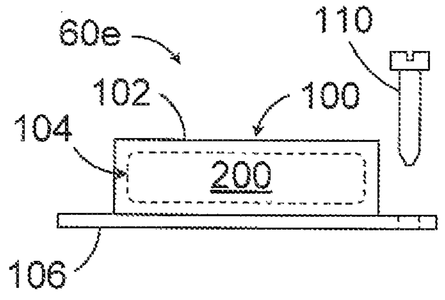
FIG. 18
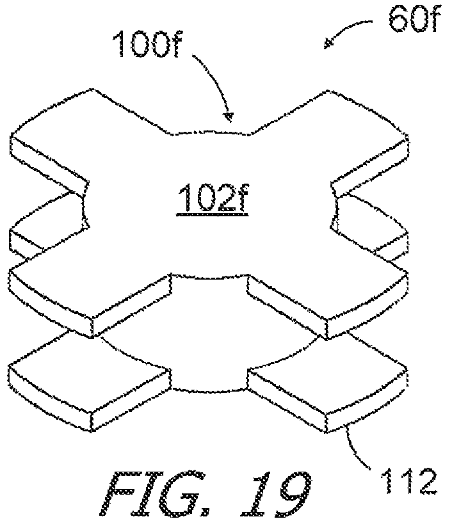
FIG. 19
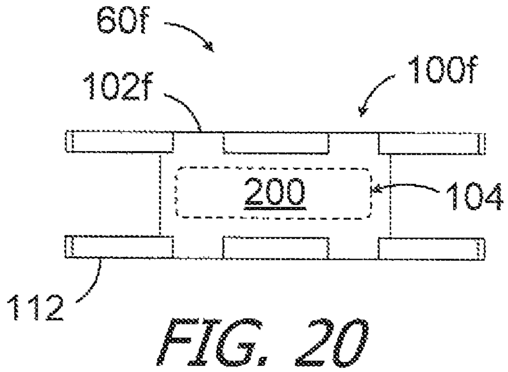
FIG. 20
FIG. 21
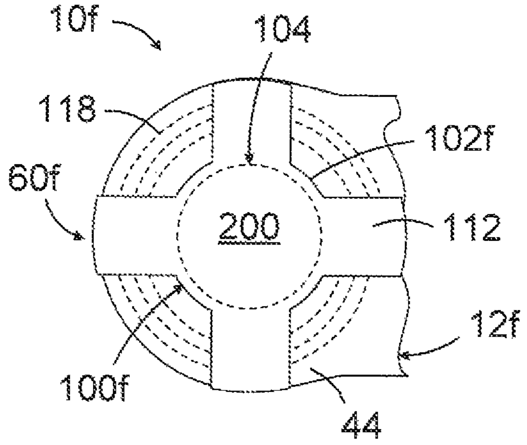

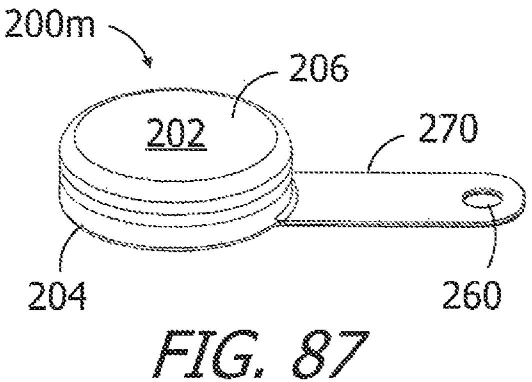
FIG. 87
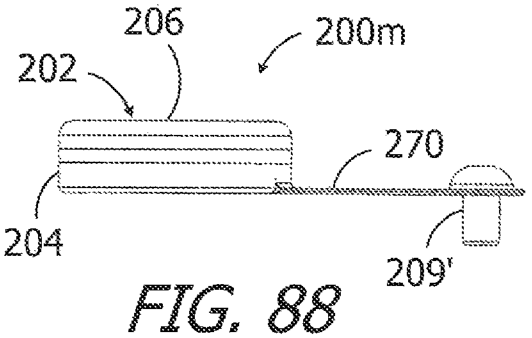
FIG. 88
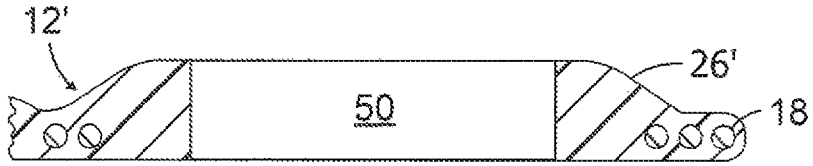
FIG. 89
FIG. 90
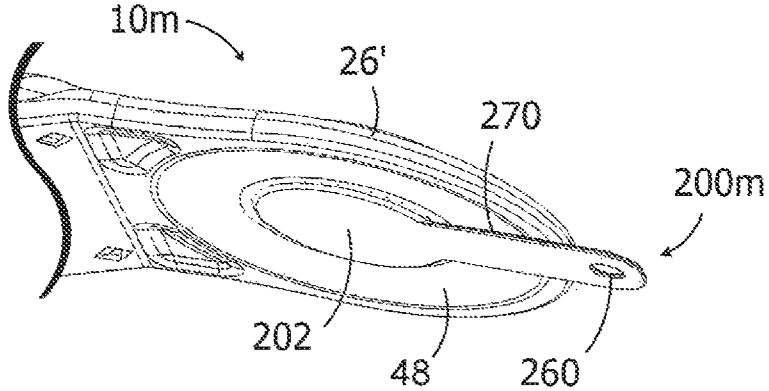
FIG. 91
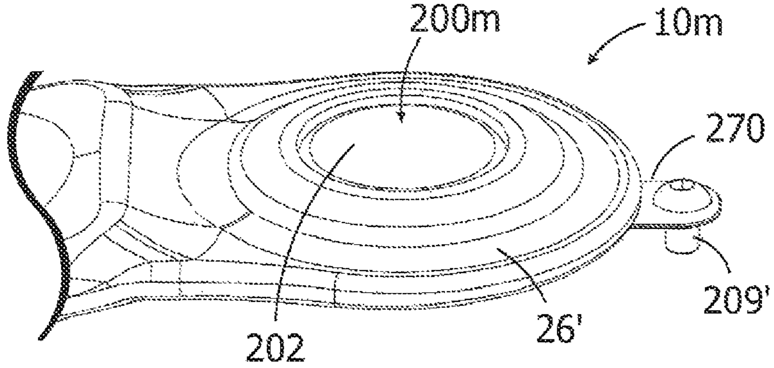

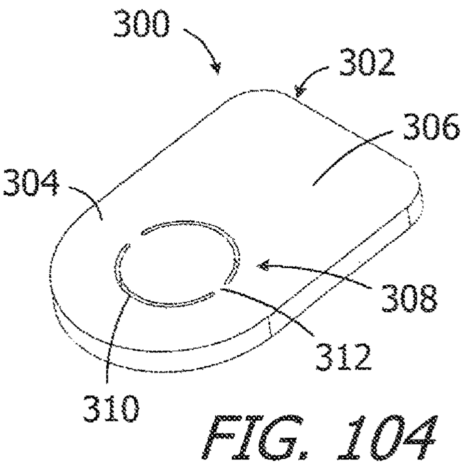
FIG. 104
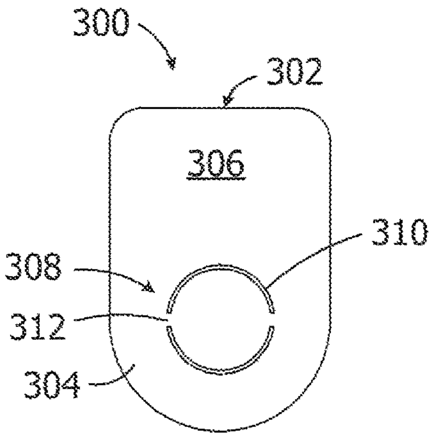
FIG. 105
FIG. 106
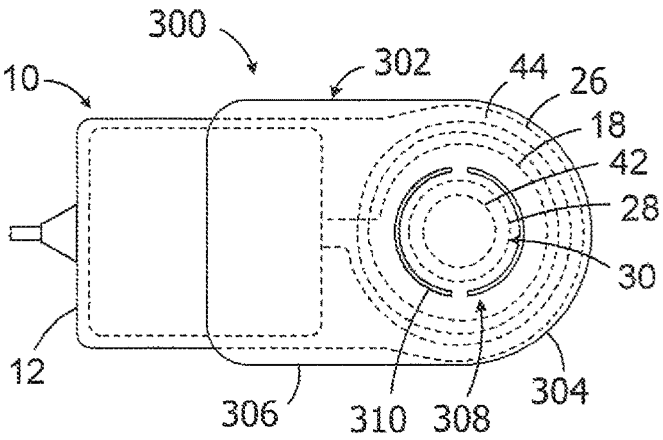
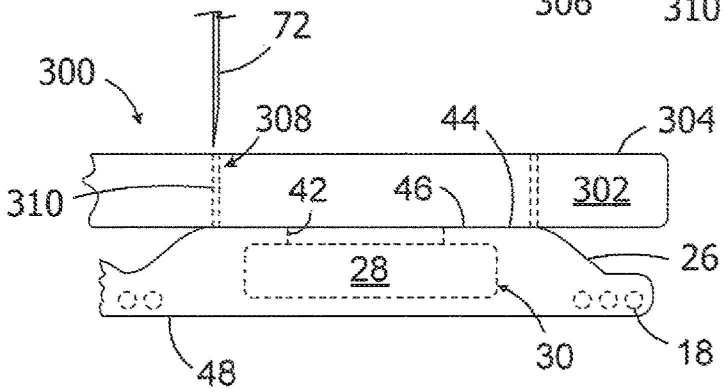
FIG. 107
FIG. 108
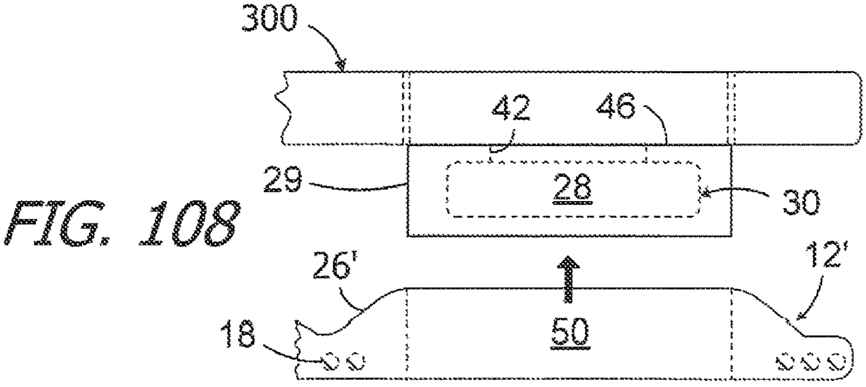

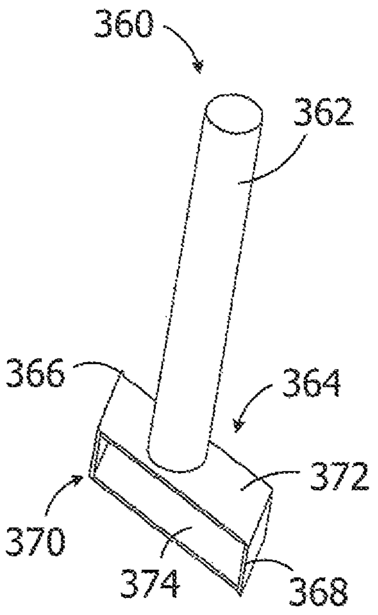
FIG. 120
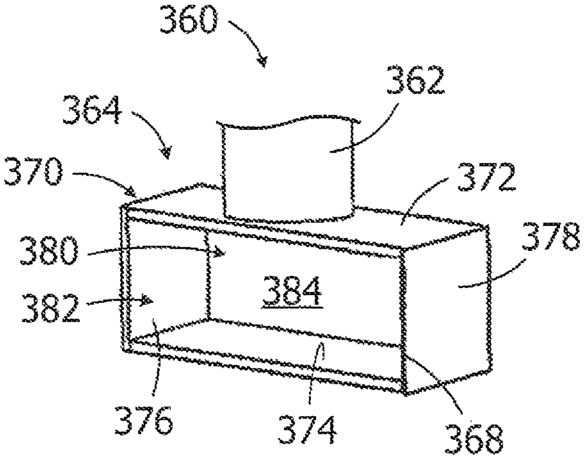
FIG. 121
FIG. 122
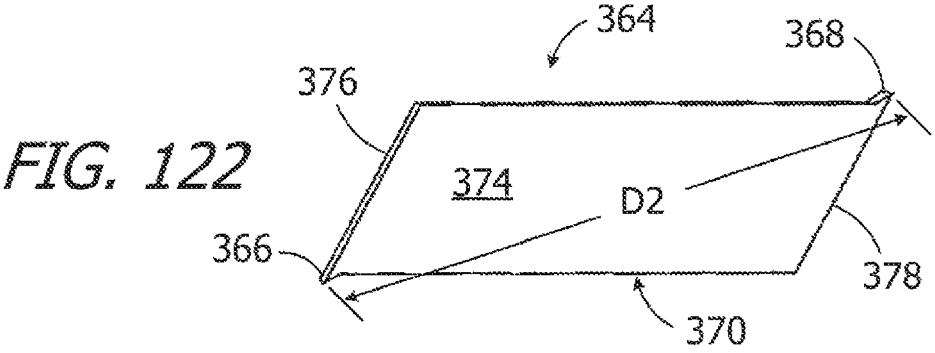
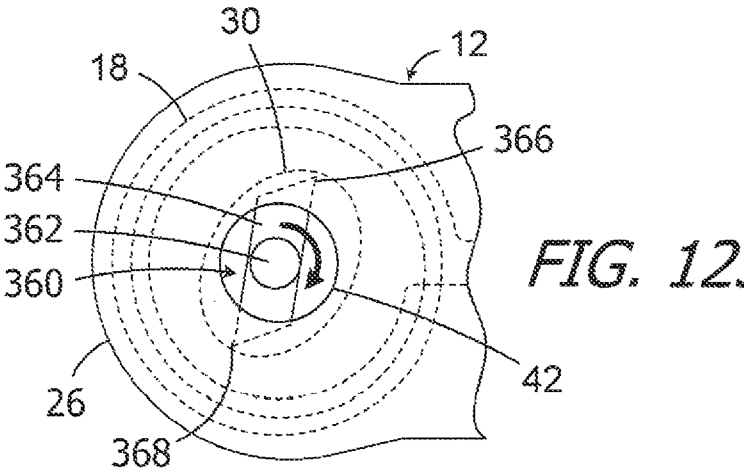
FIG. 123

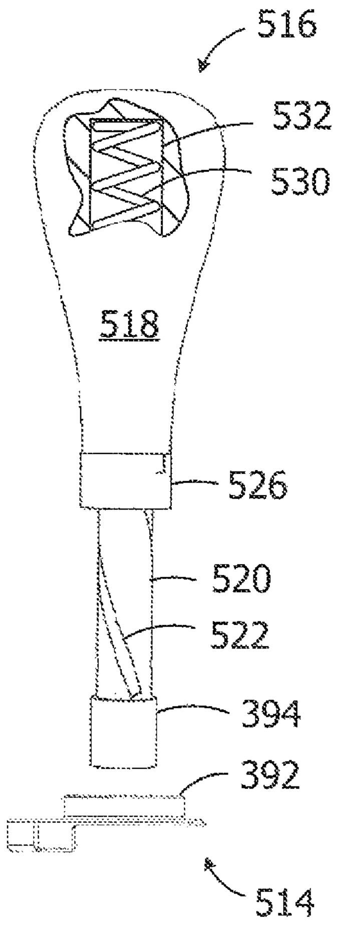
FIG. 149
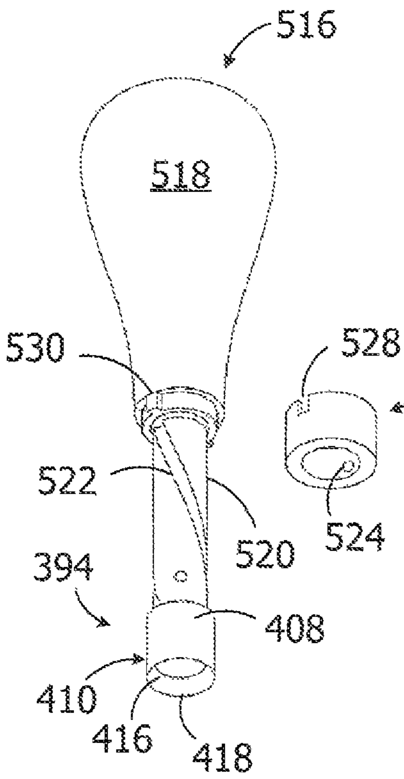
FIG. 150
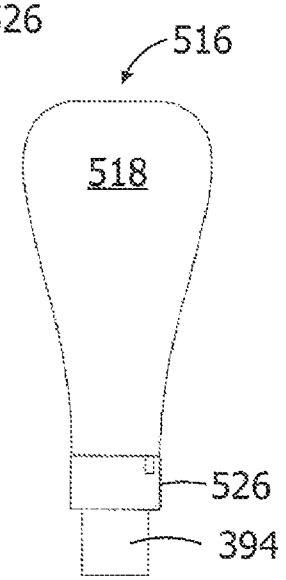
FIG. 151
FIG. 152
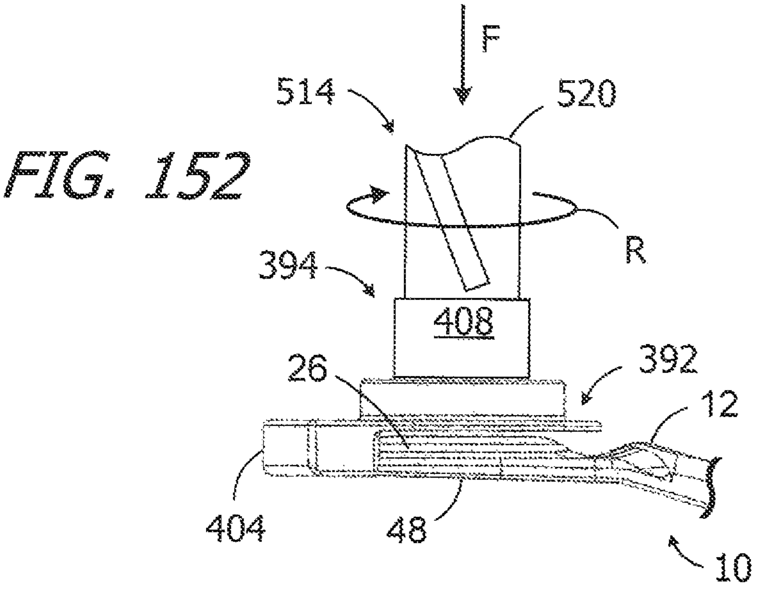

MAGNET REMOVAL AND REPLACEMENT APPARATUS AND METHODS FOR USE WITH COCHLEAR IMPLANTS

CROSS-REFERENCE TO RELATED APPLICATIONS

This application is a divisional of U.S. application Ser. No. 16/101,390, filed August 102018, which claims the benefit of U.S. Provisional Application No. 62/543,798, filed Aug. 10, 2017, which is incorporated herein by reference. U.S. application Ser. No. 16/101,390 also claims the benefit of U.S. Provisional Application No. 62/560,282, filed Sep. 19, 2017, which is incorporated herein by reference.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing.

One example of a conventional cochlear implant (or "implantable cochlear stimulator") is the cochlear implant 10 illustrated in FIGS. 1 and 2. The cochlear implant 10 includes a flexible housing 12 formed from a silicone elastomer or other suitable material, a processor assembly 14, a cochlear lead 16, and an antenna 18 that may be used to receive data and power by way of an external antenna that is associated with, for example, a sound processor unit. The cochlear lead 16 may include a flexible body 20, an electrode array 22 at one end of the flexible body, and a plurality of wires (not shown) that extend through the flexible body from the electrodes 24 (e.g., platinum electrodes) in the array 22 to the other end of the flexible body. The antenna 18 is located within an antenna portion 26 of the housing 12. A cylindrical magnet 28, with north and south magnetic dipoles that are aligned in the axial direction, is located within a pocket 30 in the housing antenna portion 26. The magnet 28 is used to maintain the position of a headpiece transmitter over the antenna 18, and includes magnetic material 32 and a hermetically sealed case 34. The exemplary processor assembly 14, which is connected to the electrode array 22 and antenna 18, includes a printed circuit board 36 with a stimulation processor 38 that is located within a hermetically sealed case 40. The stimulation processor 38 converts the stimulation data into stimulation signals that stimulate the electrodes 24 of the electrode array 22.

There are some instances where it is necessary to remove the magnet from a conventional cochlear implant, and then reinsert the magnet, in situ, i.e., with the cochlear implant accessed by way of an incision in the skin. To that end, the magnet 28 can be inserted into, and removed from, the housing pocket 30 by way of a magnet aperture 42 that extends through the housing top wall 44 (which defines the top surface of the housing). The magnet 28 is larger than the magnet aperture 42, i.e., the outer perimeter of the magnet is greater than the perimeter of the magnet aperture. The portion of the top wall 44 between the aperture 42 and the outer edge of the magnet forms a retainer 46 that, absent deformation of the aperture and retainer, prevents the magnet from coming out of the housing 12. During installation and removal, the aperture 42 and retainer 46 are stretched or otherwise deformed so that the magnet 28 can pass through the aperture.

The present inventors have determined that conventional cochlear implants are susceptible to improvement. For example, removal and reinsertion of the implant magnet by way of the aperture may be required because some conventional cochlear implants are not compatible with magnetic resonance imaging ("MRI") systems. As illustrated in FIG. 3, the implant magnet 28 produces a magnetic field M in a direction that is perpendicular to the patient's skin and parallel to the axis A. This magnetic field direction is not aligned with, and may be perpendicular to (as shown), the direction of the MRI magnetic field B. The misalignment of the interacting magnetic fields M and B is problematic for a number of reasons. The dominant MRI magnetic field B (typically 1.5 Tesla or more) may generate a significant amount of torque T on the magnet 28. The torque T may be sufficient to deform the retainer 46, dislodge the magnet 28 from the pocket 30, and cause reorientation of the magnet. Reorientation of the magnet 28 can place significant stress on the dermis (or "skin"), which cause significant pain. In some instances, the magnet 28 may rotate 180 degrees, thereby reversing the N-S orientation of the magnet.

As alluded to above, magnet rotation may be avoided by surgically removing the positioning magnet prior to the MRI procedure and then reinserting the magnet after the procedure. A wide variety of removable positioning magnets, and removable positioning magnet systems, have been employed in conventional cochlear implants. The manner in which the magnet is removed from the magnet pocket will depend upon the type of magnet or magnet system. For example, some positioning magnets simply include magnetic material that is hermetically sealed within a biocompatible case (such as a titanium case) or magnetic material that is sealed within a biocompatible coating, and may be removed from the magnet pocket in the manner described above. Positioning magnet 28 is one example of a positioning magnet that includes magnet material within a titanium case.

Other positioning magnets are part of systems that include structures which are capable of preventing magnet reorientation in relatively low strength MRI magnetic fields, while permitting removal if necessary. For example, U.S. Pat. No. 9,352,149 discloses a system that includes a retainer which surrounds the magnet pocket and is embedded within the implant housing and a magnet case that may be secured to the retainer through the use of threads (or other mechanical interconnects) on the retainer and magnet case. U.S. Pat. Pub. No. 2016/0144170 discloses an embedded retainer (referred to as a "mounting") and a magnet that include mechanical interconnects that allow the magnet to be rotated into engagement with the retainer, as well as other releasable mechanical connectors that secure the magnet within the magnet pocket and allow removal of the magnet as necessary. Other systems, such as those disclosed in U.S. Pat. No. 8,340,774, include a retainer in which the magnet is located. The retainer (in which the magnet is located) may be inserted into an opening in the elastomeric housing of the associated cochlear implant, and also removed from the housing if necessary. References herein to "positioning magnets" include all such removable positioning magnets as well as the removable magnetic portions of all such systems.

The present inventors have determined that removal and reinsertion can be problematic because some patients will have many MRI procedures during their lifetimes, and repeated surgeries can result in skin necrosis at the implant site. More recently, implant magnet apparatus that are compatible with MRI systems have been developed. Examples of MRI-compatible magnet apparatus are disclosed in PCT Pat. Pub. No. 2016/190886 and PCT Pat. Pub. No. 2017/105604, which are incorporated herein by reference in their entireties. The present inventors have determined that although MRI-compatible magnet apparatus are an advance in the art, such magnet apparatus will not physically fit into the magnet pocket of many older cochlear implants that are already implanted in patients, thereby preventing the replacement of a conventional magnet with a MRI-compatible magnet apparatus.

Other proposed techniques for avoiding the magnet rotation associated with MRI procedures involve using one or more bone screws to anchor the magnet to the skull. The present inventors have determined that these conventional techniques are susceptible to improvement. For example, the torque on the magnet generated by the dominant MRI magnetic field B can cause trauma to the bone tissue and discomfort to the patient. The torque may also break or demagnetize the magnet. Moreover, bone screws tend to become permanently integrated into the bone, which can be problematic should removal of the cochlear implant become necessary. Here, the bone screws must be drilled out of the bone and, when the removed implant (or a replacement implant) is subsequently implanted, the new bone screws must be offset from the prior bone screw locations. As a result, the cochlear implant, including the lead that carries the electrode array, must be repositioned.

Accordingly, the present inventors have determined that it would be desirable to provide apparatus and methods which facilitate the replacement of a conventional implant magnet with an MRI-compatible magnet apparatus, even in those instances where the MRI-compatible magnet apparatus will not physically fit into the magnet pocket of the associated cochlear implant. The present inventors have also determined it would be desirable to employ bone screws (or other anchors) in such a manner that the presence of a dominant MRI magnetic field will not result in trauma to the bone or damage to the magnet, and that will facilitate replacement of the cochlear implant without removal of an associated MRI-compatible magnet apparatus.

SUMMARY

A method, for use with a cochlear implant, includes the steps of removing a portion of the resilient material from the cochlear implant housing and replacing the magnet with an MRI-compatible magnet apparatus that is larger than the magnet within the antenna pocket, or with a magnet that is larger than the magnet within the antenna pocket.

A magnet apparatus insert, for use with a cochlear implant, includes a housing portion replacement having a magnet housing formed from a resilient elastomer and configured to fit within an aperture in the antenna portion of the cochlear implant housing, and an MRI-compatible magnet apparatus embedded at least partially within the magnet housing.

A cochlear implant with a cochlear implant housing, formed from a resilient elastomer, including an antenna portion and an aperture within the antenna portion that extends at least partially through the cochlear implant housing, an antenna within the antenna portion, a stimulation processor within the cochlear implant housing operably connected to the antenna and to the cochlear lead, and a magnet apparatus insert at least partially within the aperture.

A cutting tool positioner, for use with a cochlear implant, includes a centering post including a handle and an anchor, operably connected to the handle, configured to fit into the cochlear implant magnet pocket, and a tool guide, rotatably mounted on the centering post, including a slot configured to receive a cutting tool blade.

A center punch, for use with a cochlear implant, includes a centering post including a handle and an anchor, operably connected to the handle, configured to fit into the cochlear implant magnet pocket, and a cutter, mounted on the centering post and longitudinally movable relative to the centering post, including a blade with an overall circular shape.

A pocket enlargement tool, for use with a cochlear implant, includes a handle and means, operably connected to the handle, for enlarging the magnet pocket by shaving material off of the cochlear implant housing from within the magnet pocket as the handle is rotated.

A kit, for use with an implanted cochlear implant, includes an MRI-compatible magnet apparatus and one or more tools configured to remove a portion of the resilient material from the cochlear implant housing.

A coring and removal tool for use with a cochlear implant includes a centering template having an abutment, and a cutter, including a blade with an overall circular shape and an inner diameter that is greater than the diameter of the cochlear implant magnet pocket and less than the diameter of the cochlear implant antenna, that is movable relative to the centering template. The centering template and the cutter cochlear implant operably associated with one another such that the cutter blade will be centered relative to the magnet when the abutment engages the antenna portion.

There are a number of advantages associated with such apparatus and methods. For example, the present apparatus and methods facilitate the replacement of a conventional implant magnet with an MRI-compatible magnet apparatus in those instances where the MRI-compatible magnet apparatus will not physically fit into the magnet pocket of the associated cochlear implant.

A method, for use with a cochlear implant, includes the steps of removing a portion of the resilient material from the cochlear implant housing and replacing the cochlear implant magnet with an MRI-compatible magnet apparatus, and anchoring the MRI-compatible magnet apparatus to bone.

A magnet apparatus, for use with a cochlear implant or other implantable medical device, includes a case, at least one magnetic element within the case that is rotatable relative to the case, and a bone anchor associated with the case that is configured to anchor the case to bone. The present inventions also include cochlear implants with such a magnet apparatus.

There are a number of advantages associated with such apparatus and methods. For example, the present apparatus and methods facilitate the replacement of a conventional implant magnet with an MRI-compatible magnet apparatus. The present inventions also allow bone screws (or other anchors) to be employed in such a manner that the presence of a dominant MRI magnetic field will not result in trauma to the bone or damage to the magnet.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a top view of a conventional cochlear implant.

FIG. 2 is a section view taken along line 2-2 in FIG. 1.

FIG. 3 is a partial section view showing the conventional cochlear implant as an MRI magnetic field is being applied.

FIG. 4 is a partial section view of an aspect of a cochlear implant modification process in accordance with one embodiment of a present invention.

FIG. 5 is a section view of an aspect of a cochlear implant modification process in accordance with one embodiment of a present invention.

FIG. 6 is a top view of the aspect of the cochlear implant modification process illustrated in FIG. 5.

FIG. 7A is a top view of a magnet apparatus insert in accordance with one embodiment of a present invention.

FIG. 7B is a side view of an aspect of a cochlear implant modification process in accordance with one embodiment of a present invention.

FIG. 17 is a perspective view of a magnet apparatus insert in accordance with one embodiment of a present invention.

FIG. 18 is a side view of the magnet apparatus insert illustrated in FIG. 17.

FIG. 19 is a perspective view of a magnet apparatus insert in accordance with one embodiment of a present invention.

FIG. 20 is a side view of the magnet apparatus insert illustrated in FIG. 19.

FIG. 21 is a top view of a portion of a modified cochlear implant including the magnet apparatus insert illustrated in FIG. 19.

FIG. 87 is a perspective view of a magnet apparatus in accordance with one embodiment of a present invention.

FIG. 88 is a side view of the magnet apparatus illustrated in FIG. 87.

FIG. 89 is a section view of an aspect of a cochlear implant modification process in accordance with one embodiment of a present invention.

FIG. 90 is a perspective view of an aspect of a cochlear implant modification process in accordance with one embodiment of a present invention.

FIG. 91 is a perspective view of a modified cochlear implant in accordance with one embodiment of a present invention.

FIG. 104 is a perspective view of a stencil in accordance with one embodiment of a present invention.

FIG. 105 is a top view of the stencil illustrated in FIG. 104.

FIG. 106 is a top view of an aspect of a cochlear implant modification process in accordance with one embodiment of a present invention.

FIG. 107 is a side view of an aspect of a cochlear implant modification process in accordance with one embodiment of a present invention.

FIG. 108 is a side view of an aspect of a cochlear implant modification process in accordance with one embodiment of a present invention.

FIG. 117 is a side, partial section view of an aspect of a cochlear implant modification process in accordance with one embodiment of a present invention.

FIG. 118 is a side view of a portion of a center punch in accordance with one embodiment of a present invention.

FIG. 119 is a section view of an aspect of a cochlear implant modification process in accordance with one embodiment of a present invention.

FIG. 120 is a perspective view of a coring tool in accordance with one embodiment of a present invention.

FIG. 121 is a perspective view of a portion of the coring tool illustrated in FIG. 120.

FIG. 122 is a bottom view of the coring tool illustrated in FIG. 120.

FIG. 123 is a top view of an aspect of a cochlear implant modification process in accordance with one embodiment of a present invention.

FIG. 124 is an exploded perspective view of a coring and magnet removal tool in accordance with one embodiment of a present invention.

FIG. 125 is an exploded perspective view of the coring and magnet removal tool illustrated in FIG. 124.

FIG. 126 is a section view of the coring and magnet removal tool illustrated in FIG. 124.

FIG. 127 is a side view of an aspect of a cochlear implant modification process in accordance with one embodiment of a present invention.

FIG. 128 is a top view of an aspect of a cochlear implant modification process in accordance with one embodiment of a present invention.

Figure 129:
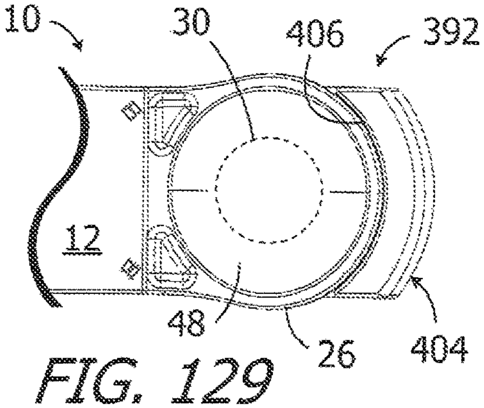

FIG. 129 is a bottom view of an aspect of a cochlear implant modification process in accordance with one embodiment of a present invention.

Figure 130:
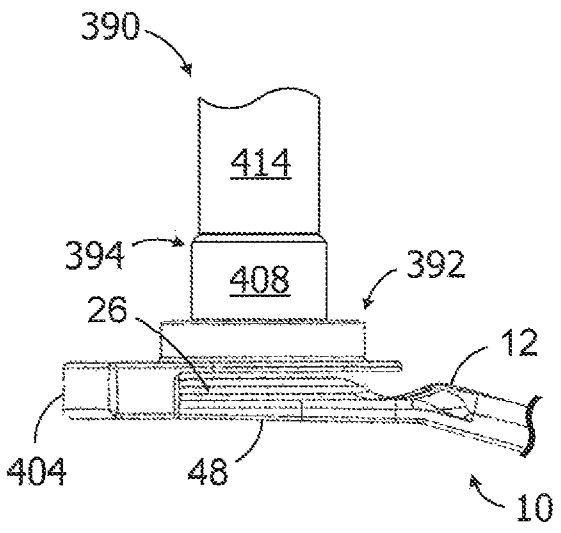

FIG. 130 is a side view of an aspect of a cochlear implant modification process in accordance with one embodiment of a present invention.

Figure 130A:
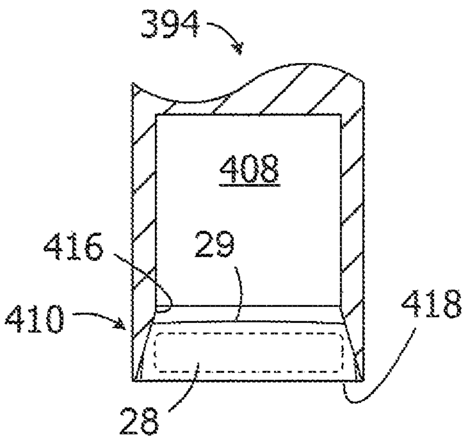

FIG. 130A is a section view of an aspect of a cochlear implant modification process in accordance with one embodiment of a present invention.

Figure 131:
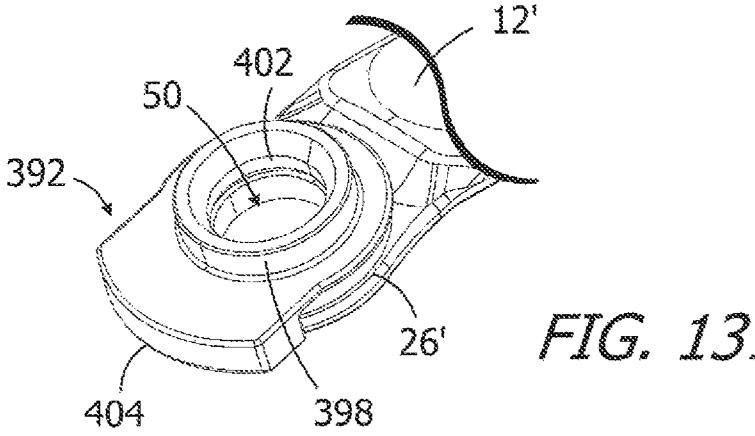

FIG. 131 is a perspective view of an aspect of a cochlear implant modification process in accordance with one embodiment of a present invention.

Figure 132:
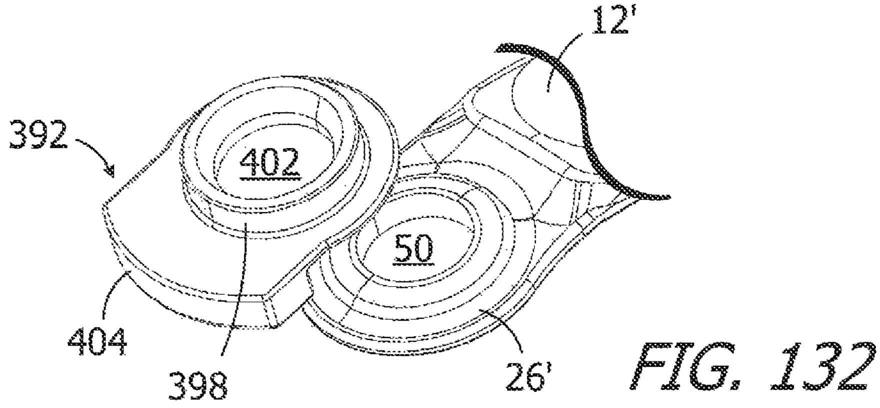

FIG. 132 is a perspective view of an aspect of a cochlear implant modification process in accordance with one embodiment of a present invention.

Figure 133:
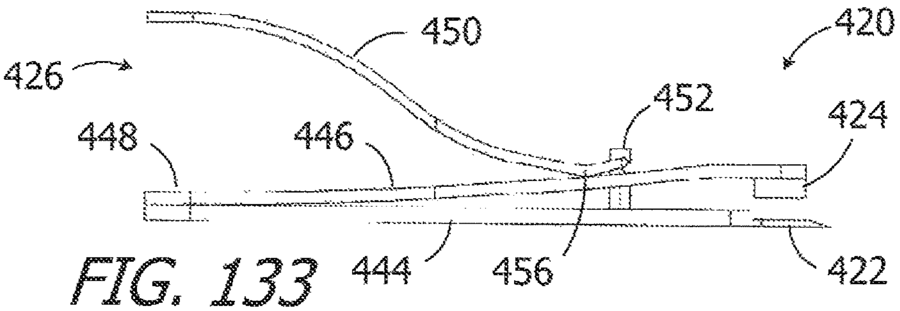

FIG. 133 is a side view of a coring and magnet removal tool in accordance with one embodiment of a present invention.

Figure 134:
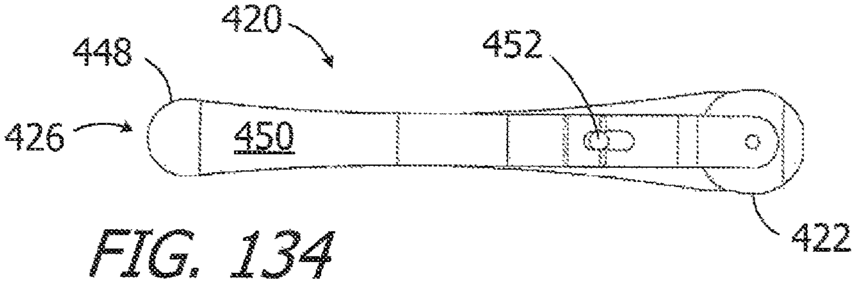

FIG. 134 is a top view of the coring and magnet removal tool illustrated in FIG. 133.

Figure 135:
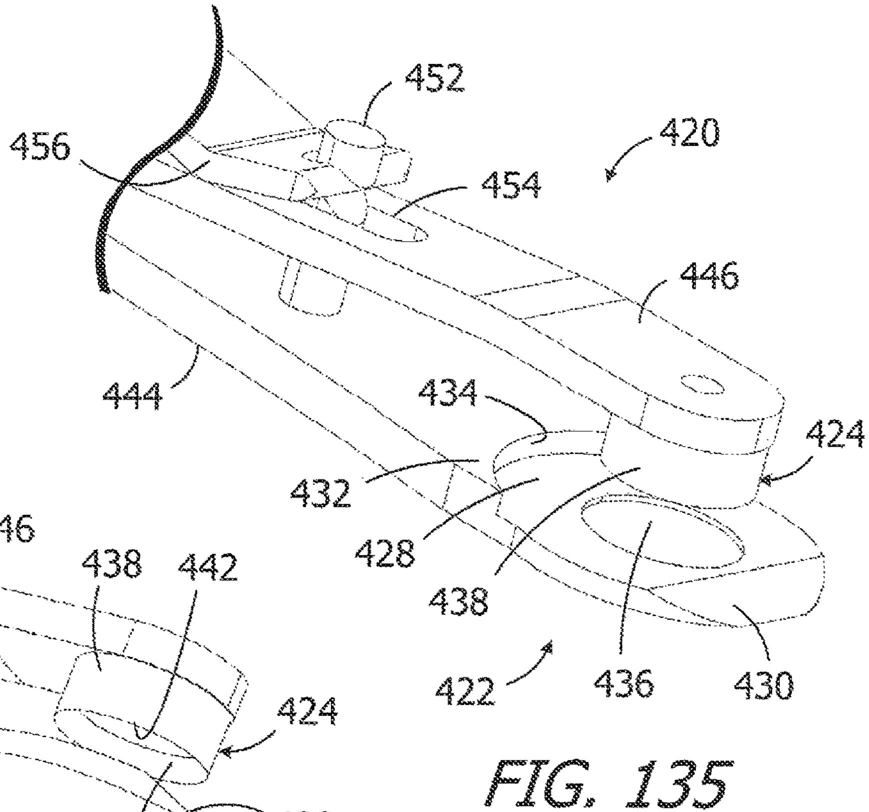

FIG. 135 is a perspective view of a portion of the coring and magnet removal tool illustrated in FIG. 133.

Figure 136:
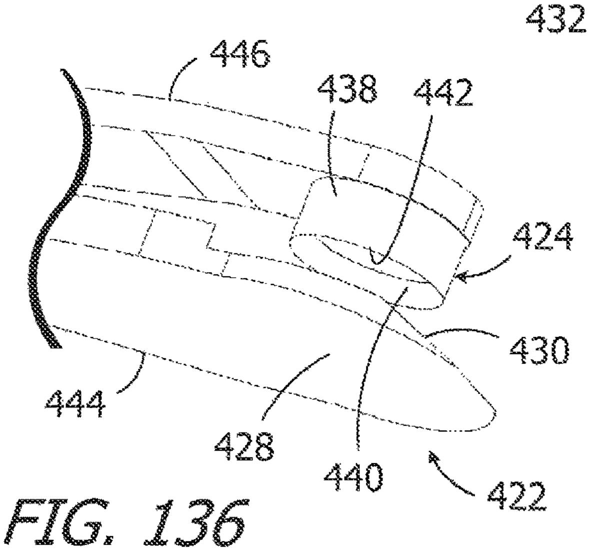

FIG. 136 is a perspective view of a portion of the coring and magnet removal tool illustrated in FIG. 133.

Figure 137:
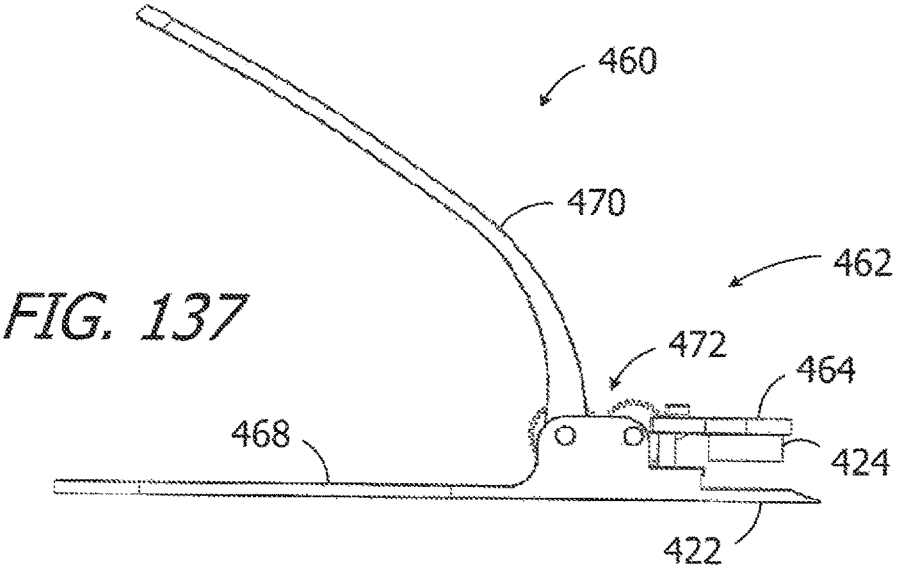

FIG. 137 is a side view of a coring and magnet removal tool in accordance with one embodiment of a present invention.

Figure 138:
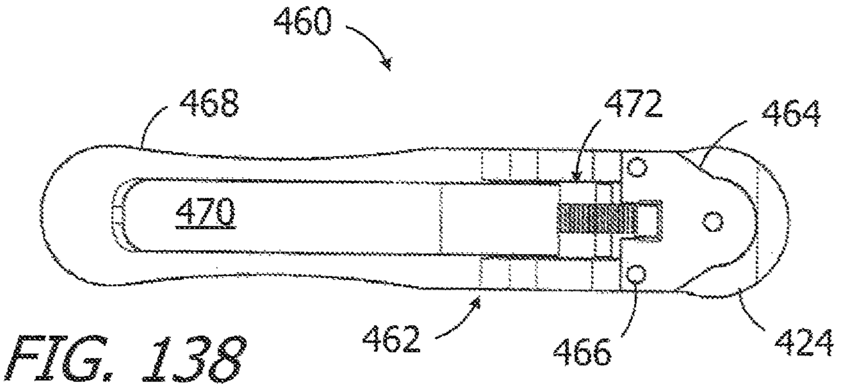

FIG. 138 is a top view of the coring and magnet removal tool illustrated in FIG. 137.

Figure 139:
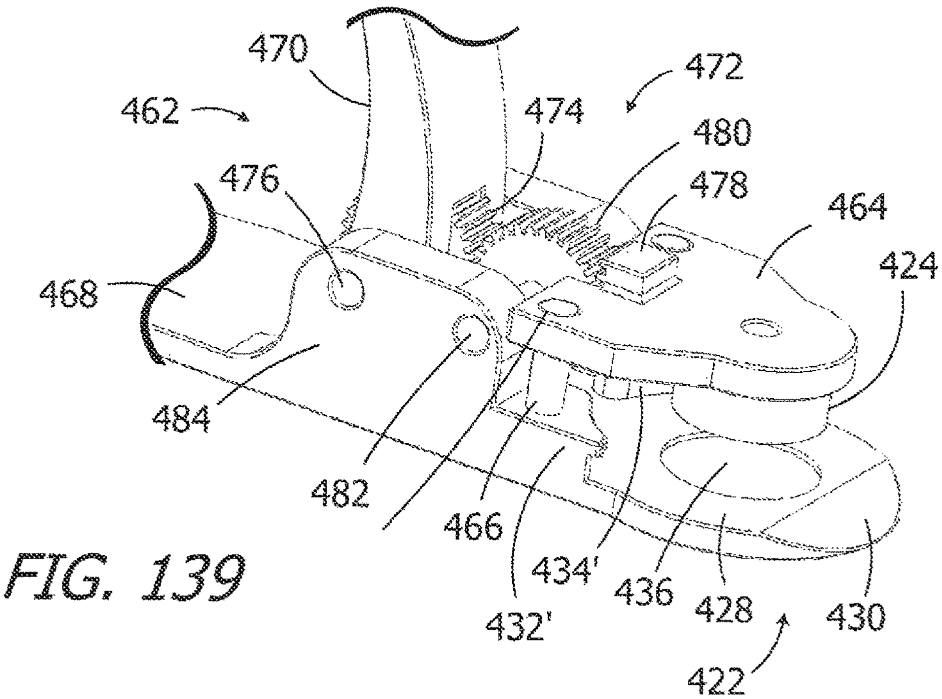

FIG. 139 is a perspective view of a portion of the coring and magnet removal tool illustrated in FIG. 137.

Figure 140:
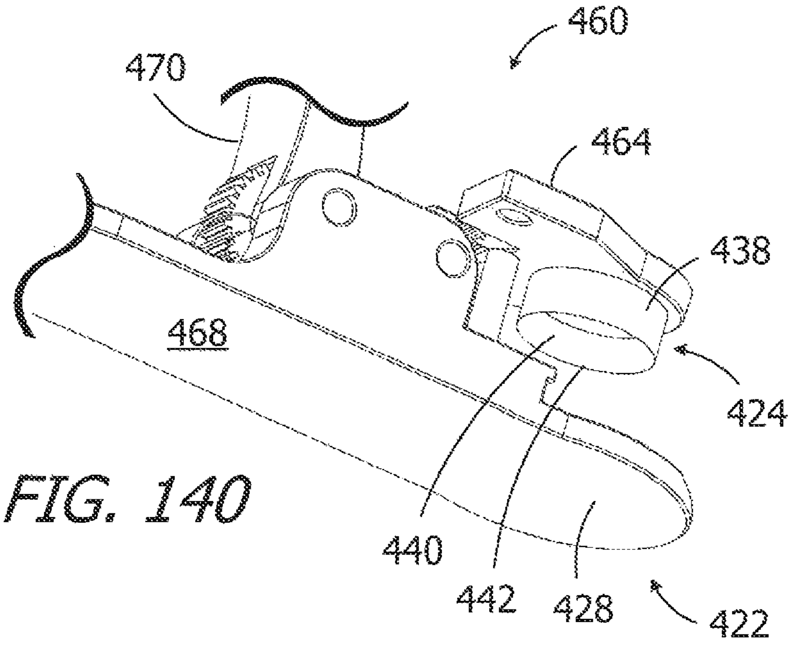

FIG. 140 is an exploded perspective view of a portion of the coring and magnet removal tool illustrated in FIG. 137.

Figure 141:
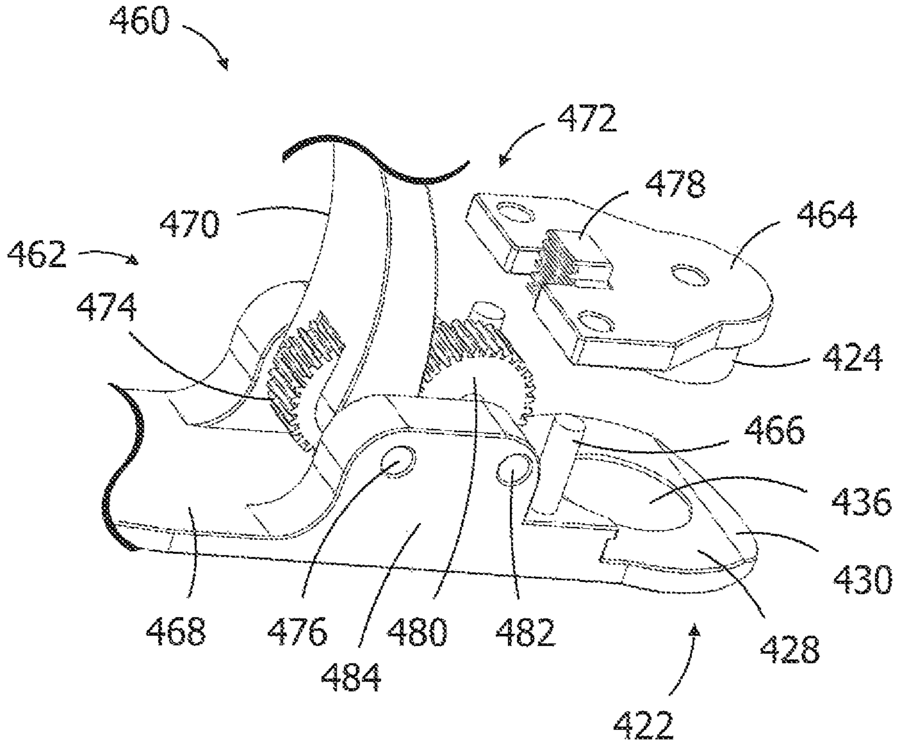

FIG. 141 is an exploded perspective view of a portion of the coring and magnet removal tool illustrated in FIG. 137.

Figure 142:
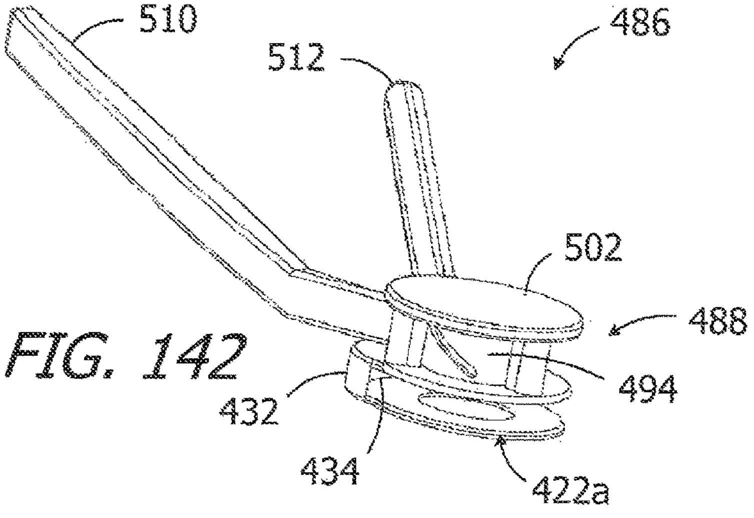

FIG. 142 is a perspective view of a coring and magnet removal tool in accordance with one embodiment of a present invention.

Figure 143:
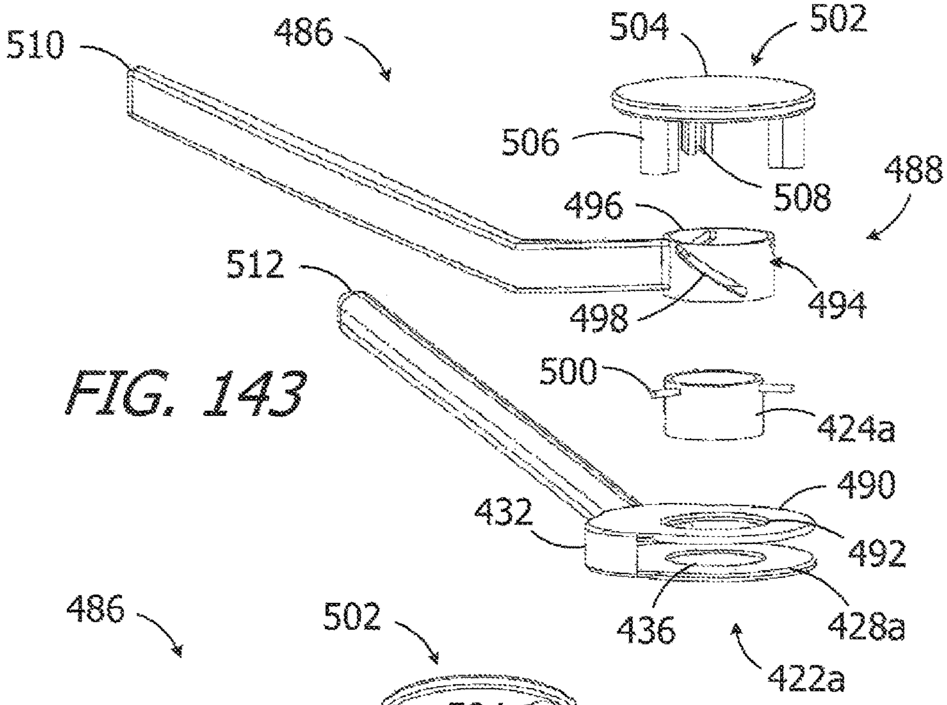

FIG. 143 is an exploded perspective view of the coring and magnet removal tool illustrated in FIG. 142.

Figure 144:
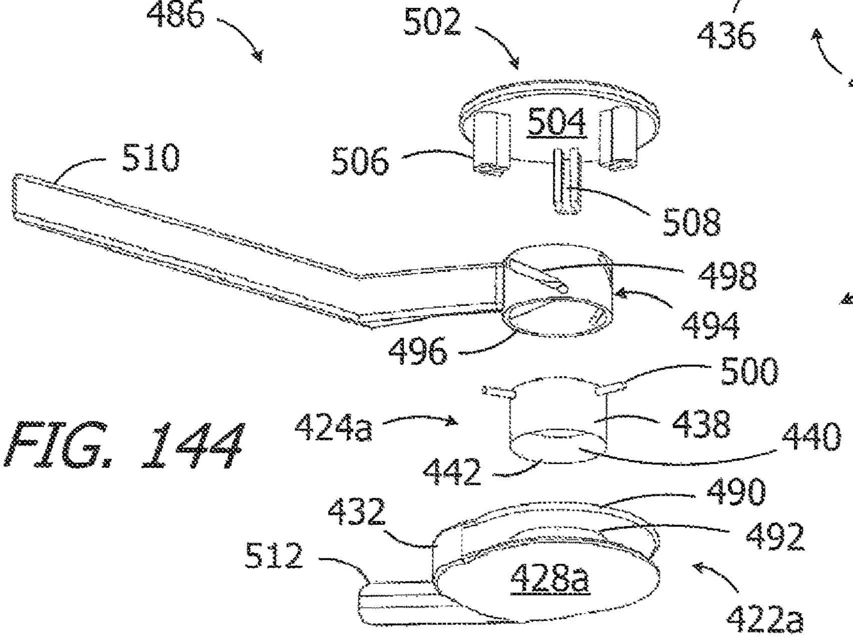

FIG. 144 is an exploded perspective view of the coring and magnet removal tool illustrated in FIG. 142.

Figure 145:
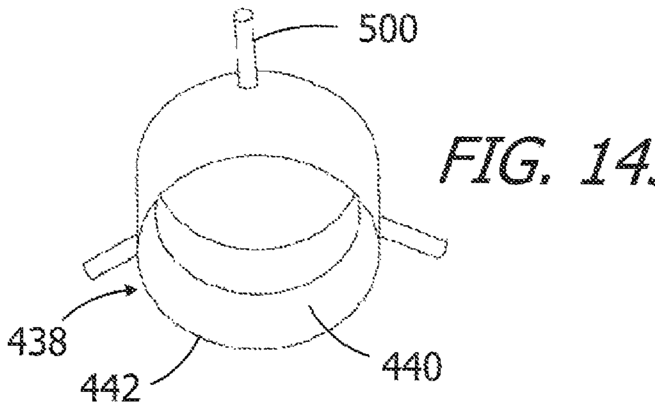

FIG. 145 is a perspective view of a portion of the coring and magnet removal tool illustrated in FIG. 142.

Figure 146:
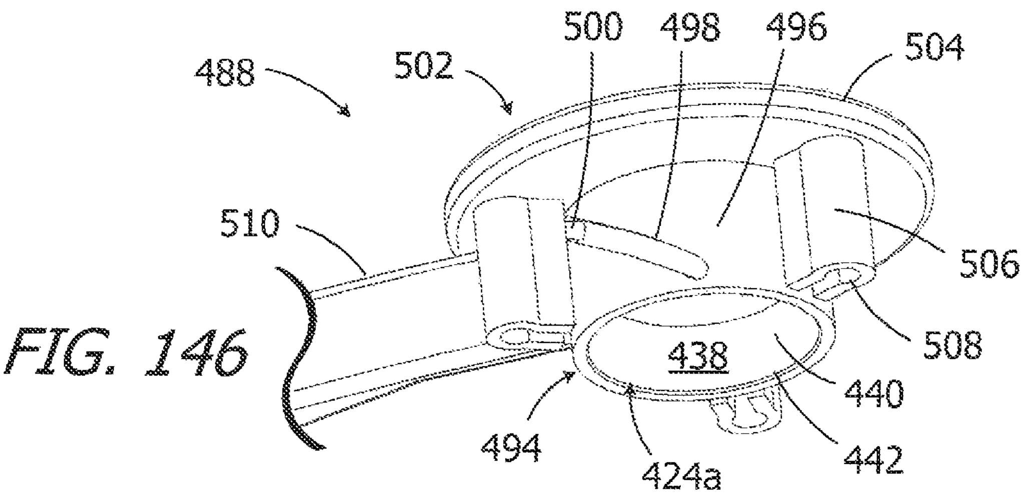

FIG. 146 is a perspective view of a portion of the coring and magnet removal tool illustrated in FIG. 142.

Figure 147:
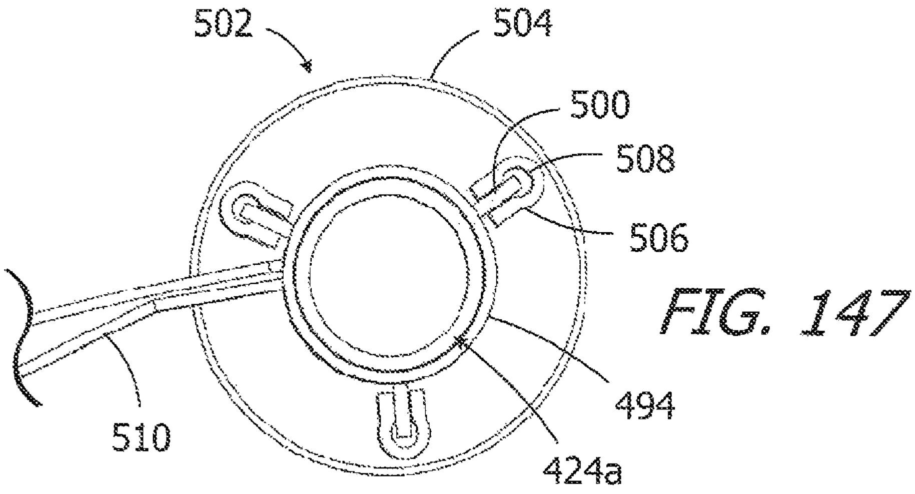

FIG. 147 is a bottom view of a portion of the coring and magnet removal tool illustrated in FIG. 142.

Figure 148:
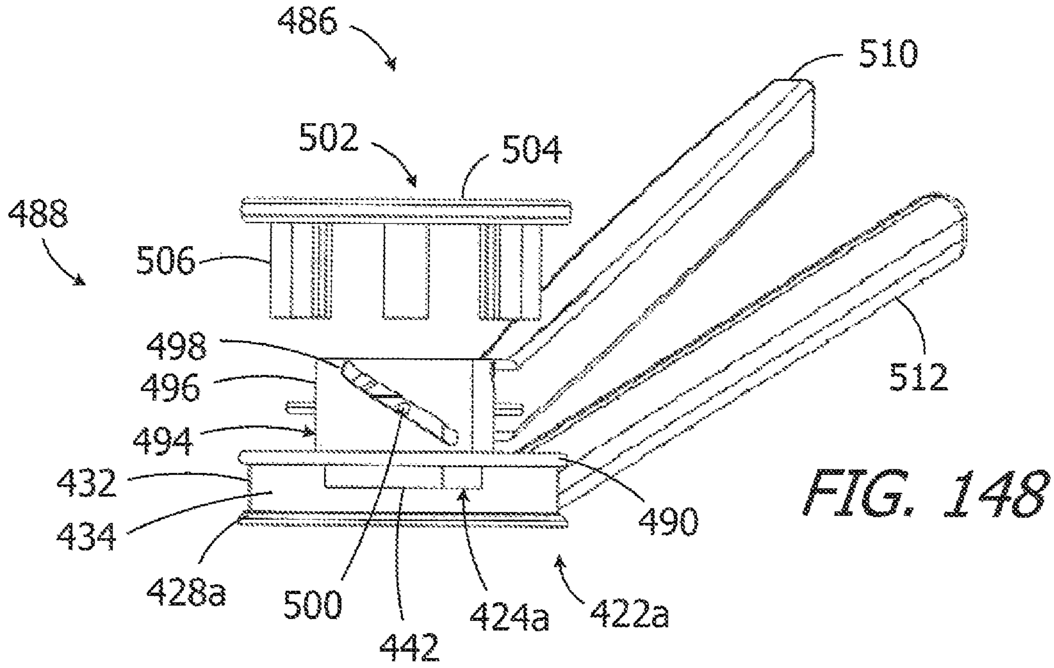

FIG. 148 is a partially exploded view of the coring and magnet removal tool illustrated in FIG. 142 with the blade partially extended.

FIG. 149 is a side view of a coring and magnet removal tool in accordance with one embodiment of a present invention.

FIG. 150 is a perspective view of a portion of the coring and magnet removal tool illustrated in FIG. 149.

FIG. 151 is a side view of a portion of the coring and magnet removal tool illustrated in FIG. 149.

FIG. 152 is a side view of an aspect of a cochlear implant modification process in accordance with one embodiment of a present invention.

Figure 153:
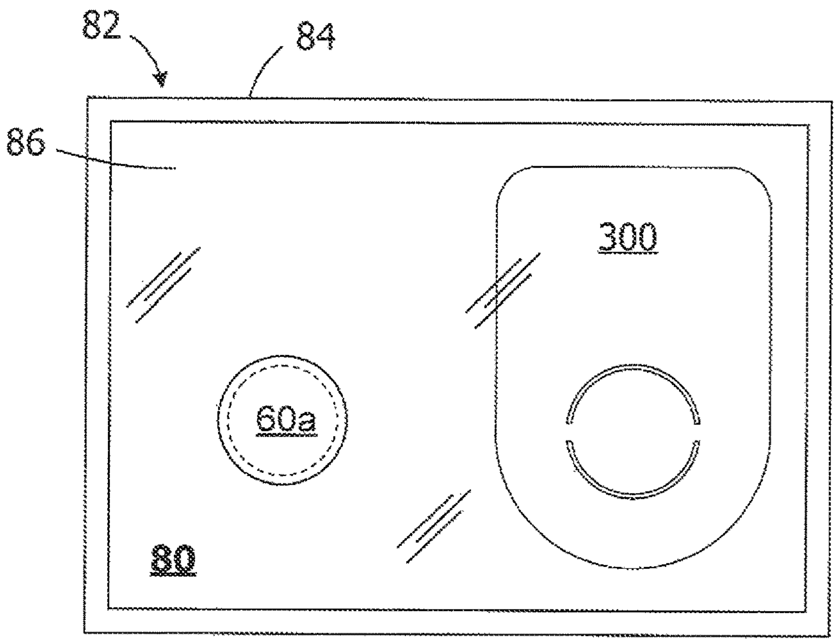

FIG. 153 is a plan view of a cochlear implant kit in accordance with one embodiment of a present invention.

Figure 154:
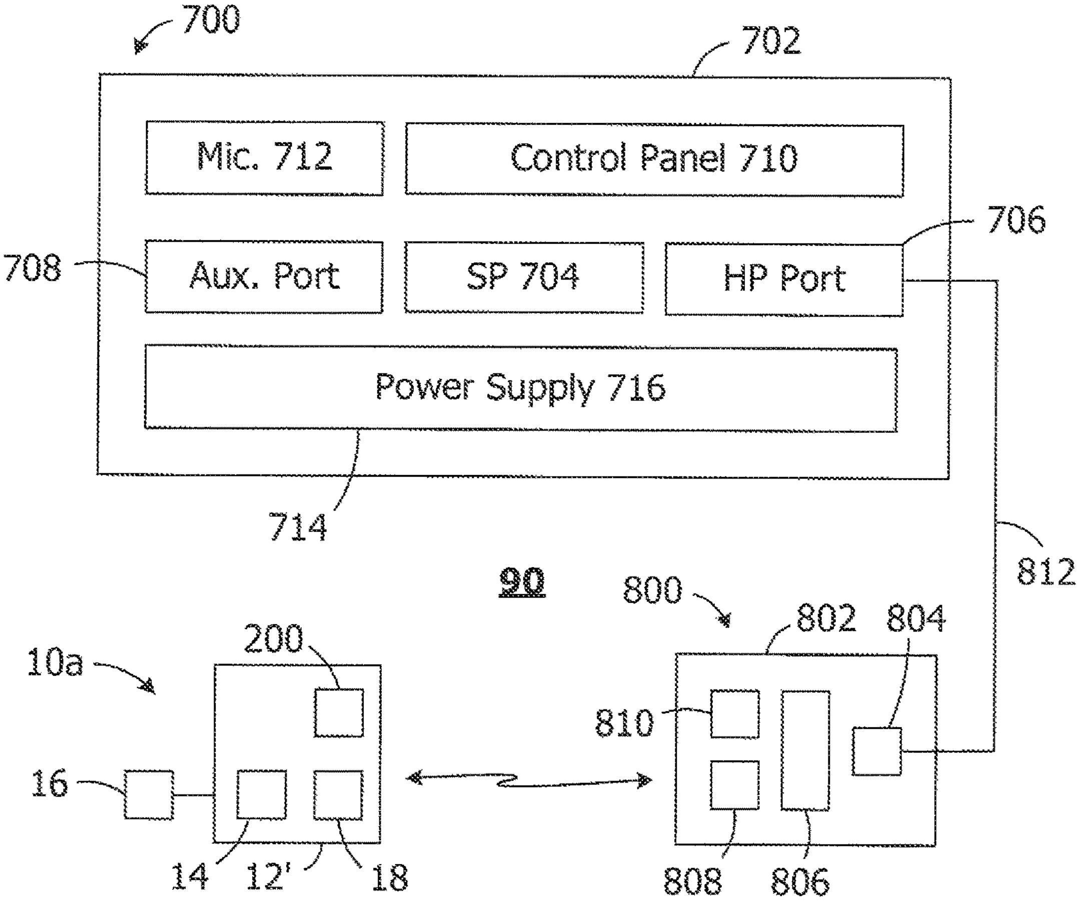

FIG. 154 is a block diagram of a cochlear implant system in accordance with one embodiment of a present invention.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present inventions include various apparatus and methods that facilitate in situ replacement of conventional implant magnets with MRI-compatible magnet apparatus (or "magnet apparatus"). Some of the methods and apparatus may also involve anchoring of the magnet apparatus to bone. In at least some instances, the magnet will be removed in situ from the cochlear implant, a portion of the implant housing will be removed to accommodate the larger magnet apparatus, and the magnet apparatus will be added to the modified cochlear implant housing. As used herein, a "larger" magnet apparatus is a magnet apparatus that is larger in one or more of diameter, perimeter, length, width and thickness than the magnet that has been removed. The magnet will also be removed and replaced by the magnet apparatus without damaging the antenna. Additionally, in at least some instances, a MRI-compatible magnet apparatus will not be secured to the remainder of the cochlear implant, thereby allowing the cochlear implant to be removed (if necessary) without disturbing the bone anchor.

One example of a conventional cochlear implant that may be modified in accordance with the present inventions is the cochlear implant 10 described above with reference to FIGS. 1-2. Access to the implanted cochlear implant 10 may be obtained, for example, by making an incision that allows a skin flap over the cochlear implant and, in particular, over the antenna portion 26 of the housing 12, to be lifted. The magnet 28 may be removed from the magnet pocket 30 by way of the magnet aperture 42 (FIG. 4) after the access has been obtained. A portion of the housing 12 may then be removed in order to increase the available volume, as compared to the magnet pocket 30, for the magnet apparatus. In at least some implementations, the removed portion of the housing 12 may be located radially inward of the antenna 18, radially outward of the magnet pocket 30, and may extend through the both of the housing top wall 44 and the housing bottom wall 48 (which defines the bottom surface of the housing). As such, the magnet pocket 30 and aperture 42 will be removed, as will portions of the top wall 44, the bottom wall 48, and an annular section of housing material which extends around the magnet pocket. The partial housing 12' illustrated in FIGS. 5 and 6 includes a modified antenna portion 26' with an aperture 50 that extends completely through the housing and that is located radially inward of the antenna 18. The aperture 50 may be cylindrical (as shown) or other shapes such as, but not limited to, square, hexagonal, and triangular. The thickness of the aperture 50 is equal to the thickness of the modified antenna portion 26'. Exemplary tools that may be used to form the aperture 50 are described below with reference to FIGS. 104-152.

The exemplary magnet apparatus insert **60*a* illustrated in FIGS. 7A and 7B may be inserted into the aperture 50 of the partial housing 12' to form a modified cochlear implant. The exemplary magnet apparatus insert 60*a* includes a housing portion replacement 100 and an MRI-compatible magnet apparatus 200 that is embedded within the housing portion replacement. The housing portion replacement 100, which may be formed from the same material as the cochlear implant housing 12 (e.g., a silicone elastomer) and overmolded onto the magnet apparatus 200, includes a magnet housing 102 (e.g., a disk-shaped housing) with a magnet pocket 104 in which the magnet apparatus 200 is located. The shape and size of magnet housing 102 (e.g., the diameter and thickness) is the same as, or essentially the same as, that of the aperture 50. The exemplary magnet apparatus 200, which is discussed in greater detail below with reference to FIGS. 28-33, is larger than the removed magnet 28**.

Figure 8:
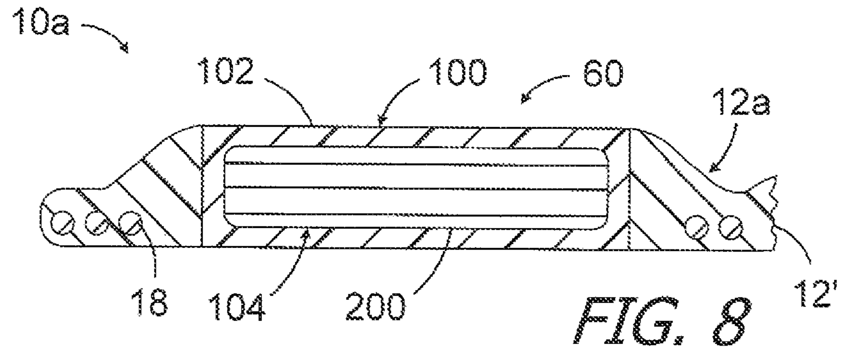
FIG. 8 is a partial section view of a modified cochlear implant in accordance with one embodiment of a present invention.

The housing portion replacement 100 of the magnet apparatus insert **60*a* may be secured to partial housing 12' with, for example, adhesive applied to the perimeter of the housing portion replacement to form the modified cochlear implant 10*a* illustrated in FIG. 8. The modified cochlear implant 10*a* includes a housing 12*a*, which consists of the partial housing 12' and the housing portion replacement 100, as well as the magnet apparatus 200 in place of the removed magnet 28. The antenna 18 and other portions of the cochlear implant 10 (FIGS. 1 and 2**) remain unchanged.

The cochlear implant 10 may be modified in other ways that also facilitate the replacement of the magnet 28 with an MRI-compatible magnet apparatus such as magnet apparatus 200. To that end, and referring first to FIG. 9, the partial housing 12" includes a modified antenna portion 26" with an aperture 52 that extends partially through the housing and that is located radially inward of the antenna 18. The aperture 52 may be cylindrical (as shown) or other shapes such as, but not limited to, square, hexagonal, and triangular. The thickness of the aperture 50 is less the thickness of the modified antenna portion 26" and housing bottom wall 48 remains intact. Exemplary tools that may be used to form the aperture **50*a* are described below with reference to FIGS. 36-49**.

Figure 10:
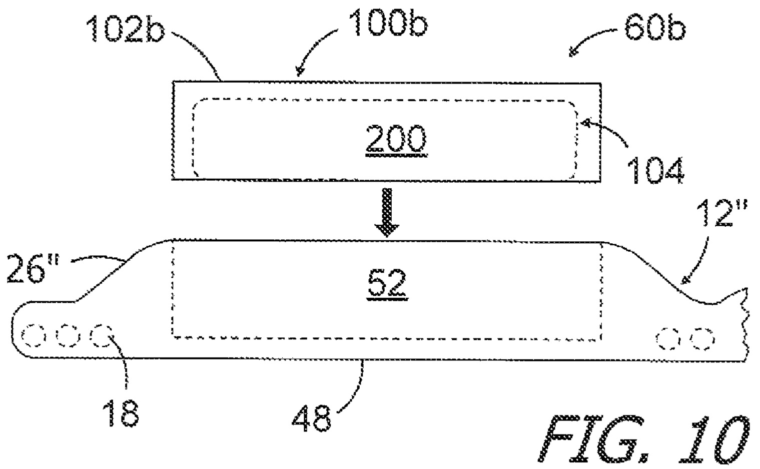
FIG. 10 is a side view of an aspect of a cochlear implant modification process in accordance with one embodiment of a present invention.

The exemplary magnet apparatus insert **60*b* illustrated in FIG. 10 may be inserted into the aperture 52 of the partial housing 12" to form a modified cochlear implant. The exemplary magnet apparatus insert 60*b* is substantially similar to insert 60*a* and similar elements are represented by similar reference numerals. Here, however, the magnet housing 102*b* of the housing portion replacement 100*b* is somewhat thinner so as to conform to the thinner aperture 52. The magnet pocket 104 and magnet apparatus 200 also extend to the bottom of the magnet housing 102*b***.

Figure 11:
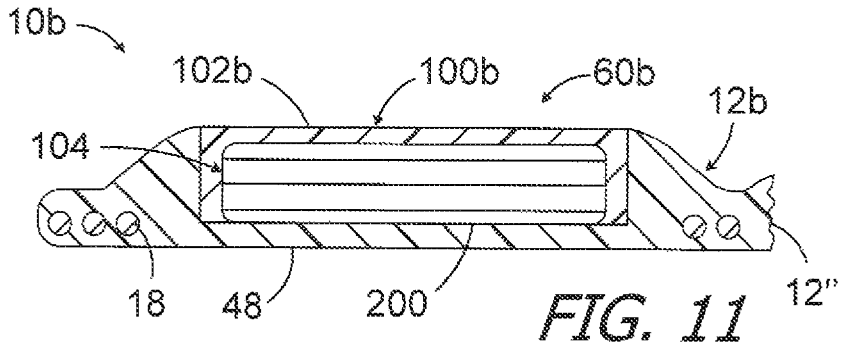
FIG. 11 is a partial section view of a modified cochlear implant in accordance with one embodiment of a present invention.

The housing portion replacement **100*b* of the magnet apparatus insert 60*b* may be secured to the partial housing 12" with, for example, adhesive to form the modified cochlear implant 10*b* illustrated in FIG. 11. The adhesive may be located on the bottom of the housing portion replacement 100*b*, in addition to the outer perimeter, in order provide additional resistance to magnetic torque (FIG. 3). The modified cochlear implant 10*b* includes a housing 12*b*, which consists of the partial housing 12" and the housing portion replacement 100*b***, as well as the magnet apparatus 200 in place of the removed magnet 28. The antenna 18 and other portions of the cochlear implant 10 remain unchanged.

Figure 12:
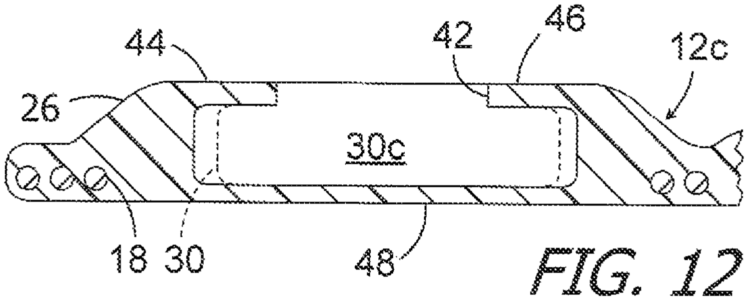
FIG. 12 is a section view of an aspect of a cochlear implant modification process in accordance with one embodiment of a present invention.
Figure 13:
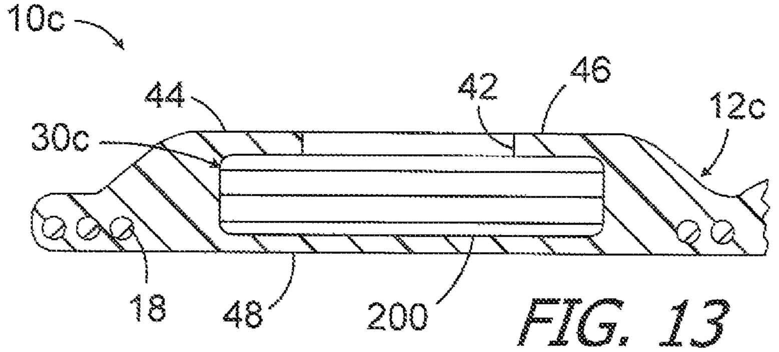
FIG. 13 is a partial section view of a modified cochlear implant in accordance with one embodiment of a present invention.

A cochlear implant, such as cochlear implant 10, may also be modified by simply enlarging the magnet pocket in situ in order to accommodate an MRI-compatible magnet apparatus that is larger than the magnet 28. Referring to FIG. 12, housing material may be removed in such a manner that the modified housing 12*c* includes a magnet pocket 30*c* that is larger in diameter than the pre-modification magnet pocket 30 (shown in dashed lines). The magnet apparatus 200 may then be inserted into the magnet pocket 30*c* to form the modified cochlear implant 10*c* illustrated in FIG. 13. Here too, the antenna 18 and other portions of the cochlear implant 10 remain unchanged. One example of a tool that may be used to form the enlarged magnet pocket 30*c* is described below with reference to FIGS. 120-123.

Figure 14:
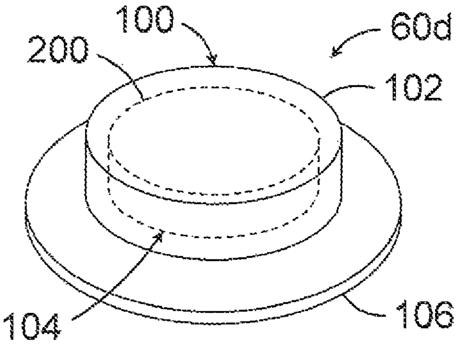
FIG. 14 is a perspective view of a magnet apparatus insert in accordance with one embodiment of a present invention.
Figure 15:
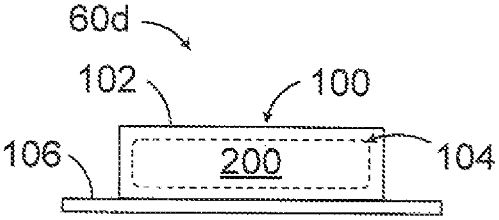
FIG. 15 is a side view of the magnet apparatus insert illustrated in FIG. 14.

Another exemplary magnet apparatus insert 60*d* is illustrated in FIGS. 14 and 15. Magnet apparatus insert 60*d* is substantially similar to magnet apparatus insert 60*a* and similar elements are represented by similar reference numerals. Here, however, a thin disk-shaped base 106 is located under the magnet housing 102. The base 106 has a larger diameter than the magnet housing 102 and, therefore, extends radially beyond the outer perimeter of the magnet housing. The base 106 may be integral with the magnet housing 102, as shown, or may be a separate element that is secured to the magnet housing.

Figure 16:
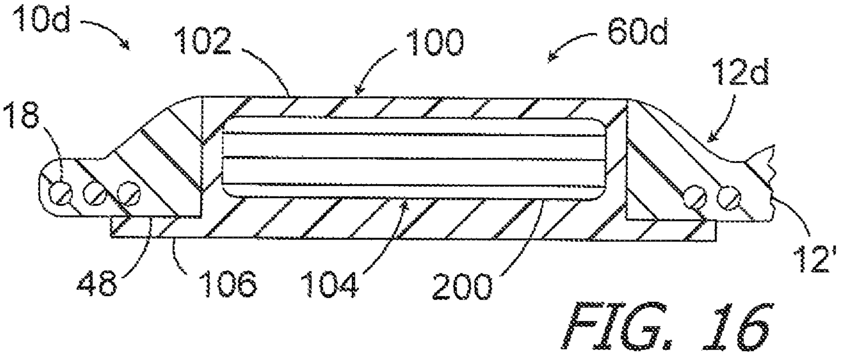
FIG. 16 is a partial section view of a modified cochlear implant including the magnet apparatus insert illustrated in FIG. 14.

The magnet apparatus insert 60*d* may be added to, for example, the above-described partial housing 12' (FIGS. 5 and 6), which includes the modified antenna portion 26' with the aperture 50. During insertion, the modified antenna portion 26' may be bent away from the skull (and bent relative to the remainder of the cochlear implant) so that the magnet apparatus insert 60*d* can be positioned under the bottom wall 48 with the magnet housing 102 aligned with the aperture 50. The modified antenna portion 26' may then be pressed downwardly until the bottom wall 48 rests on the base 106 in the manner illustrated in FIG. 16 to complete the modified cochlear implant 10*d*. Adhesive may be used to secure the magnet apparatus insert 60*d* to the partial housing 12'. The adhesive may be located on the top surface of the base 106, in addition to the outer perimeter of the magnet housing 102, in order provide additional resistance to magnetic torque (FIG. 3). The antenna 18 and other portions of the cochlear implant 10 remain unchanged.

The exemplary magnet apparatus insert 60*e* illustrated in FIGS. 17 and 18 is substantially similar to magnet apparatus insert 60*d* and similar elements are represented by similar reference numerals. Here, however, the base 106 includes an aperture 108 that allows the surgeon to secure the magnet apparatus insert 60*e* to the skull with a bone screw 110 (or other bone anchor) to further resist magnetic torque. The modified cochlear implant may then be completed in the manner described above with reference to insert 60*d*.

Another magnet apparatus insert that may be added to, for example, the above-described partial housing 12' (FIGS. 5 and 6) is the magnet apparatus insert generally represented by reference numeral 60*f* in FIGS. 19 and 20. The magnet apparatus insert 60*f* is similar to magnet apparatus insert 60*a* and similar elements are represented by similar reference numerals. For example, the housing portion replacement 100*f* includes a magnet housing 102*f* with a magnet pocket 104 in which the magnet apparatus 200 is located. The magnet housing 102*f* is, however, longer than the magnet housing 102 and includes a plurality of flanges 112 that extend radially from the longitudinal ends of the magnet housing.

During the addition of the magnet apparatus insert 60*f* to the partial housing 12' (FIGS. 5-6), the modified antenna portion 26' may be bent away from the skull (and bent relative to the remainder of the cochlear implant) so that the magnet apparatus insert 60*f* can be positioned under the bottom wall 48 with the magnet housing 102*f* aligned with the aperture 50. The modified antenna portion 26' may then be pressed downwardly until the bottom wall 48 rests on the lower set of flanges 112. The upper set of flanges 112 may be pulled out of the aperture 50 and positioned over the top wall 44, as shown in FIG. 21, to complete the modified cochlear implant 10*f*. Adhesive may be used to secure the magnet apparatus insert 60*f* to the partial housing 12'. In addition to the outer perimeter of the magnet housing 102*f*, the adhesive may be located on the top surfaces of the lower flanges 12 and the bottom surfaces of the upper flanges 12, the adhering the insert 60*f* to the top and bottom walls 44 and 48 of the partial housing 12' as well as to the material that defines the aperture 50. The antenna 18 and other portions of the cochlear implant 10 remain unchanged.

Figure 22:
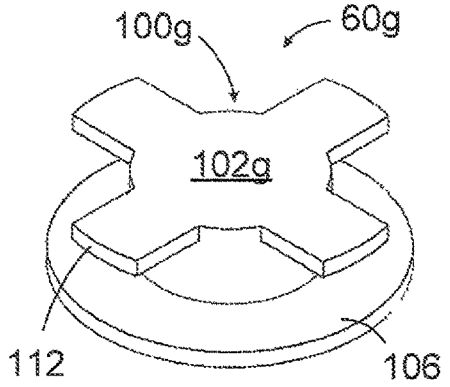
FIG. 22 is a perspective view of a magnet apparatus insert in accordance with one embodiment of a present invention.
Figure 23:
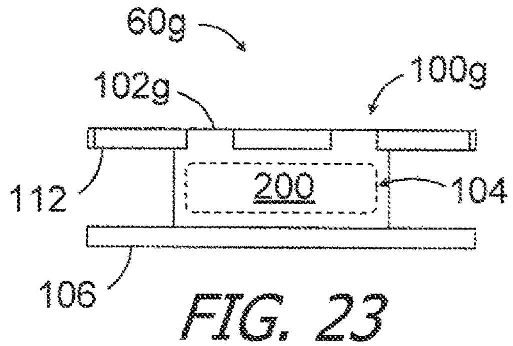
FIG. 23 is a side view of the magnet apparatus insert illustrated in FIG. 22.
Figure 24:
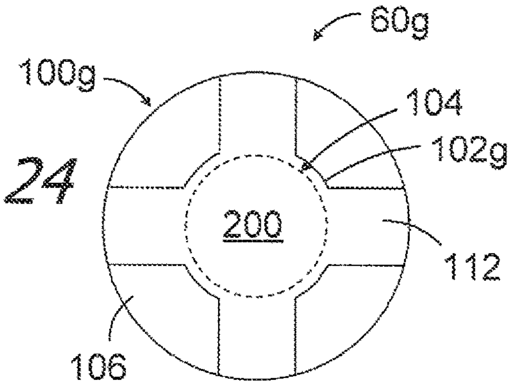
FIG. 24 is a top view of the magnet apparatus insert illustrated in FIG. 22.

Turning to FIGS. 22-24, the exemplary magnet apparatus insert 60*g* is substantially similar to magnet apparatus insert 60*f* and similar elements are represented by similar reference numerals. To that end, the magnet apparatus insert 60*g* includes a housing portion replacement 100*g*, with a magnet housing 102*g* for the magnet pocket 104 and magnet apparatus 200, and a plurality of flanges 112 that extend radially from one longitudinal end of the magnet housing. Here, however, a base 106 is associated with the other longitudinal end instead of a second set of flanges 112. The magnet apparatus insert 60*g* may be combined with, for example, the partial housing 12' in the manner described above to form a modified cochlear implant.

Figure 25:
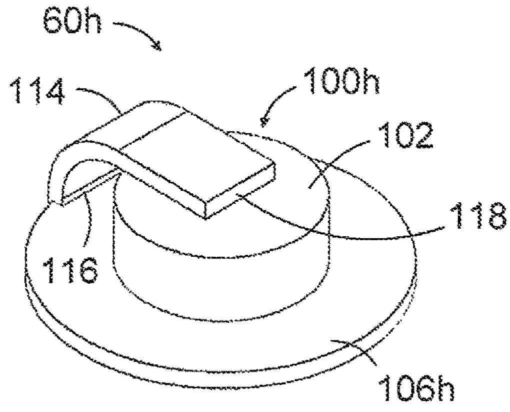
FIG. 25 is a perspective view of a magnet apparatus insert in accordance with one embodiment of a present invention.
Figure 26:
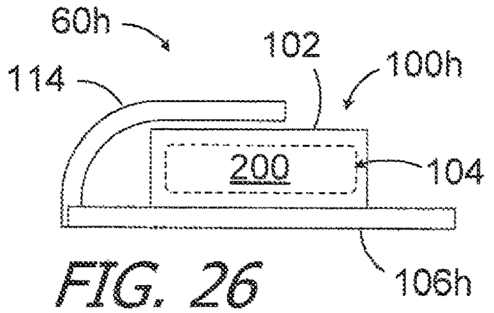
FIG. 26 is a side view of the magnet apparatus insert illustrated in FIG. 25.

Another exemplary magnet apparatus insert is generally represented by reference numeral 60*h* in FIGS. 25 and 26. Magnet apparatus insert 60*h* is substantially similar to magnet apparatus insert 60*d* and similar elements are represented by similar reference numerals. Here, however, the base 106*h* is slightly larger in diameter than base 106 and a flexible flap 114 extends from the base. More specifically, the flap 114 has a base end 116 that is attached to (or is integral with) the base 106*h* and a free end 118.

Figure 27A:
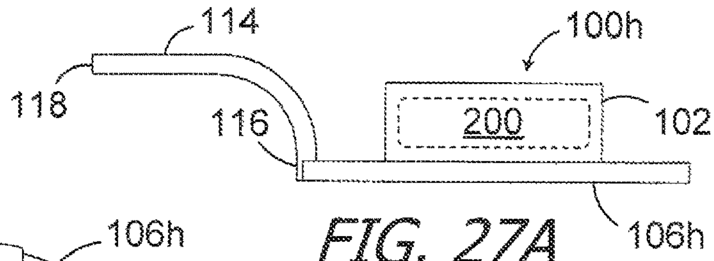
FIG. 27A is a side view of the magnet apparatus insert illustrated in FIG. 25 with the flap bent.
Figure 27B:
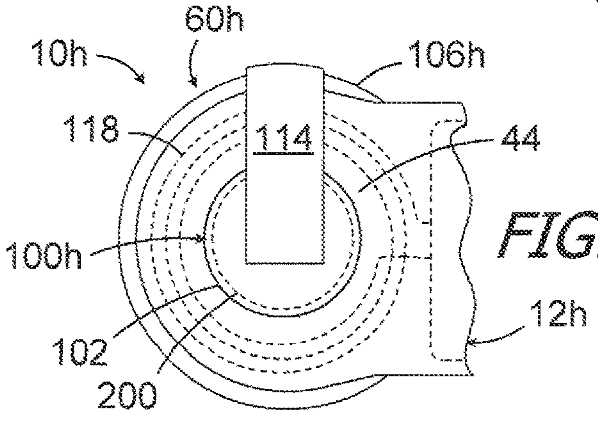
FIG. 27B is a top view of a portion of a modified cochlear implant including the magnet apparatus insert illustrated in FIG. 25.
Figure 28:
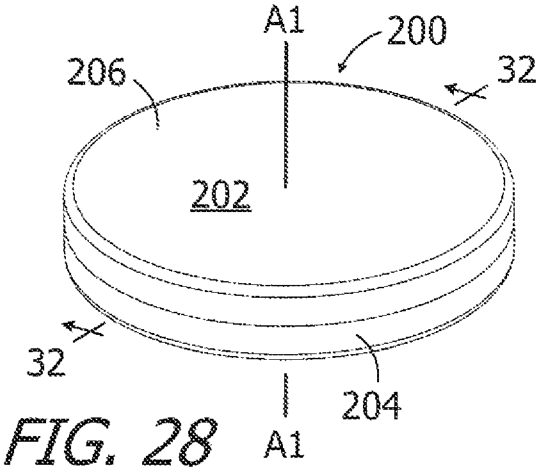
FIG. 28 is a perspective view of an implant magnet apparatus in accordance with one embodiment of a present invention.
Figure 29:
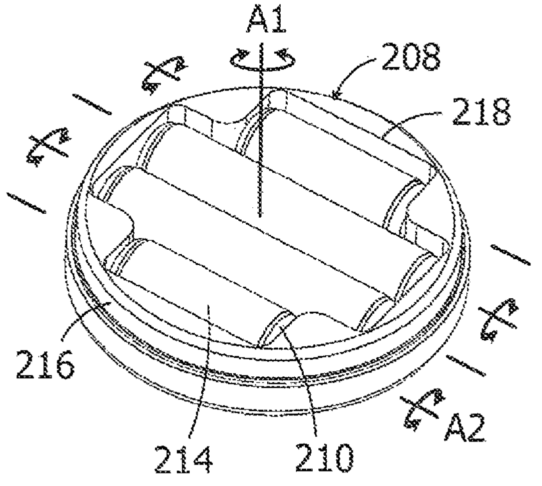
FIG. 29 is a perspective view of a portion of the implant magnet apparatus illustrated in FIG. 28.
Figure 30:
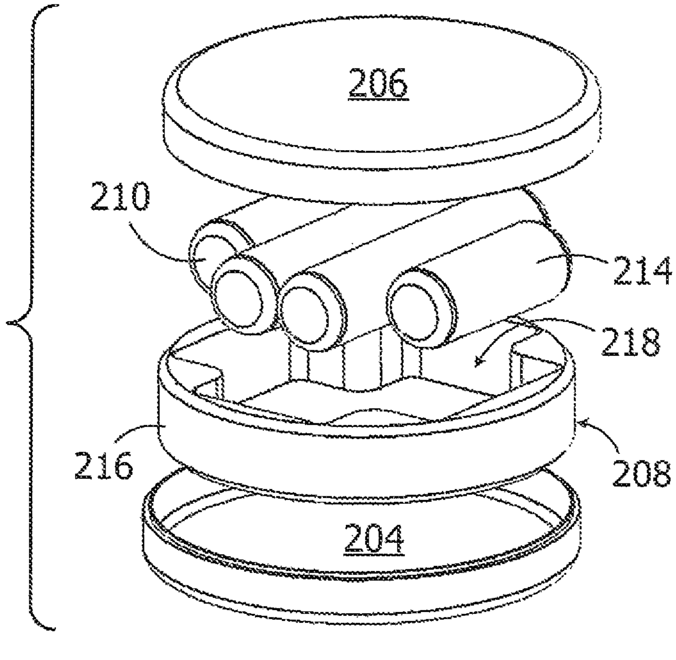
FIG. 30 is an exploded view of the implant magnet apparatus illustrated in FIG. 28.
Figure 31:
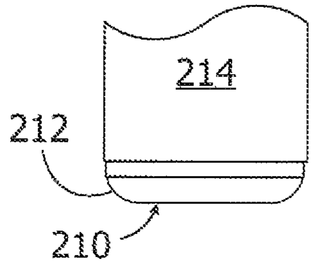
FIG. 31 is a plan view of a portion of the implant magnet apparatus illustrated in FIG. 28.
Figure 32:
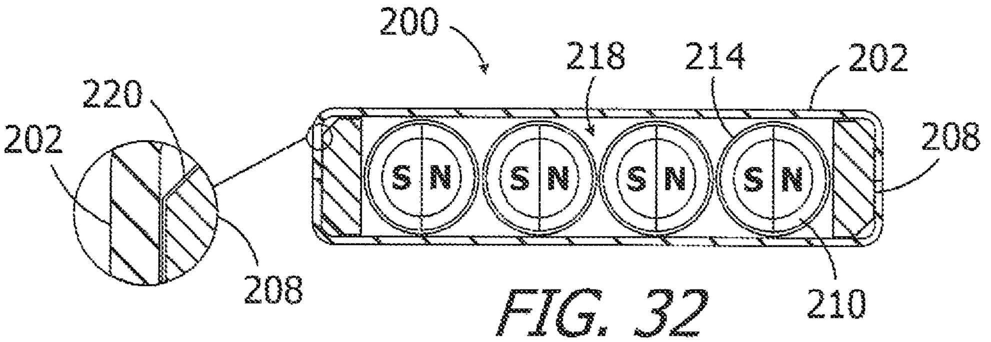
FIG. 32 is a section view take along line 32-32 in FIG. 28.

The magnet apparatus insert 60*h* may be combined with, for example, the partial housing 12' in the manner described above with reference to FIG. 16 while the flap 114 is bent out of the way in, for example, the manner illustrated in FIG. 27A. Adhesive located on the top surface of the base 106*h*, as well as the outer perimeter of the magnet housing 102, may be used to secure the magnet apparatus insert 60*h* to the partial housing 12'. The flap 114 may then be bent back and positioned over the housing top wall 44 and the housing portion replacement 100*h*, and secured thereto with adhesive, to complete the modified cochlear implant 10*h* illustrated in FIG. 27B. Here too, the antenna 18 and other portions of the cochlear implant 10 remain unchanged.

Turning to FIGS. 28-32, the exemplary MRI-compatible magnet apparatus 200 includes a case 202, with base 204 and a cover 206, a magnet frame 208, and a plurality of elongate diametrically magnetized magnets 210 within the frame that define a N-S direction. The exemplary case 202 is disk-shaped and defines a central axis A1, which is also the central axis of the magnet frame 208. The magnet frame 208 is freely rotatable relative to the case 202 about the central axis A1 over 360°. The magnets 210 rotate with the magnet frame 208 about the central axis A1. Each magnet 210 is also freely rotatable relative to the magnet frame 208 about its own longitudinal axis A2 over 360°. In the illustrated implementation, the longitudinal axes A2 are parallel to one another and are perpendicular to the central axis A1. The axes A2 may be non-perpendicular to the central axis A1 in other implementations.

Given the ability of each magnet 210 to freely rotate about its longitudinal axis A2, the magnets 210 align with one another in the N-S direction in the absence of a relatively strong external magnetic field (e.g., the MRI magnetic field discussed below with reference to FIG. 33), and the at rest N-S orientation of the magnets 210 will be perpendicular to the central axis A1. So oriented, the magnetic fields of the diametrically magnetized magnets 210 are aligned with the magnetic field of a diametrically magnetized disk-shaped positioning magnet, such as a headpiece magnet 810 (discussed below with reference to FIG. 55). It should also be noted here that the magnetic field of the positioning magnet will not be strong enough to cause the magnets 210 to rotate out of the illustrated at rest N-S orientation. Although the frame 208 will rotate as necessary, the magnets 210 will remain in the N-S orientation illustrated in FIG. 32 and will continue to function as a magnetic unit in the presence of a headpiece magnet.

The exemplary case 202 is not limited to any particular configuration, size or shape. In the illustrated implementation, the case 202 is a two-part structure that includes the base 204 and the cover 206 which are secured to one another in such a manner that a hermetic seal is formed between the cover and the base. Suitable techniques for securing the cover 206 to the base 204 include, for example, seam welding with a laser welder. With respect to materials, the case 202 may be formed from biocompatible paramagnetic metals, such as titanium or titanium alloys, and/or biocompatible non-magnetic plastics such as polyether ether ketone (PEEK), low-density polyethylene (LDPE), high-density polyethylene (HDPE), ultra-high-molecular-weight polyethylene (UHMWPE), polytetrafluoroethylene (PTFE) and polyamide. In particular, exemplary metals include commercially pure titanium (e.g., Grade 2) and the titanium alloy Ti-6Al-4V (Grade 5), while exemplary metal thicknesses may range from 0.20 mm to 0.25 mm. With respect to size and shape, the case 202 may have an overall size and shape similar to that of conventional cochlear implant magnets, although such sizing/shaping is not required because the magnet apparatus is not located within the cochlear implant housing 22.

Although the present inventions are not limited to any particular number, there are four elongate diametrically magnetized magnets 210 in the exemplary magnet apparatus 200. Two of the otherwise identical magnets 210 are relatively long and two are relatively short in order to efficiently utilize the available volume within the case 202. The exemplary magnets 210 are circular in a cross-section, have rounded corners 212, and are located within low friction tubes 214. Suitable materials for the magnets 210 include, but are not limited to, neodymium-boron-iron and samarium-cobalt.

The exemplary magnet frame 208 includes a disk 216 and a magnet receptacle 218 that extends completely through the disk. The magnet receptacle 218 is configured to hold all of the magnets 210 (four in the illustrated embodiment) and includes a relatively long portion and two relatively short portions. Suitable materials for the frame 208, which may be formed by machining or injection molding, include paramagnetic metals, polymers and plastics such as those discussed above in the context of the case 202.

The inner surfaces of the case 202 and/or the surfaces of the frame 208 may be coated with a lubricious layer. The lubricious layer may be in the form of a specific finish of the surface that reduces friction, as compared to an unfinished surface, or may be a coating of a lubricious material such as diamond-like carbon (DLC), titanium nitride (TiN), PTFE, polyethylene glycol (PEG), Parylene, fluorinated ethylene propylene (FEP) and electroless nickel sold under the tradenames Nedox® and Nedox PF™. The DLC coating, for example, may be only 0.5 to 5 microns thick. In those instances where the base 204 and a cover 206 are formed by stamping, the finishing process may occur prior to stamping. Micro-balls, biocompatible oils and lubricating powders may also be added to the interior of the case to reduce friction. In the illustrated implementation, the surfaces of the frame 208 may be coated with a lubricious layer 220 (e.g., DLC), while the inner surfaces of the case 202 do not include a lubricious layer. The lubricious layer 220 reduces friction between the case 202 and frame 208, while the low friction tubes 214 reduce friction between adjacent magnets 210 as well as between the case 202 and the magnets 210.

Figure 33:
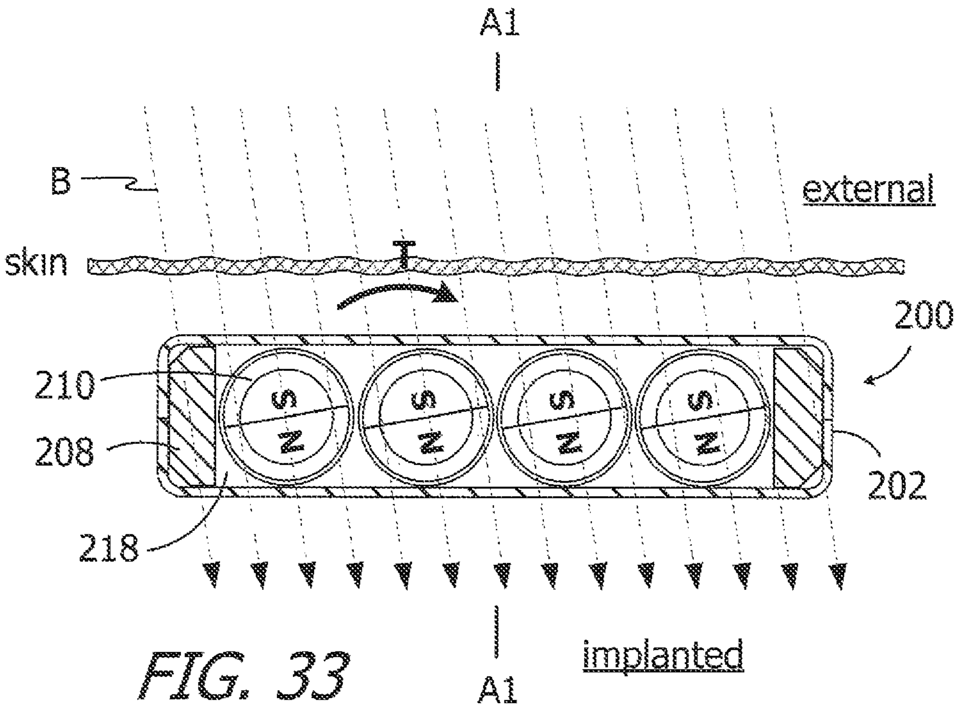
FIG. 33 is a section view similar to FIG. 32 with the implant magnet apparatus in an MRI magnetic field.

Turning to FIG. 33, when exposed to a dominant MRI magnetic field B, the torque T on the magnets 210 will rotate the magnets about their axis A2, thereby aligning the magnetic fields of the magnets 210 with the MRI magnetic field B. The magnet frame 208 will also rotate about axis A1 as necessary to align the magnetic fields of the magnets 210 with the MRI magnetic field B. When the magnet apparatus 200 is removed from the MRI magnetic field B, the magnetic attraction between the magnets 210 will cause the magnets to rotate about axis A2 back to the orientation illustrated in FIG. 32, where they are aligned with one another in the N-S direction and the N-S orientation of the magnets is perpendicular to the central axis A1 of the case 202.

Additional information concerning magnet apparatus 200 and other similar MRI-compatible magnet apparatus may be found in PCT Pat. Pub. No. 2017/105604, which is incorporated herein by reference in its entirety.

Figure 34:
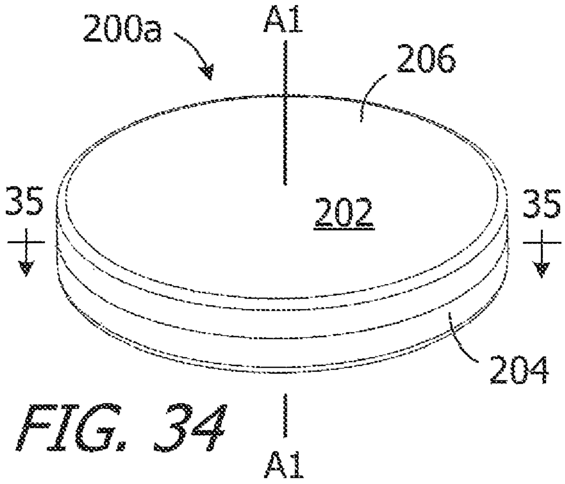
FIG. 34 is a perspective view of an implant magnet apparatus in accordance with one embodiment of a present invention.
Figure 35:
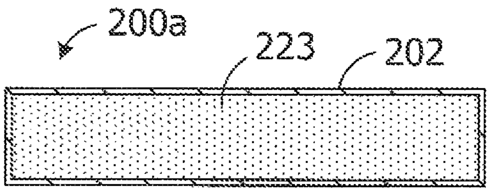
FIG. 35 is a section view take along line 35-35 in FIG. 34.

Another exemplary MRI-compatible magnet apparatus is generally represented by reference numeral 200*a* in FIGS. 34 and 35. The magnet apparatus 200*a* includes a case 202, with base 204 and a cover 206, and magnetic material particles (or "particles") 223 within the internal volume of a case 202. The particles 223 are in contact with one another and are independently and freely rotatable and otherwise movable relative to one another and to the case. The particles 223 are free to move from one X-Y-Z coordinate to another and/or rotate in any direction. For example, some particles 223 may move linearly and/or rotate relative to other particles and relative to the case 202, while the orientation of the case remains the same, when the magnet apparatus 200*a* is exposed to an external magnetic field. Although the present magnetic material particles are not limited to any particular shape, the exemplary magnetic material particles 223 may be spherical or may be non-spherical, polyhedral shapes or at least substantially polyhedral shapes, i.e., multi-sided shapes that are regular or irregular, symmetric or asymmetric, with or without smooth side surfaces, and with or without straight edges, that will permit the particles to rotate relative to one another when loosely packed. Any three-dimensional shapes that permit the movement described above may also be employed. The magnetic material particles 223 may be formed from any suitable magnetic material. Such materials include, but are not limited to, neodymium-iron-boron ("$Nd_2Fe_{14}B$") magnetic material, isotropic neodymium, anisotropic neodymium, samarium-cobalt ("$Sm_2Co_{17}$"). Additional information concerning magnet apparatus 200*a* and other similar MRI-compatible magnet apparatus may be found in PCT Pat. Pub. No. WO2016/190886, which is incorporated herein by reference in its entirety.

Figure 36:
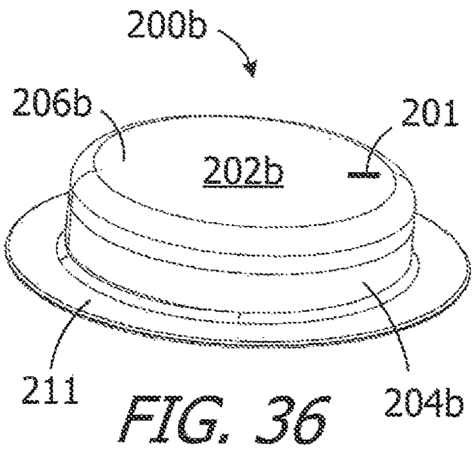
FIG. 36 is a perspective view of a magnet apparatus insert in accordance with one embodiment of a present invention.
Figure 37:
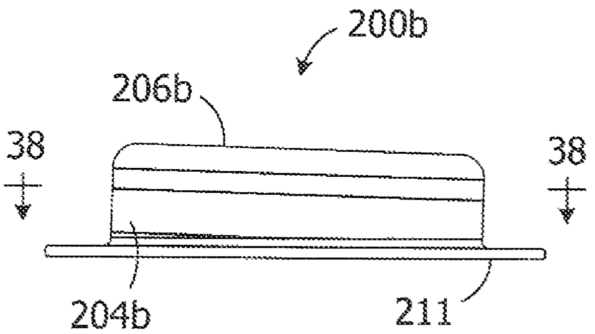
FIG. 37 is a side view of the magnet apparatus insert illustrated in FIG. 36.
Figure 38:
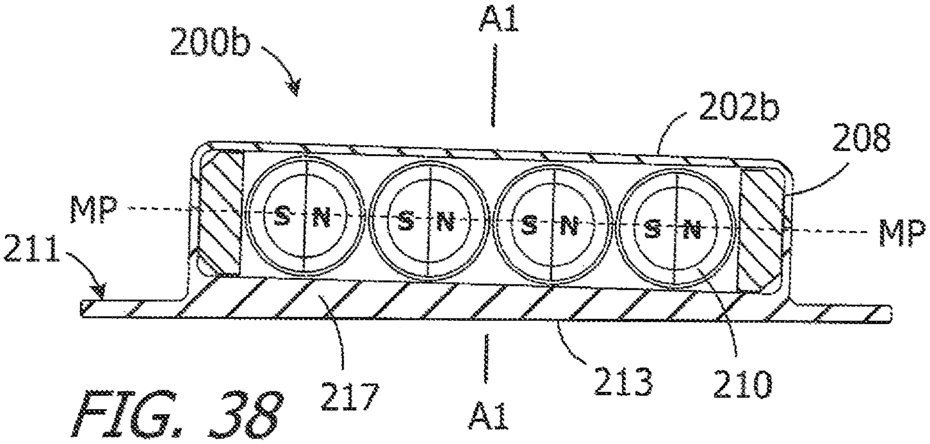
FIG. 38 is a section view taken along line 38-38 in FIG. 37.

Another exemplary MRI-compatible magnet apparatus is generally represented by reference numeral **200*b* in FIGS. 36-38. The magnet apparatus 200*b* is similar to magnet apparatus 200 and similar element are represented by similar reference numerals. For example, the magnet apparatus 200*b* includes a case 202*b*, with base 204*b* and a cover 206*b*, a magnet frame 208, and a plurality of elongate diametrically magnetized magnets 210. The case 202*b* is also disk-shaped and defines a central axis A1, while each of the magnets 210 is freely rotatable relative to the magnet frame 208 about its own longitudinal axis, as is discussed above with reference to FIG. 29. The longitudinal axes of the magnets are parallel to one another and may be perpendicular to the central axis A1 (as shown), or non-perpendicular to the central axis A1. Here, however, the magnet apparatus 200*b*** may be used to form a modified cochlear implant without the use of a housing replacement portion.

The exemplary magnet apparatus **200*b* includes, in addition to the elements described above, a thin disk-shaped apparatus base 211 with a flat bottom surface 213 that defines the bottom surface of the magnet apparatus. The apparatus base 211 has a larger diameter than the case 202*b* and, therefore, forms a flange that extends radially beyond the outer perimeter of the case. As such, a portion of the apparatus base 211 forms a flange that extends radially beyond the case 202*b* and may be used to fix the position of the magnet apparatus 200*b* relative to the associated cochlear implant housing, as is discussed below with reference to FIG. 42**.

Figure 39:
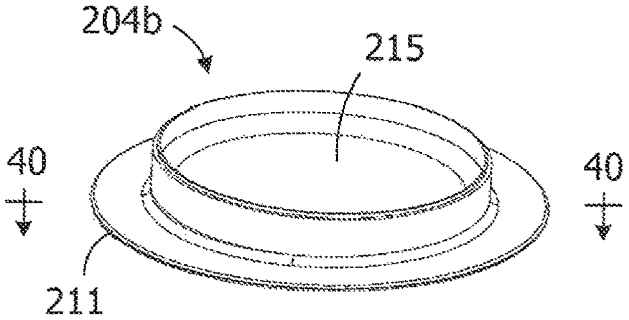
FIG. 39 is a perspective view of a portion of the magnet apparatus insert illustrated in FIG. 36.
Figure 40:
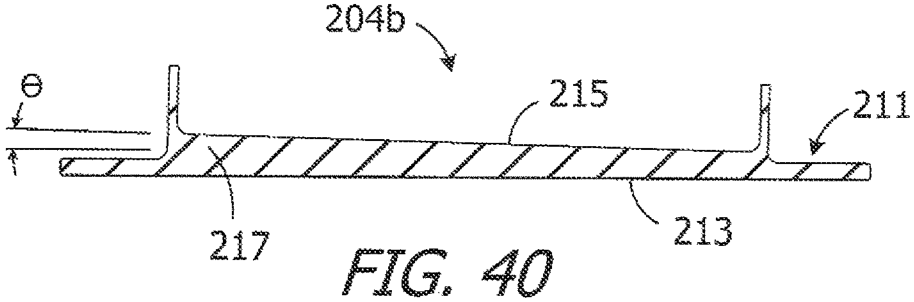
FIG. 40 is a section view of a portion of the magnet apparatus insert illustrated in FIG. 36.

Turning to FIGS. 39 and 40, the case **202*b* in the exemplary magnet apparatus 200*b* may be oriented relative to the apparatus base 211 in such a manner that it is non-parallel to the flat bottom surface 213 (as shown) or in such a manner that it is parallel to the flat bottom surface. In the illustrated implementation, the bottom inner surface 215 (i.e. the surface closest to the apparatus base 211) of the case 202*b* is offset from parallel to the flat bottom surface 213 by an angle Θ of about 1.0 to 5.0 degrees, as is the top outer surface of the case (and magnet apparatus), due to the presence of the angled wedge 217. The magnets 110 also define a magnet plane MP that is offset from parallel to the flat bottom surface 213 by the same angle. The angular offset is especially useful in those instance where the implant antenna portion 26*b*' is slightly angled, as is discussed below with reference to FIG. 42**.

In the illustrated implementation, the case base **204*b* and the apparatus base 211 together define an integral, one-piece unit. The case base 204*b* and the apparatus base 211 may be machined from a common blank or metal injection molded in a common mold. In other implementations, a ring formed from PEEK or a liquid-crystal polymer may be press fitted, clipped or over-molded onto the case base 204*b*. Alternatively, a disk with a wedge similar to that illustrated in FIG. 40 may be secured to the bottom of the case base 204*b***.

Figure 41:
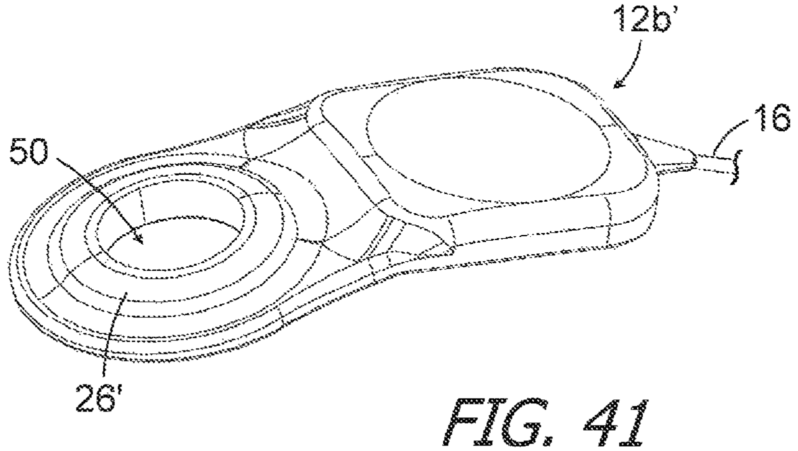
FIG. 41 is a perspective view of an aspect of a cochlear implant modification process in accordance with one embodiment of a present invention.
Figure 42:
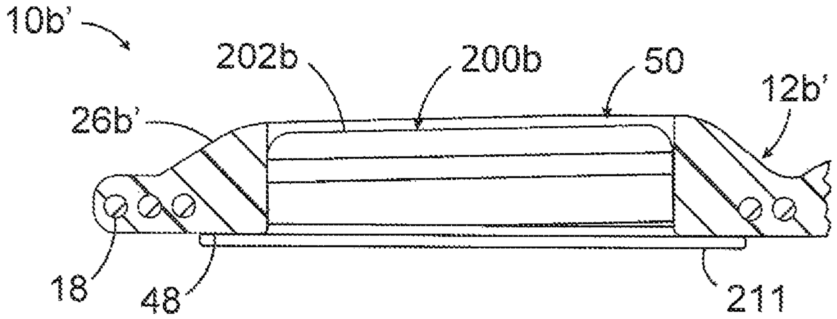
FIG. 42 is a partial section view of a modified cochlear implant including the magnet apparatus insert illustrated in FIG. 36.

Turning to FIGS. 41 and 42, the exemplary magnet apparatus may be used in conjunction with a partial housing **12*b*' formed from a cochlear implant that is essentially identical to implant 10 (FIG. 4) but for the angle of the antenna portion 26*b*'. The magnet apparatus 200*b* may be inserted through the bottom of the aperture 50, i.e. the portion of the aperture that is closest to bone. The flange portion of the apparatus base 211 that extends beyond the outer perimeter of the case 202*b* engages the bottom wall 48, thereby fixing the position of the magnet apparatus 200*b* relative to the partial housing 12*b*'. The orientation of the magnet apparatus 200*b* should also be such that the top surfaces of the implant antenna portion 26*b*' and the case 202*b* slope in the same direction. To that end, indicia 201 (FIG. 36) that identifies the low end of the case 202*b* may be provided on the top surface of the case 202*b* so that the surgeon can properly align the magnet apparatus 200*b* with the implant antenna portion 26*b*'**.

In some implementations, the top and side exterior surfaces of the case **202*b* may be enclosed in a thin PTFE shell, or coated with a lubricious material (such as Serene® coating from Surmodics Inc.), to facilitate passage of the case 202*b* into the aperture 50**. The shell or coating materials may also have anti-microbial properties, in some instances, to reduce the likelihood of biofilm formation and/or infection.

As alluded to above, in other implementations, a flange that extends radially beyond the outer perimeter of the case may be employed in magnet apparatus where the magnet case is parallel to the bottom surface of the flange. Here too, the flange may be used to fix the position of the magnet apparatus relative to the associated cochlear implant housing.

Figure 43:
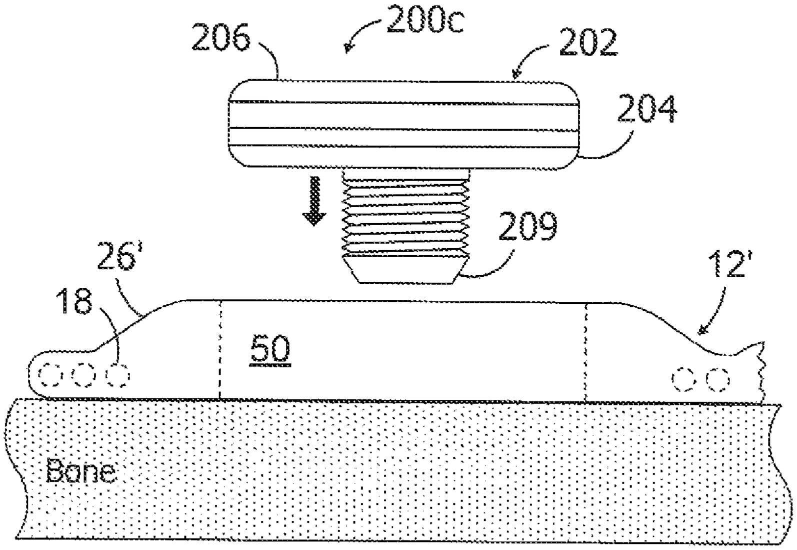
FIG. 43 is a side view of an aspect of a cochlear implant modification process in accordance with one embodiment of a present invention.
Figure 44:
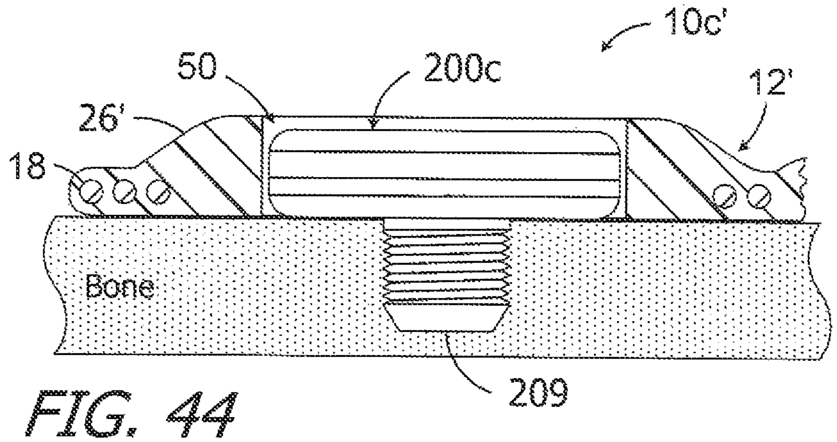
FIG. 44 is a side, partial section view of a modified cochlear implant in accordance with one embodiment of a present invention.
Figure 45:
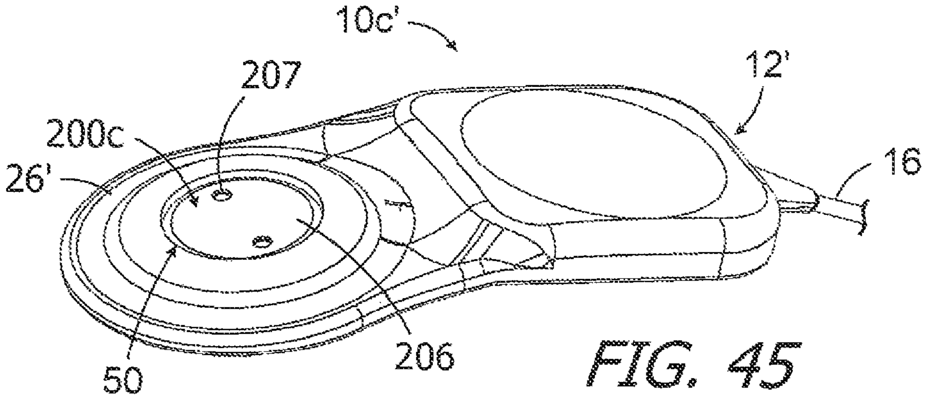
FIG. 45 is a perspective view of a modified cochlear implant in accordance with one embodiment of a present invention.
Figure 46:
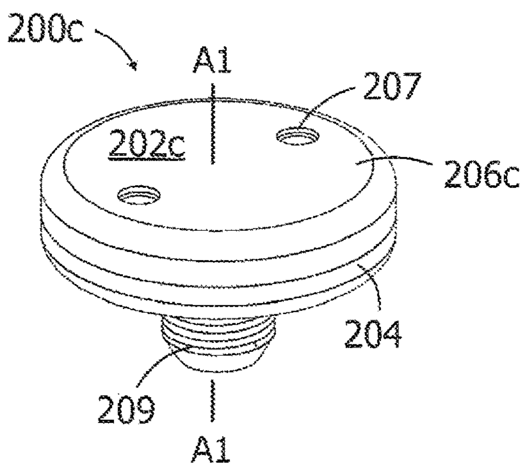
FIG. 46 is a perspective view of a magnet apparatus in accordance with one embodiment of a present invention.
Figure 47:
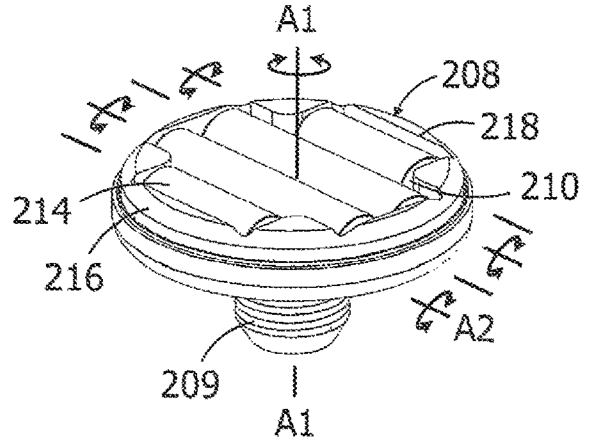
FIG. 47 is a perspective view of a portion of the magnet apparatus illustrated in FIG. 46.
Figure 48:
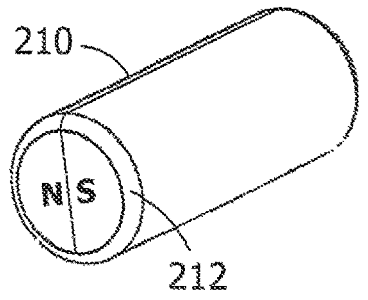
FIG. 48 is a perspective view of a portion of the magnet apparatus illustrated in FIG. 46.
Figure 49:
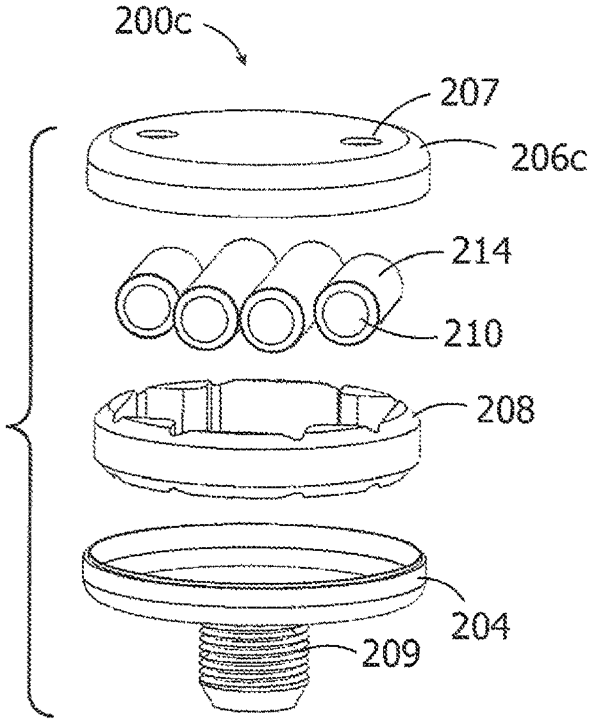
FIG. 49 is an exploded perspective view of the magnet apparatus illustrated in FIG. 46.
Figure 50:
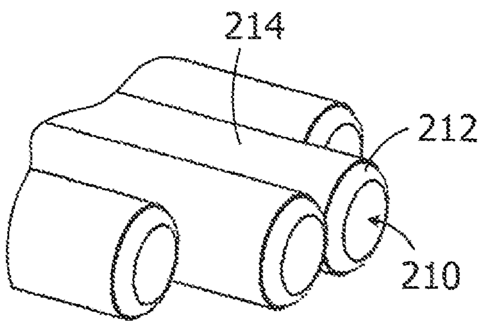
FIG. 50 is a perspective view of a portion of the magnet apparatus illustrated in FIG. 46.
Figure 51:
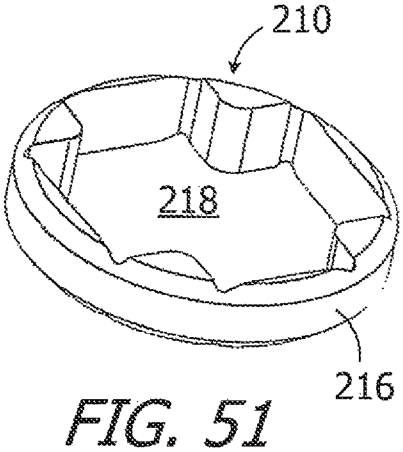
FIG. 51 is a perspective view of a portion of the magnet apparatus illustrated in FIG. 46.
Figure 52:
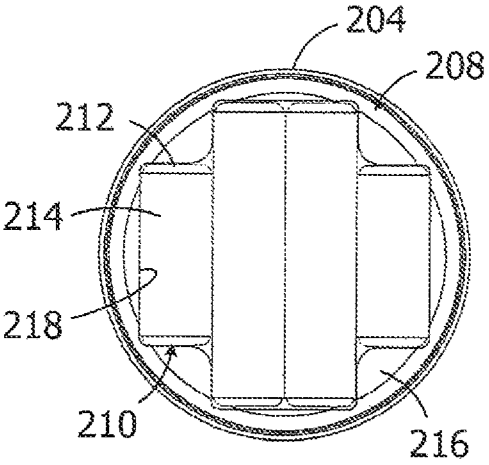
FIG. 52 is a top view of a portion of the magnet apparatus illustrated in FIG. 46.

Turning to FIGS. 43-45, another example of a magnet apparatus that may be inserted into the aperture 50 of the partial housing 12' to form a modified cochlear implant **10*c*' is the exemplary MRI-compatible magnet apparatus 200*c*. The magnet apparatus 200*c* may also be slightly larger than the magnet pocket 30 and/or larger that the magnet 28** that was in the pocket.

The magnet apparatus **200*c*, which is described in greater detail below with reference to FIGS. 46-52, is substantially similar to magnet apparatus 200 and includes a disk-shaped case 202*c*, with base 204 and a cover 206*c* (which is slightly thicker than cover 206), and a bone screw 209 (or other bone anchor) that is permanently secured to the case base 204, such as by welding. As used here, the phrase "permanently secured" means that, once connected, the bone screw will remain on the case 202*c* under normal use conditions, and cannot be removed from the case without destruction of the bone screw, the case and/or the instrumentality that secures the two to one another. The size of the case 202*c* (e.g., the diameter and the thickness) is slightly less that of the aperture 50. In other implementations, the thickness of the case 202*c* may be the same as, or slightly greater than, the thickness of the aperture 50 and/or the diameter of the case may be the same as the diameter of the aperture. Suitable materials for the case 202*c*** are described above.

After the magnet apparatus **200*c* has been inserted into the aperture 50 (FIG. 43), the magnet apparatus may be rotated to drive the bone screw 209 into the bone (FIGS. 44 and 45). To that end, the case cover 206*c* may include a pair of circular indentations 207 or other structure(s) that may be engaged by a tool that is capable of rotating the magnet apparatus 200*c*. One suitable tool is a torque limiting screwdriver, which will prevent damage to the magnet apparatus and/or bone that could result from the application of excessive torque. It should also be noted that the magnet apparatus 200*c* is not secured to the partial housing 12' or any other part of remainder of the modified cochlear implant 10*c*'. As such, some or all of the modified cochlear implant 10*c*' may be explanted without disturbing the bone-anchored magnet apparatus 200*c***.

Turning to FIGS. 46-49, and in addition to the above-described case **202*c* and bone screw 209, the exemplary magnet apparatus 200*c* includes a magnet frame 208 and a plurality of elongate diametrically magnetized magnets 210** within the frame that are cylindrical in shape and that define a N-S direction. The exemplary case 202*c* and bone screw 209 define a central axis A1, which is also the central axis of the magnet frame 208, and the magnet frame is freely rotatable relative to the case about the central axis A1 over 360°. The magnets 210 rotate with the magnet frame 208 about the central axis A1. In other words, the bone screw 209 defines the axis about which the magnet frame 208 and magnets 210 rotate. Each magnet 210 is also freely rotatable relative to the magnet frame 208 about its own longitudinal axis A2 over 360°. In the illustrated implementation, the longitudinal axes A2 are parallel to one another and are perpendicular to the central axis A1. The axes A2 may be non-perpendicular to the central axis A1 in other implementations.

Given the ability of each magnet 210 to freely rotate about its longitudinal axis A2, the magnets align with one another in the N-S direction in the absence of a relatively strong external magnetic field (e.g., the MRI magnetic field discussed below with reference to FIG. 56), and the at rest N-S orientation of the magnets will be perpendicular to the central axis A1 (see FIG. 55). So oriented, the magnetic fields of the diametrically magnetized magnets 210 will be aligned with the magnetic field of a diametrically magnetized disk-shaped positioning magnet, such as the headpiece positioning magnet discussed below with reference to FIG. 55. It should also be noted here that the magnetic field of the positioning magnet will not be strong enough to cause the magnets 210 to rotate out of the illustrated at rest N-S orientation. Although the frame 208 will rotate as necessary due to the magnetic field of the headpiece magnet, the magnets 210 will remain in the N-S orientation illustrated in FIG. 55 and will continue to function as a magnetic unit in the presence of a headpiece magnet.

The exemplary case 202*c* is not limited to any particular configuration, size or shape. In the illustrated implementation, the case 202*c* is a two-part structure that includes the base 204 and the cover 206*c* which are secured to one another in such a manner that a hermetic seal is formed between the cover and the base. Suitable case materials and techniques for securing the cover 206*c* to the base 204 are described above. The exemplary metal thicknesses in this implementation may range from 0.20 mm to 0.25 mm except for the circular portion of the cover 206*c*, which is slightly thicker (e.g., from 0.4 mm to 0.6 mm) to accommodate the indentations 207. With respect to size, the diameter may range from 9 mm to 16 mm and the thickness may range from 1.5 mm to 4.0 mm. The diameter of the case 202*c* is 12.65 mm, and the thickness is 3.35 mm, in the illustrated embodiment.

The exemplary bone screw 209 is about 2.5 to 4.0 mm in length and about 1.5 to 2.5 mm in diameter. The length and diameter may, however, be altered to suite particular skull thicknesses, such as those of pediatric patients. Also, the present inventions are not limited to the illustrated bone screw and other types of bone anchors may be employed. By way of example, but not limitation, tri-start (or other multi-start) bone screws, bone screws with coatings or other features that promote osseointegration, expandable bone anchors, and any other suitable cranial bone anchors may be secured to the case base 204 in place of the exemplary bone screw 209.

Figure 53:
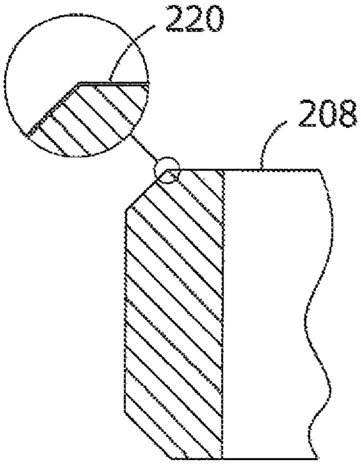
FIG. 53 is a section view of a portion of a magnet apparatus in accordance with one embodiment of a present invention.
Figure 54:
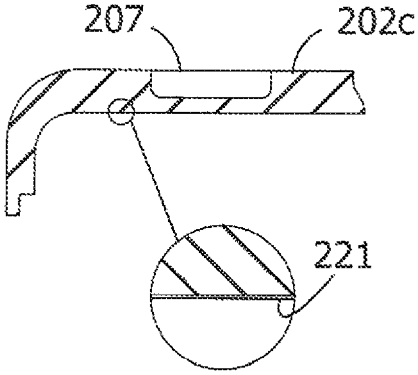
FIG. 54 is a section view of a portion of a magnet apparatus in accordance with one embodiment of a present invention.

Turning to FIGS. 48-52, there are four elongate diametrically magnetized magnets 210 in the exemplary magnet apparatus 200*c*. Two of the otherwise identical magnets 210 are relatively long and two are relatively short in order to efficiently utilize the available volume within the case 202*c*. As discussed above with reference to FIGS. 30-31, the exemplary magnets 210 are circular in a cross-section, have rounded corners 212, and are located within low friction tubes 214. The exemplary magnet frame 208 includes a disk 216 and a magnet receptacle 218 that extends completely through the disk. The magnet receptacle 218 is configured to hold all of the magnets 210 (four in the illustrated embodiment) and includes a relatively long portion and two relatively short portions. Suitable materials for the frame 208 and the magnets 210 are discussed above. The inner surfaces of the case 202*c* and/or the surfaces of the frame 208 may be coated with lubricious layers 220 and 221 (FIGS. 53 and 54), formed by the surfaces and materials discussed above, to reduce friction.

Figure 55:
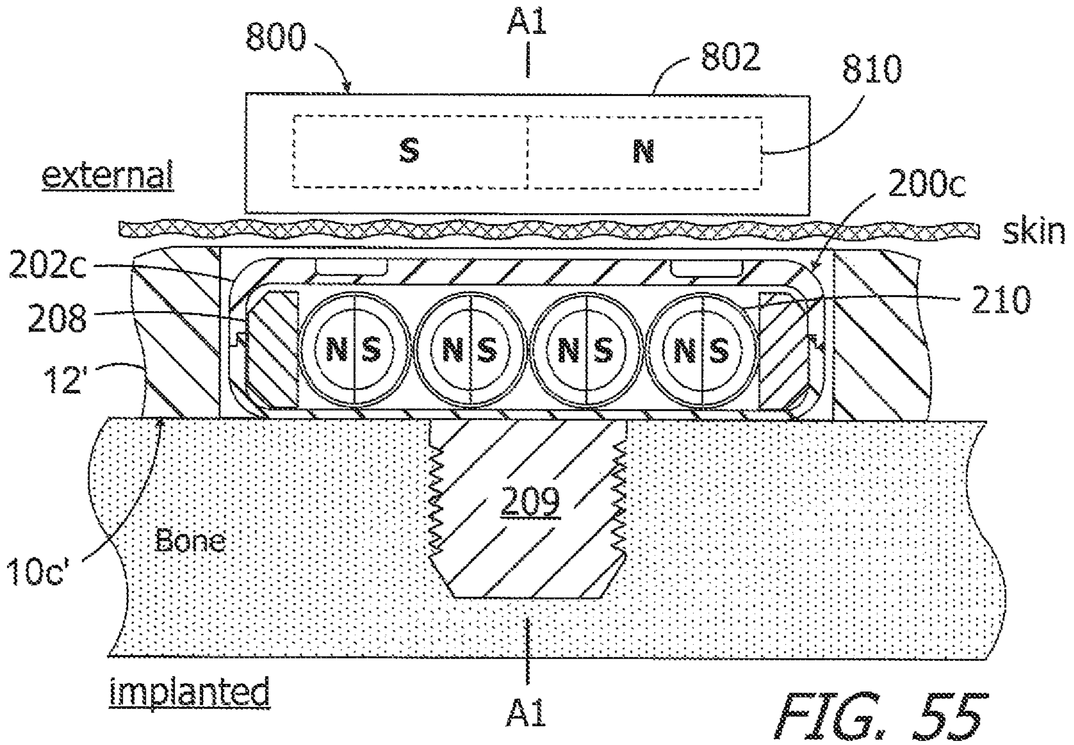
FIG. 55 is a partial section view of a cochlear implant and headpiece in accordance with one embodiment of a present invention.
Figure 56:
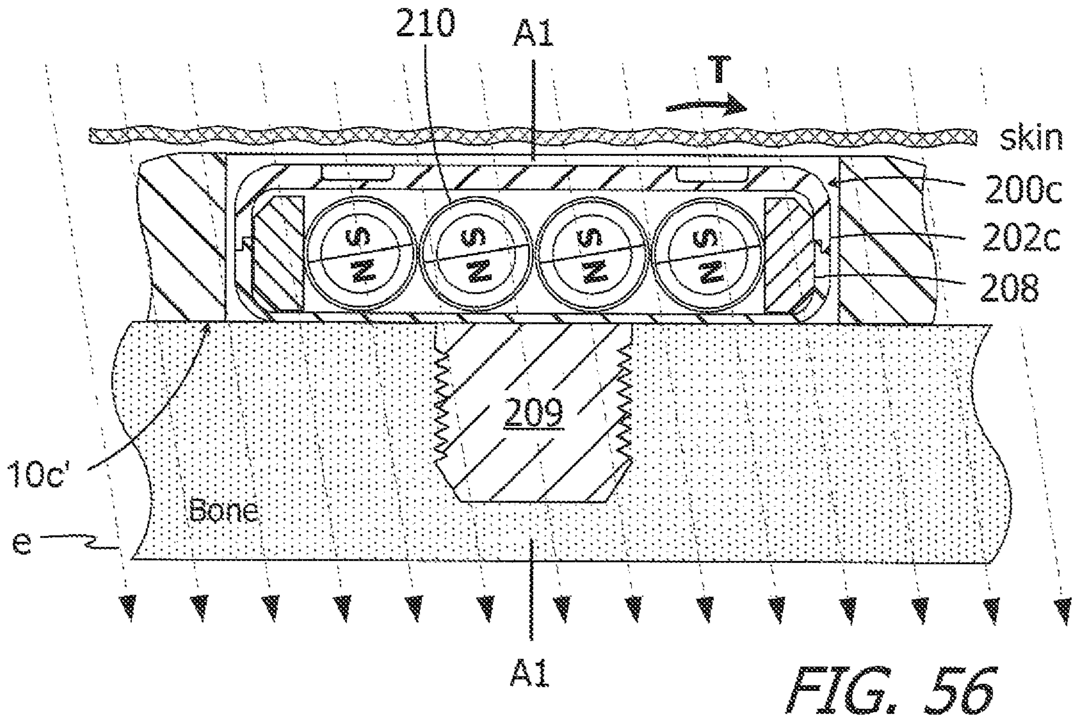
FIG. 56 is a section view similar to FIG. 55 with the cochlear implant in an MRI magnetic field.

Turning to FIG. 55, the modified cochlear implant 10*c*' may be used in conjunction with an external device such as a headpiece 800 (described in greater detail below with reference to FIG. 153). The headpiece 800 includes, among other things, a housing 802 and a diametrically magnetized disk-shaped positioning magnet 810 that is not rotatable relative to the housing. As noted above, the magnetic fields of the diametrically magnetized magnets 210 will align with the magnetic field of the headpiece magnet 810. The magnetic field of the headpiece magnet 810 does not cause the magnets 210 to rotate out of their illustrated at rest N-S orientation, although the frame 208 will rotate as necessary due to the magnetic field of the positioning magnet.

When exposed to a dominant MRI magnetic field B (FIG. 56), the torque T on the magnets 210 will rotate the magnets about their axis A2, thereby aligning the magnetic fields of the magnets with the MRI magnetic field B. The magnet frame 208 will also rotate about axis A1 as necessary to align the magnetic fields of the magnets 210 with the MRI magnetic field B. In other words, although the bone screw 209 will prevent the case 202*c* from moving, the freedom to rotate about axis A1 and axes A2 allows the magnets to move into alignment with the dominant magnetic field. When the magnet apparatus 200*c* is removed from the MRI magnetic field B, the magnetic attraction between the magnets 210 will cause the magnets to rotate about their axis A2 back to the orientation illustrated in FIG. 55, where they are aligned with one another in the N-S direction and the N-S orientation of the magnets is perpendicular to the central axis A1 of the case 202*c*.

Figure 57:
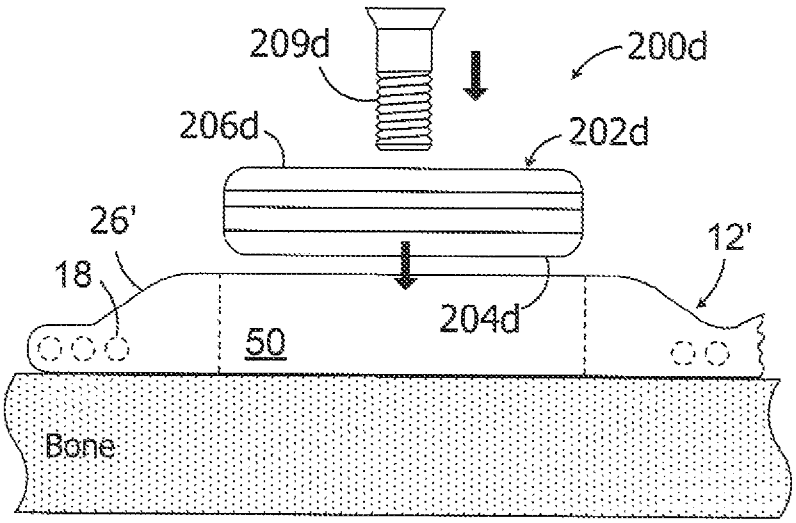
FIG. 57 is a side view of an aspect of a cochlear implant modification process in accordance with one embodiment of a present invention.
Figure 58:
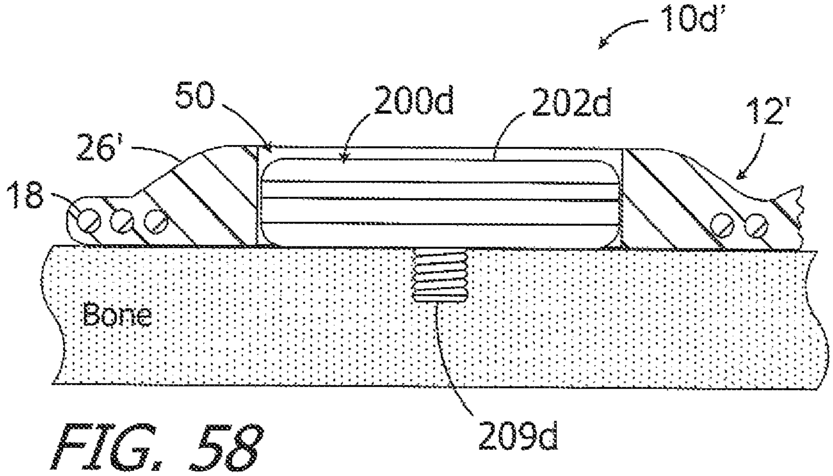
FIG. 58 is a side, partial section view of a modified cochlear implant in accordance with one embodiment of a present invention.
Figure 59:
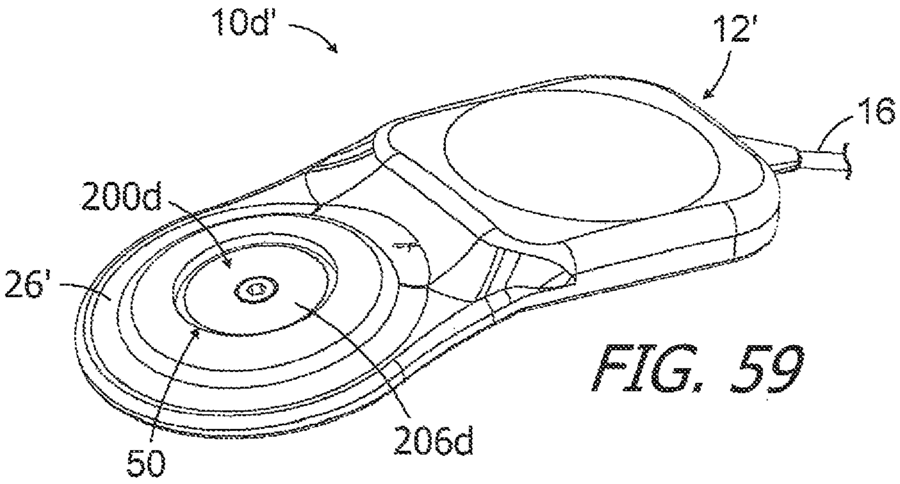
FIG. 59 is a perspective view of a modified cochlear implant in accordance with one embodiment of a present invention.
Figure 60:
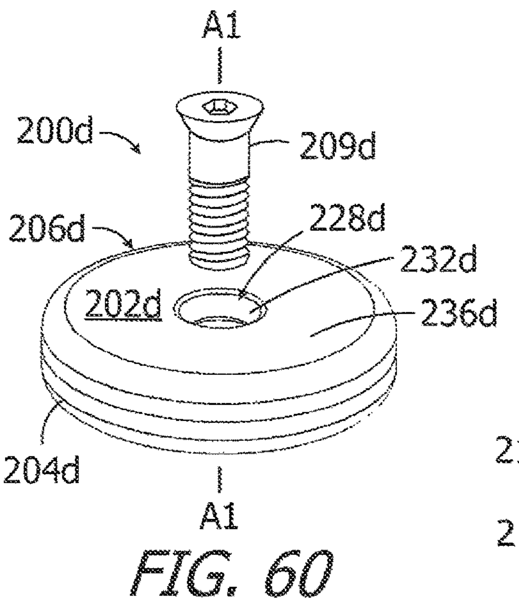
FIG. 60 is an exploded perspective view of a magnet apparatus in accordance with one embodiment of a present invention.
Figure 61:
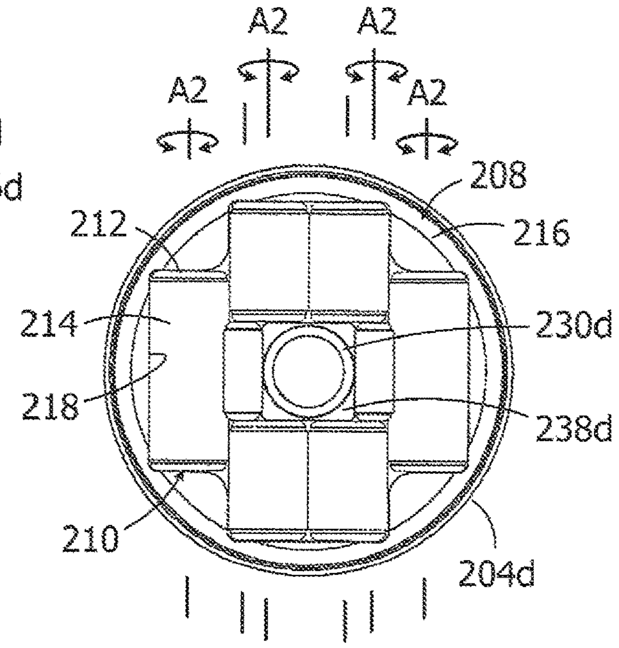
FIG. 61 is a top view of a portion of the magnet apparatus illustrated in FIG. 60.
Figure 62:
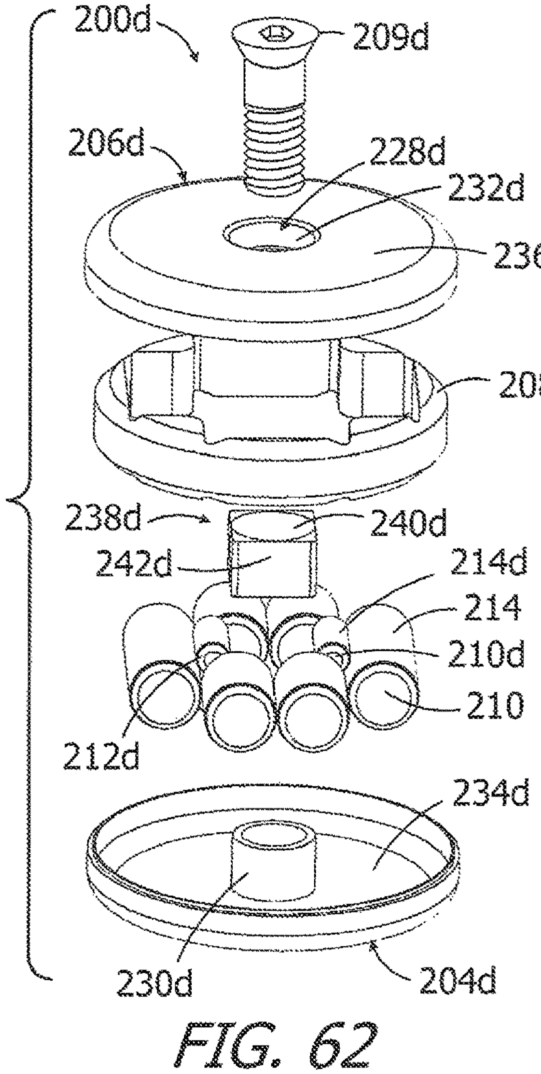
FIG. 62 is an exploded perspective view of the magnet apparatus illustrated in FIG. 60.
Figure 63:
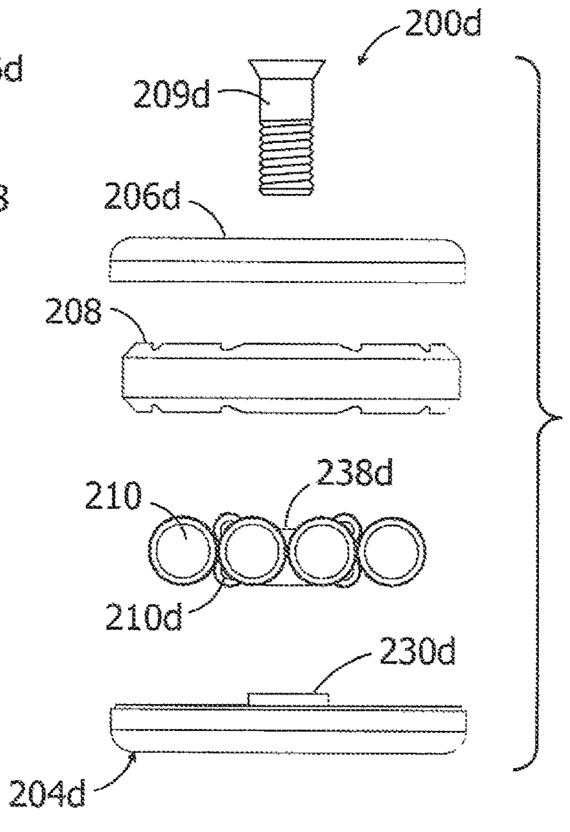
FIG. 63 is an exploded view of the magnet apparatus illustrated in FIG. 60.

Another exemplary magnet apparatus is generally identified by reference numeral 200*d* in FIGS. 57-59. The magnet apparatus 200*d* is similar to magnet apparatus 200*c* and similar elements are represented by similar reference numerals. For example, the exemplary magnet apparatus 200*d* includes a case 202*d*, with a base 204*d* and a cover 206*d*, a bone screw 209*d* (or other anchor). The case 202*d* may be formed from the same materials as the case 202, and may have the same overall dimensions, in some embodiments. The magnet apparatus 200*d* also includes the rotatable frame and rotatable magnets described below with reference to FIGS. 60-63. The size of the case 202*d* (e.g., the diameter and the thickness) is slightly less that of the aperture 50. In other implementations, the thickness of the case 202*d* may be the same as, or slightly greater than, the thickness of the aperture 50 and/or the diameter of the case may be the same as the diameter of the aperture.

Here, however, the bone screw 209*d* is not secured to the case base 204*d*. The case 202*d* and rotatable magnets are instead configured to permit passage of the bone screw 209*d* through the case. The case 202*d* (and components therein) may be inserted into the aperture 50, and the bone screw 209*d* may be inserted through the case (FIG. 57) before or after the case has been inserted into the aperture. The bone screw 209*d* may then be driven into the bone (FIGS. 58 and 59) until the head of the bone screw reaches a corresponding mating surface on the case 202*d*, thereby anchoring the magnet apparatus 200*d* to the skull and forming the modified cochlear implant 10*d*'. Here too, the magnet apparatus 200*d* is not secured to the partial housing 12' or any other part of remainder of the modified cochlear implant 10*d'*.

Turning to FIGS. 60-63, the exemplary case 202*d* includes a central aperture 228*d* that extends completely through the case to accommodate the bone screw 209*d*. The exemplary central aperture 228*d* is a countersunk aperture that is defined by a central boss 230*d* and a tapered abutment 232*d*. The central boss 230*d* is part of the case base 204*d* and extends upwardly (in the illustrated orientation) from an end wall 234*d*, while the tapered abutment 232*d* is part of the case cover 206*d* and extends downwardly from an end wall 236*d* to the central boss. The exemplary bone screw 209*d* is a flat-head screw configured for use with the countersunk central aperture 228*d*.

The exemplary bone screw 209*d* may be about 5.0 to 8.0 mm in length and about 1.0 to 2.0 mm in diameter. The length and diameter may, however, be altered to suite particular skull thicknesses, such as those of pediatric patients. Also, the present inventions are not limited to the illustrated bone screw and other types of bone anchors may be employed. By way of example, but not limitation, tri-start (or other multi-start) bone screws, bone screws with coatings or other features that promote osseointegration, expandable bone anchors, and any other suitable cranial bone anchors may be inserted through the case 202*d* in place of the exemplary bone screw 209*d*.

Figure 64:
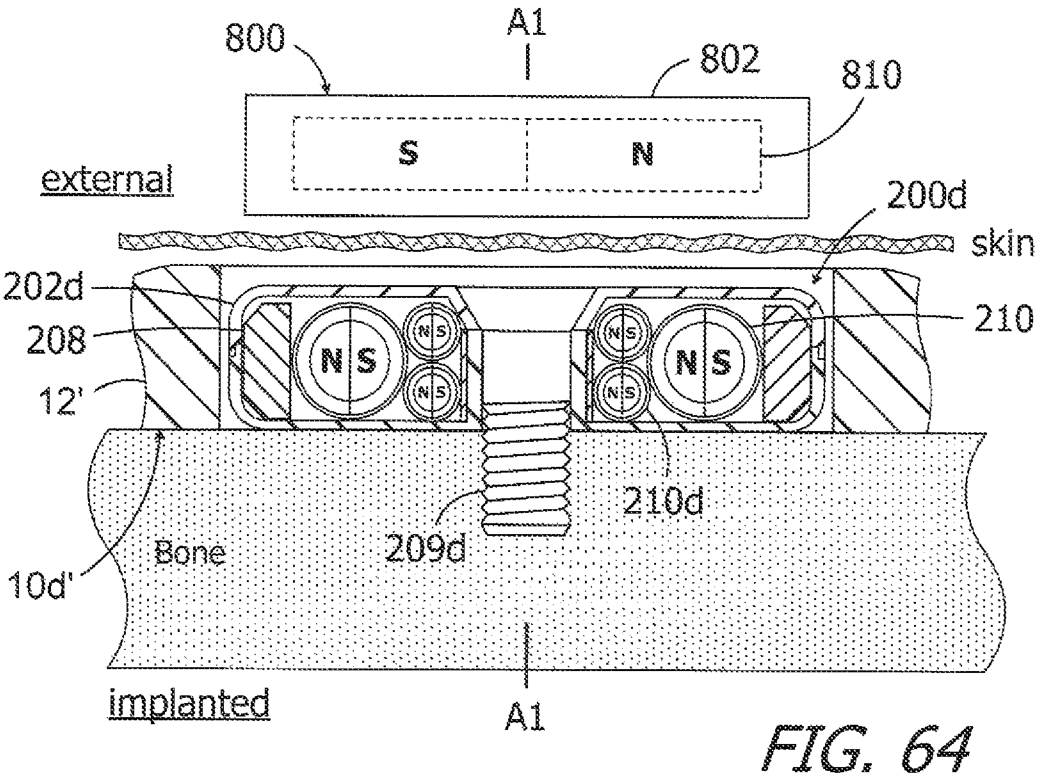
FIG. 64 is a partial section view of a cochlear implant and headpiece in accordance with one embodiment of a present invention.

In addition to the above-described case 202*d* and bone screw 209*d*, the exemplary magnet apparatus 200*d* includes a magnet frame 208 and first and second pluralities of elongate diametrically magnetized magnets 210 and 210*d* within the frame. The magnet frame 208 is freely rotatable relative to the case 202*d* over 360° about the central axis A1 defined by the case 202*d*, the bone screw 209*d* and the frame. The magnets 210 and 210*d* rotate with the magnet frame 208 about the central axis A1. As such, the bone screw 209*d* defines the axis about which the magnet frame 208 and magnets 210 and 210*d* rotate. Each magnet 210 and 210*d* is also freely rotatable relative to the magnet frame 208 about its own longitudinal axis A2 over 360°. In the illustrated implementation, the longitudinal axes A2 are parallel to one another and are perpendicular to the central axis A1. The axes A2 may be non-perpendicular to the central axis A1 in other implementations. Given the ability of each magnet 210 and 210*d* to freely rotate about its longitudinal axis A2, the magnets align with one another in the N-S direction in the absence of a relatively strong external magnetic field and the at rest N-S orientation of the magnets will be perpendicular to the central axis A1, as is shown in FIG. 64. The at rest orientation of the magnets 210*d* is also the result of the dominant magnetic fields of the larger magnets 210. In at least some implementations, the diameter of the larger magnets 210 will be 50 to 55% greater than that of the magnets 210*d*.

The magnets 210 and 210*d* are each cylindrical and define a N-S direction. Like the magnets 210, the magnets 210*d* have rounded corners 212*d*, and are located within low friction tubes 214*a*. The lengths and diameters of the magnets 210 and 210*d* may be selected in a manner that efficiently utilizes the available volume within the case 202*d* given the presence of the central boss 230*d* and tapered abutment 232*d*. To that end, in the illustrated implementation, there are six otherwise identical magnets 210, two of which are relatively long and four of which are relatively short. There are four identical magnets 210*d*. The lengths and diameters of the magnets 210*d* are less than the lengths and diameters of the magnets 210, which allows the magnets 210*d* to fill in gaps within the internal volume of the case 202*d*.

An alignment member 238*d* may be used to ensure that the magnets 210*d* remain in their illustrated locations with their axes A2 parallel to one another and to the axes A2 of the magnets 210. The exemplary alignment member 238*d*, which is rotatable relative to the central boss 230*d*, is block-shaped and includes a central aperture 240*d* for the central boss and side surfaces 242*d* that abut adjacent magnets 210 and 210*d*. Suitable materials for the alignment member 238*d* include, but are not limited to, PEEK and titanium.

Turning to FIG. 64, the modified cochlear implant 10*d*' may be used in conjunction with an external device such as aforementioned the headpiece 800 with the diametrically magnetized disk-shaped positioning magnet 810. The magnetic fields of the diametrically magnetized magnets 210 and 210*d* are aligned with the magnetic field of a diametrically magnetized disk-shaped positioning magnet 810. The magnetic field of the positioning magnet 810 does not cause the magnets 210 and 210*d* to rotate out of their illustrated at rest N-S orientations, although the frame 208 will rotate as necessary due to the magnetic field of the positioning magnet.

Figure 65:
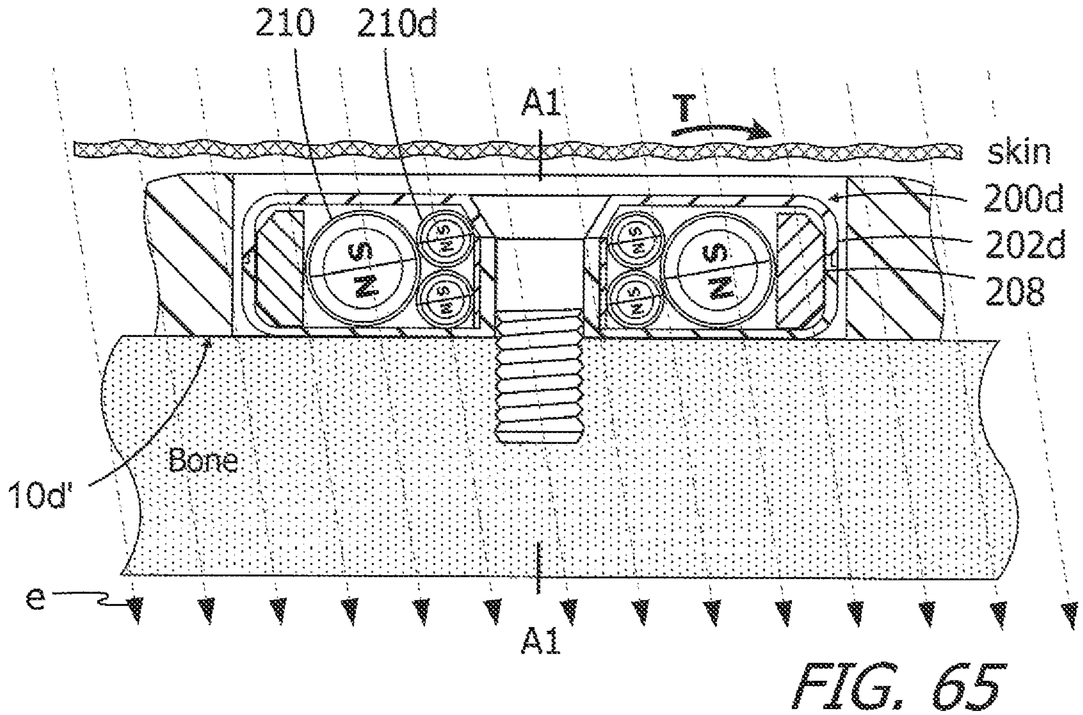
FIG. 65 is a partial section view similar to FIG. 64 with the cochlear implant in an MRI magnetic field.

When exposed to a dominant MRI magnetic field B (FIG. 65), the torque T on the magnets 210 and 210*d* will rotate the magnets about their axis A2, thereby aligning the magnetic fields of the magnets with the MRI magnetic field B. The magnet frame 208 will also rotate about axis A1 as necessary to align the magnetic fields of the magnets 210 and 210*d* with the MRI magnetic field B. Here too, although the bone screw 209*d* will prevent the case 202*d* from moving, the freedom to rotate about axis A1 and axes A2 allows the magnets 210 and 210*d* to move into alignment with the dominant magnetic field. When the magnet apparatus 200*d* is removed from the MRI magnetic field B, the magnetic attraction between the magnets 210 and 210*d*, as well as the dominance of the magnetic field of the larger magnets 210, will cause each magnet to rotate about its axis A2 back to the orientation illustrated in FIG. 64, where they are aligned with one another in the N-S direction and the N-S orientation of the magnets is perpendicular to the central axis A1 of the case 202*d*.

Figure 66:
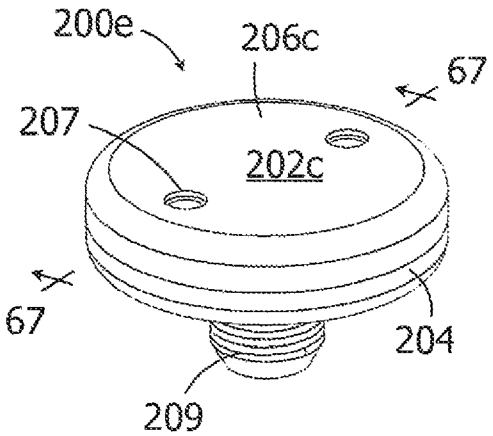
FIG. 66 is a perspective view of a magnet apparatus in accordance with one embodiment of a present invention.
Figure 67:
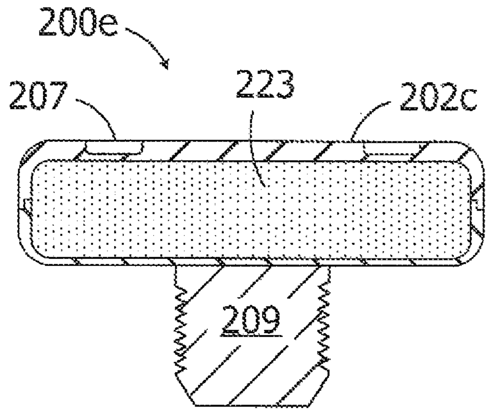
FIG. 67 is a section view taken along line 67-67 in FIG. 66.

Another exemplary MRI-compatible magnet apparatus is generally represented by reference numeral 200*e* in FIGS. 66 and 67. The magnet apparatus 200*e* includes the case 202*c*, with the base 204 and a cover 206*c*, a bone screw 209 (or other bone anchor) that is permanently secured to the case base, and magnetic material particles (or "particles") 223 within the internal volume of a case 202*c*. The particles 223, which are described in greater detail above with reference to FIGS. 34 and 35, are in contact with one another and are independently and freely rotatable and otherwise movable relative to one another and to the case.

Figure 68:
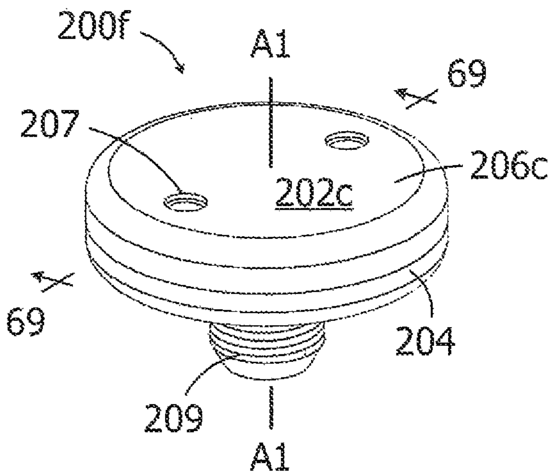
FIG. 68 is a perspective view of a magnet apparatus in accordance with one embodiment of a present invention.
Figure 69:
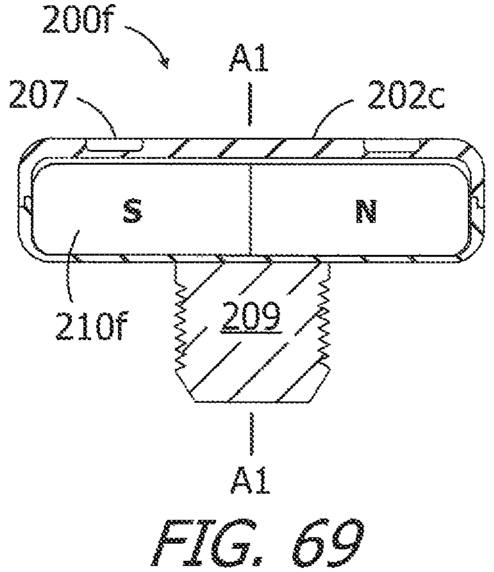
FIG. 69 is a partial section view taken along line 69-69 in FIG. 68.

The exemplary magnet apparatus 200*f* illustrated in FIGS. 68 and 69 includes a case 202*c*, with a base 204 and a cover 206*c*, a bone screw 209 (or other bone anchor) that is permanently secured to the case base 204, and a single diametrically magnetized disk-shaped magnet 210*f* that is rotatable within the case about axis A1. Unlike the MRI-compatible magnet apparatuses described above, the magnet 210*f* is only rotatable about a single axis. As such, the magnet apparatus **200*f*** should not be misaligned with a MRI magnetic field by more than 30°.

Figure 70:
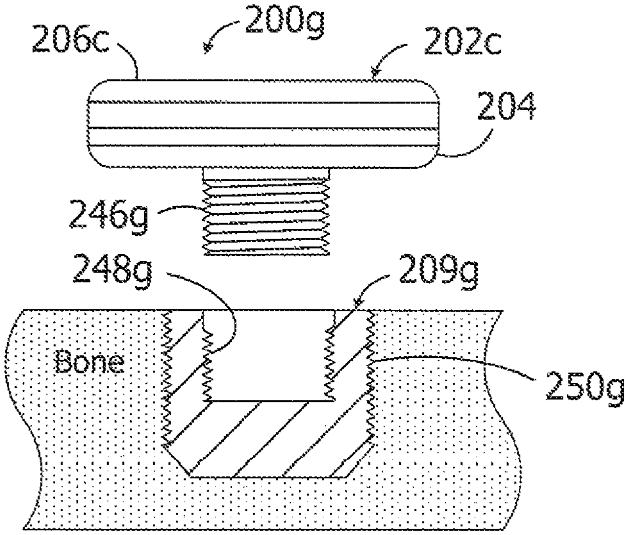
FIG. 70 is an exploded, partial section view of a magnet apparatus in accordance with one embodiment of a present invention.

The present inventors have also determined that some surgeons will prefer to remove a magnet apparatus prior to an MRI procedure, even in those instances where the magnet apparatus is MRI-compatible, and that it would be desirable to remove a bone anchored magnet apparatus and/or to replace a damaged magnet apparatus without drilling out the bone anchors. Accordingly, in still other implementations, the magnet apparatus may be configured in such a manner that the bone anchor will remain in the bone when the remainder of the magnet apparatus is removed. One example of such a magnet apparatus is the magnet apparatus **200*g* illustrated in FIG. 70. The magnet apparatus 200*g* is similar to magnet apparatus 200*c* and similar elements are represented by similar reference numerals. For example, the exemplary magnet apparatus 200*g* includes a case 202*c*, with a base 204 and a cover 206*c*, as well as the magnet frame 208 and plurality of elongate diametrically magnetized magnets 210 described above with reference to FIGS. 47-53. Alternatively, the magnet apparatus 200*g* may include the magnetic material particles 223 described above with reference to FIGS. 34 and 35, or the diametrically magnetized disk-shaped magnet 210*f* described above with reference to FIGS. 68 and 69. The magnet apparatus 200*g* also includes a bone anchor. Here, however, the anchor 209*g* is not permanently secured to the case base 204, and is instead a separate structural element that is attached to the bone independently of the case 202*c*. The anchor 209*g* includes an anchor connector 246*g*, and the case 202*c* is secured to the anchor by way of a corresponding case connector 248*g* that is secured to the case. The anchor 209*g*, once deployed, will be permanently connected to the bone, while the connectors 246*g* and 248*g* form a releasable connection that will remain in place until removal of the case 202*c*** is required.

Although the present inventions are not to any particular connectors, the exemplary connectors **246*g* and 248*g*** are threaded connectors. Other suitable connectors include, but are not limited to, connectors that include a detent and a spring-biased ball, and connectors that include structures which may be rotated in and out of engagement with one another.

With respect to the manner in which the anchor **209*g* is affixed to the bone, the anchor 209*g* may include an outer bone engagement surface 250*g*. The bone engagement surface 250*g*** may be threaded or otherwise configured to screw into bone (including multi-start screw surfaces), may include coatings or other features that promote osseointegration, may be the outer surface of expandable anchor elements, or any other suitable cranial bone anchoring instrumentality. Alternatively, the anchor may be of the type that is affixed to the bone with the Stryker SonicAnchor™ System, which is available from Stryker Trauma GmbH.

In still other implementations, a case and magnet arrangement similar to (or identical to) that described above with reference to FIGS. 57-63 may be employed in conjunction with the bone anchor **209*g***. A case connector (not shown) may be inserted through the aperture in the magnet apparatus case and secured to the bone anchor connector. For example, a flat-head screw configured for use with a countersunk aperture may be inserted through the aperture and secured to the bone anchor.

Figure 71:
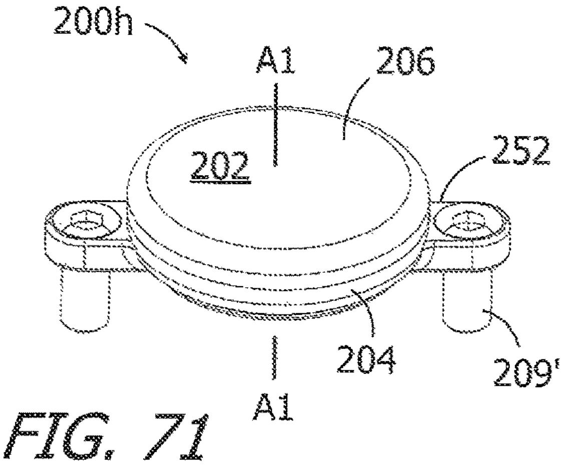
FIG. 71 is a perspective view of a magnet apparatus in accordance with one embodiment of a present invention.
Figure 72:
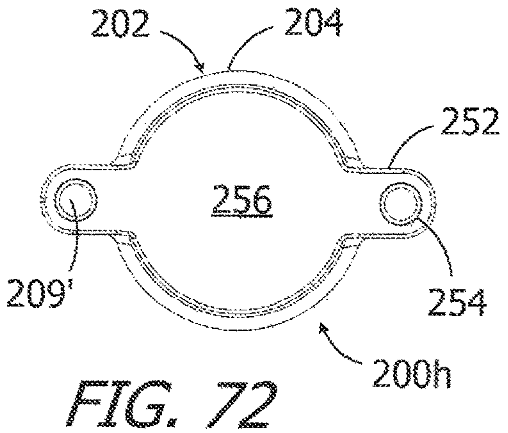
FIG. 72 is a bottom view of the magnet apparatus illustrated in FIG. 71.
Figure 73:
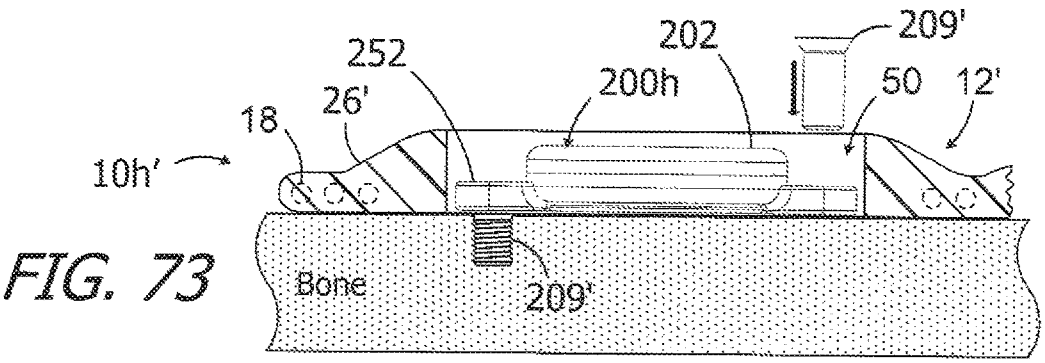
FIG. 73 is an exploded partial section view of an aspect of a cochlear implant modification process in accordance with one embodiment of a present invention.

Another exemplary magnet apparatus is generally identified by reference numeral **200*h* in FIGS. 71-73. The magnet apparatus 200*h* is similar to magnet apparatus 200 and similar elements are represented by similar reference numerals. For example, the exemplary magnet apparatus 200*h* includes a case 202, with a base 204 and a cover 206, as well as the rotatable frame 208 (not shown) and rotatable magnets 210 (not shown) described above. The case 202, rotatable frame 208 and magnets 210 may be formed from the materials described above. Here, however, the magnet apparatus 200*h* may be used to form a modified cochlear implant without the use of a housing replacement portion. Instead, the magnet apparatus 200 may be held in place through the use of bones screws in a manner similar to that described above with reference to FIGS. 43-70**.

Referring more specifically to FIGS. 71 and 72, the magnet apparatus **200*h* also includes two or more protrusions 252 with apertures 254 that are each configured to receive a bone screw 209' (as shown) or other anchor. The protrusions 252 may extend radially or otherwise outwardly from the case base 204 or some other portion of the case 202. The top of the protrusions 252 may be countersunk, counterbored or flat depending on the type of screw or other anchor with which it is intended to be used. The case 202 and protrusions 252 together define an integral, one-piece unit. The case base 204 and the apertures 254 may be machined from a common blank or metal injection molded in a common mold. In other implementations, the protrusions 252 may be separate elements that are welded (e.g., laser welded) or otherwise secured to one another. In the illustrated implementation, the protrusions 252 are carried on a thin disk 256 that may also be welded to or otherwise secured to the bottom of the case base 204**.

The bone screws 209' may be inserted into apertures 254 before or after the magnet apparatus **200*h* has been inserted into the aperture 50. After the magnet apparatus 200*h* has been inserted into the aperture 50, as shown in FIG. 73, the bone screws 209' may be rotated to drive the bone screws into the bone, thereby anchoring the magnet apparatus 200*h* to the skull and forming the modified cochlear implant 10*h*'. Here too, the magnet apparatus 200*h* is not secured to the partial housing 12' or any other part of remainder of the modified cochlear implant 10*h*'**.

Figure 74:
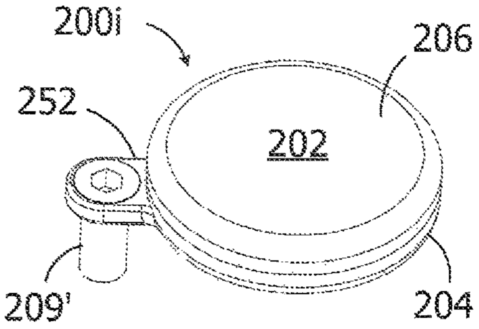
FIG. 74 is a perspective view of a magnet apparatus in accordance with one embodiment of a present invention.
Figure 75:
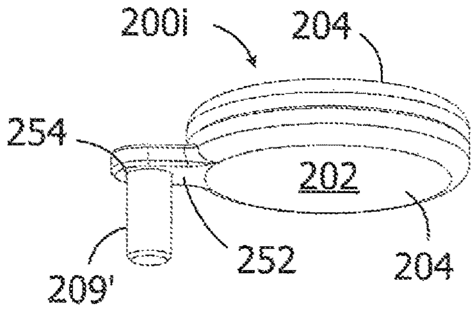
FIG. 75 is a perspective view of the magnet apparatus illustrated in FIG. 74.

Turning to FIGS. 74 and 75, the magnet apparatus **200*i* illustrated therein is substantially similar to magnet apparatus 200*h* and similar elements are represented by similar reference numerals. For example, the exemplary magnet apparatus 200*i* includes a case 202, with a base 204 and a cover 206, as well as the rotatable frame 208 (not shown) and rotatable magnets 210 (not shown) described above. Here, however, a single protrusion 252 with an aperture 254 that is configured to receive a bone screw 209' extends radially or otherwise outwardly from the case 202 (e.g., from the base 204). The case 202 and protrusions 252** may together define an integral unit, or may be separate elements that are secured to one another, as is described above.

Figure 76:
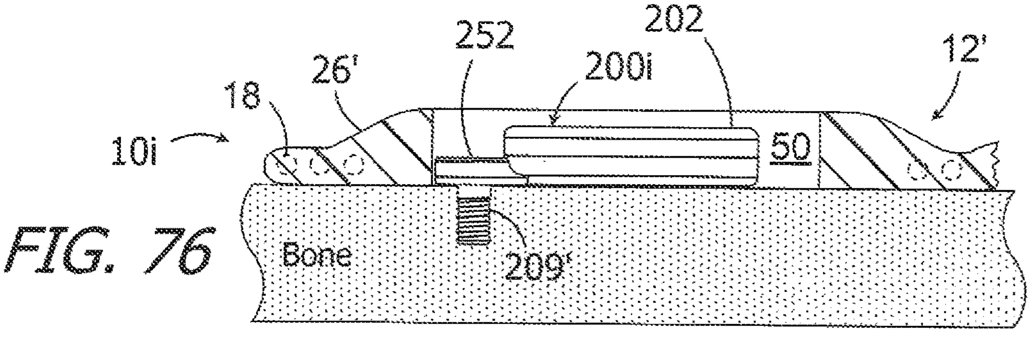
FIG. 76 is a partial section view of a modified cochlear implant in accordance with one embodiment of a present invention.

Referring to FIG. 76, the bone screws 209' may be rotated to drive the bone screw into the bone after the magnet apparatus **200*i* has been inserted into the aperture 50 to anchor the magnet apparatus 200*i* to the skull and form the modified cochlear implant 10*i*. Like the magnet apparatus 200*h*, the magnet apparatus 200*i* is not secured to the partial housing 12' or any other part of remainder of the modified cochlear implant 10*i***.

Figure 77:
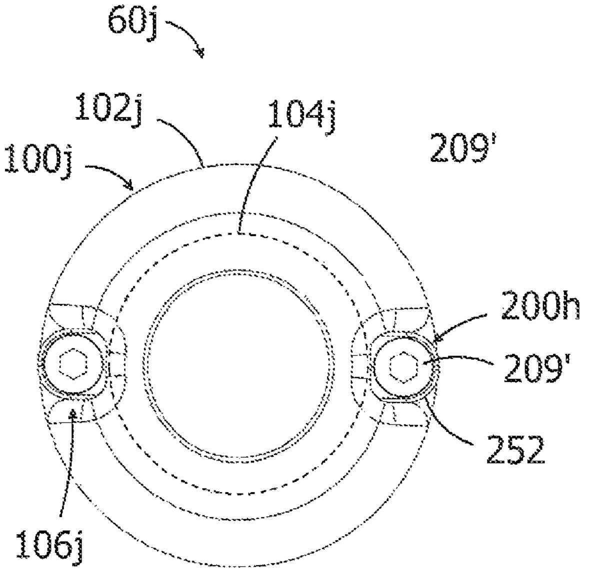
FIG. 77 is a top view of a magnet apparatus in accordance with one embodiment of a present invention.
Figure 78:
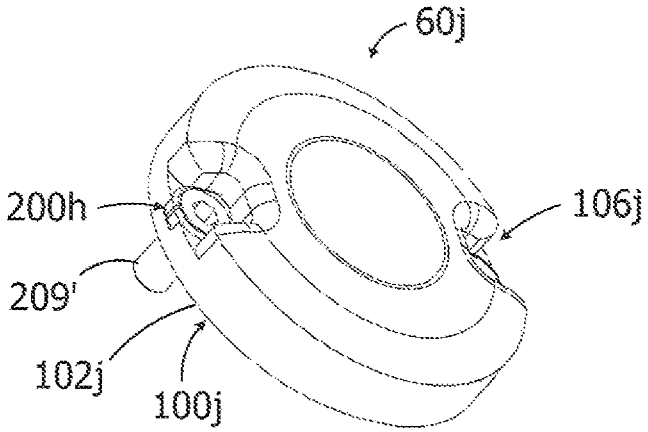
FIG. 78 is a perspective view of the magnet apparatus illustrated in FIG. 77.

The respective overall shapes of the magnet apparatus **200*h* and the magnet apparatus 200*i* are such that, after the modified cochlear implants 10*h*' and 10*i* have been formed, portions of the aperture 50 volume may remain open. There may be some instances where filling the entire volume is preferred. To that end, the exemplary magnet apparatus insert 60*j* illustrated in FIGS. 77 and 78, which may include a housing portion replacement 100***j* and a magnet apparatus such as the magnet apparatus 200*h* (as shown) or the magnet apparatus 200*i*, is configured to occupy the all of (or essentially all of) the aperture 50.

Figure 79:
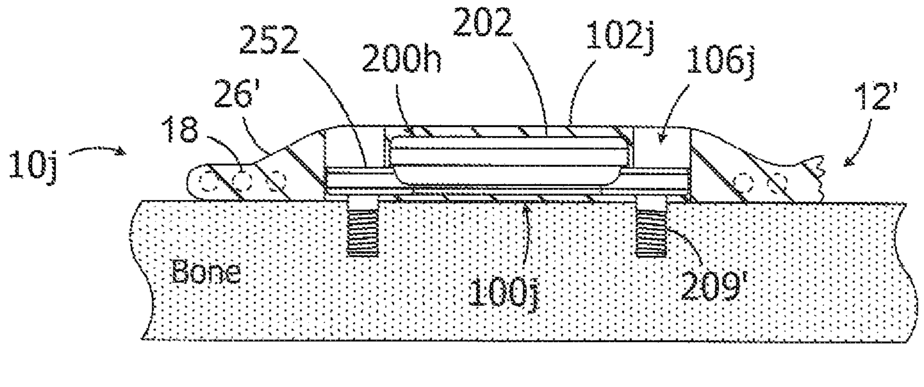
FIG. 79 is a partial section view of a modified cochlear implant in accordance with one embodiment of a present invention.

The exemplary housing portion replacement 100*j*, which may be formed from the same material as the cochlear implant housing 12 (e.g., a silicone elastomer) and overmolded onto the magnet apparatus 200*h*, includes a magnet housing 102*j* (e.g., a disk-shaped housing) with a magnet pocket 104*j* in which the magnet apparatus 200*h* is located. The housing portion replacement 100*j* also includes a pair of open regions 106*i* that are aligned with the protrusions 252. The open regions 106*i* permit passage of the bone screws 209'. The overall size and shape of housing portion replacement 100*j* (e.g., the diameter and the thickness) is the same as, or essentially the same as, that of the aperture 50. Accordingly, the magnet apparatus insert 60*j* fills the aperture 50 and allows the magnet apparatus 200*h* to be anchored to bone as shown in FIG. 79.

In some implementations, the housing portion replacement 100*j* (as well as the other housing portion replacements disclosed herein) may be formed from a drug eluting silicone or foamed silicone that is mixed with an antibacterial drug such as dexamethasone. The antibacterial drug eluting housing portion replacements will reduce the likelihood of infection, by resisting the growth of bacterial and biofilm, following a surgical procedure to replace a conventional magnet with a MRI-compatible magnet apparatus. In some instances, the drug elution may last 6 months or more.

Other methods of anchoring a magnet apparatus to bone involve the use of stiff straps that are secured to the top of the magnet apparatus and extend over the exterior of the cochlear implant housing antenna portion and down to the bone. One or more bone screws, or other anchors, may be used to secure the stiff straps and, therefore, the magnet apparatus and cochlear implant antenna portion to the bone.

Figure 80:
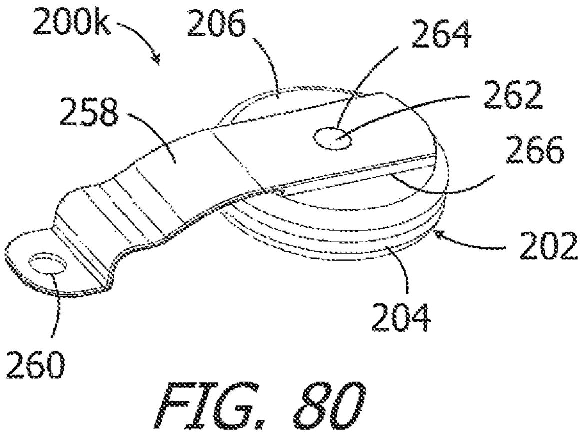
FIG. 80 is a perspective view of a magnet apparatus in accordance with one embodiment of a present invention.
Figure 81:
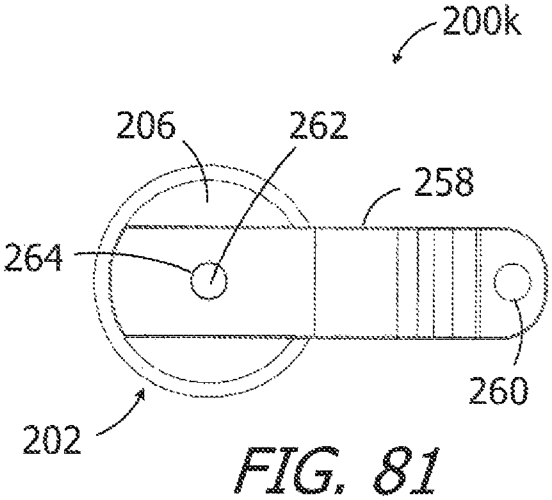
FIG. 81 is a top view of the magnet apparatus illustrated in FIG. 80.
Figure 82:
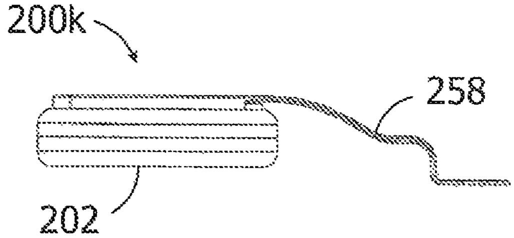
FIG. 82 is a side view of the magnet apparatus illustrated in FIG. 80.

One example of such a magnet apparatus is generally represented by reference numeral 200*k* in FIGS. 80-82. The exemplary magnet apparatus 200*k* is similar to magnet apparatus 200*i* and similar elements are represented by similar reference numerals. For example, the exemplary magnet apparatus 200*k* includes a case 202, with a base 204 and a cover 206, as well as the rotatable frame 208 (not shown) and rotatable magnets 210 (not shown) described above. The case 202, rotatable frame 208 and magnets 210 may be formed from the materials described above. Here, however, the magnet apparatus 200*k* includes a stiff strap 258. One end of the stiff strap 258 is secured to the case cover 206 and the other end includes an aperture 260 for a bone screw 209' or other bone anchor. The shape of the stiff strap 258 corresponds to that of the top surface of the housing antenna portion 26'. The stiffness of the strap 258 may be sufficient to prevent movement of the magnet case 202. Suitable strap materials and manufacturing methods include, but are not limited to, titanium (pressing or metal injection molding) and stiff biocompatible polymers such as PEEK (molding).

The stiff strap 258 may be secured to the case 202 in any suitable fashion. In the illustrated implementation, where the strap is formed from titanium, the case 202 may be provided with a central boss 262 and the stiff strap 258 may include a boss aperture 264 that extends through the thickened portion 266 of the strap. The stiff strap 258 may be welded (e.g., laser welded) to the central boss 262. In those instances where the stiff strap is formed from a polymer, the strap may include a structure (not shown) that can be press-fit over case to hold the strap in place.

Figure 83:
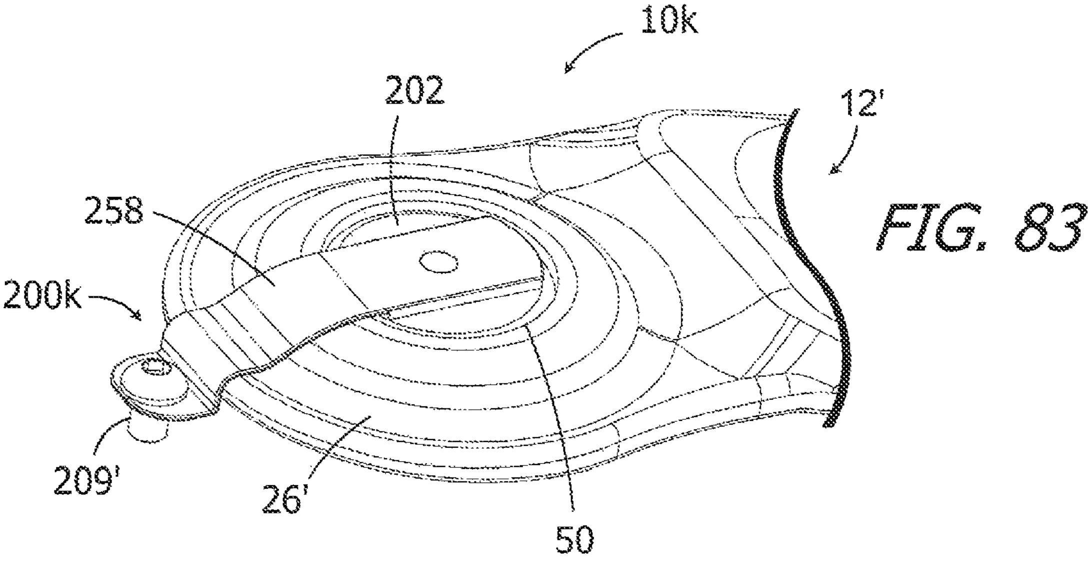
FIG. 83 is a perspective view of a modified cochlear implant in accordance with one embodiment of a present invention.

Turning to FIG. 83, the case 202 of the exemplary magnet apparatus 200*k* may be inserted into the aperture 50 to form the modified cochlear implant 10*k*. The stiff strap 258 will then extend over the top surface the housing antenna portion 26' in the illustrated location, or in other locations based on the angular/rotational orientation of the case 202 relative to the aperture 50. The bone screw 209' or other bone anchor may then be inserted through the aperture 260 and driven into bone to secure the stiff strap 258 to the bone and, therefore, to secure the magnet apparatus 200*k*, the cochlear implant antenna portion 26', and the modified cochlear implant 10*k* to the bone.

Figure 84:
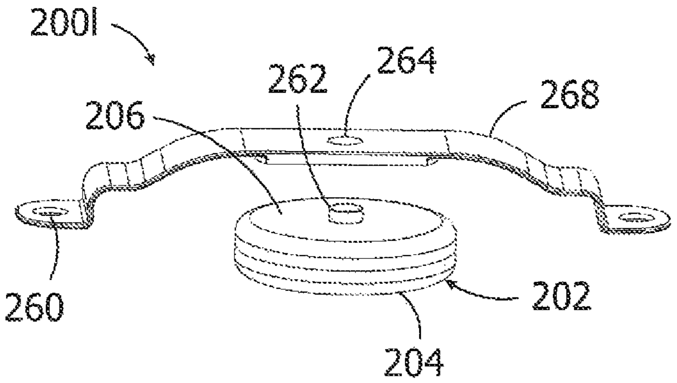
FIG. 84 is an exploded perspective view of a magnet apparatus in accordance with one embodiment of a present invention.
Figure 85:
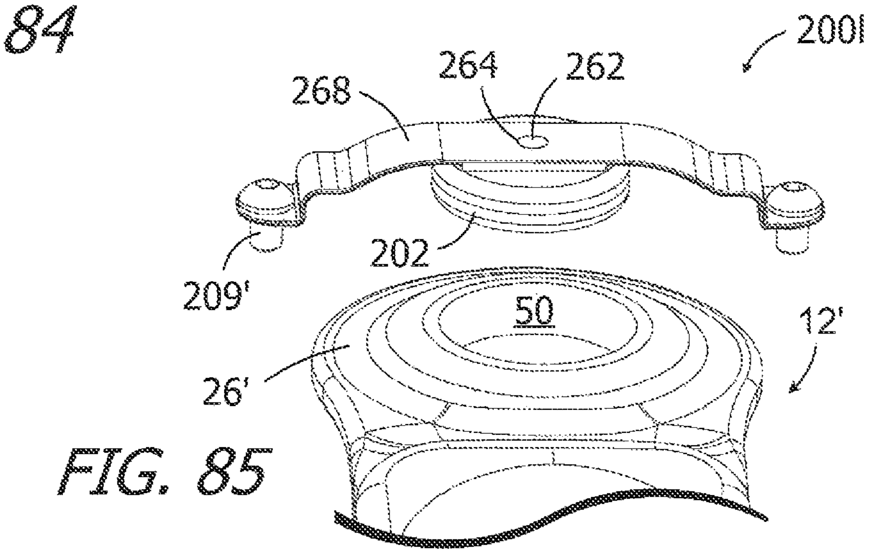
FIG. 85 is an exploded partial section view of an aspect of a cochlear implant modification process in accordance with one embodiment of a present invention.

Another exemplary magnet apparatus is generally represented by reference numeral 200*l* in FIGS. 84 and 85. The magnet apparatus 200*l* is substantially similar to magnet apparatus 200*k* and similar elements are represented by similar reference numerals. For example, the magnet apparatus 200*l* includes a case 202, with a base 204 and a cover 206, as well as the rotatable frame 208 (not shown) and rotatable magnets 210 (not shown) described above. The magnet apparatus 200*l* also includes a stiff strap 268 that may be anchored to bone and may be formed from the materials and methods described above in the context of stiff strap 258. To that end, the exemplary case 202 includes a central boss 262 and the stiff strap includes a boss aperture 264.

Figure 86:
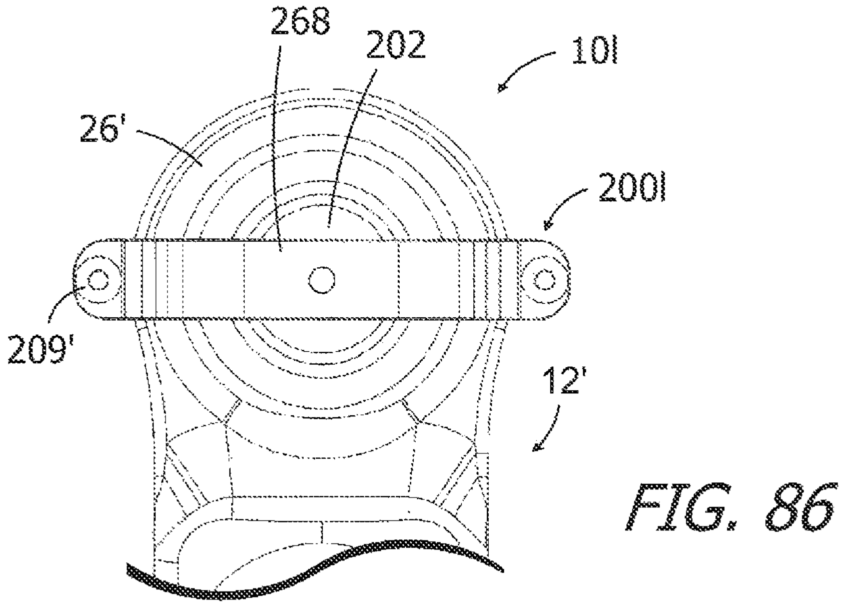
FIG. 86 is a top view of a modified cochlear implant in accordance with one embodiment of a present invention.

Here, however, the stiff strap 268 extends in two directions from the case 202 and includes an anchor aperture 260 at each end. As a result, the stiff strap 268 extends over two portions of the top surface the housing antenna portion 26' when the case 202 is inserted into the aperture 50 in the manner illustrated in FIG. 86. Bone screws 209' or other bone anchors may then be inserted through the apertures 260 and driven into bone at two points to secure the stiff strap 268 to the bone and, therefore, to secure the magnet apparatus 200*l*, the cochlear implant antenna portion 26', and the modified cochlear implant 10*l* to the bone.

It should also be noted that although the stiff strap 268 is linear and anchored to the bone at locations that are offset from one another by 180 degrees about the above-described axis defined by the case 202, other configurations may be employed such as, for example, V-shapes, L-shapes and X-shapes.

Turning to FIGS. 87 and 88, the exemplary magnet apparatus 200*m* illustrated therein is substantially similar to magnet apparatus 200*k* and similar elements are represented by similar reference numerals. For example, the magnet apparatus 200*m* includes a case 202, with a base 204 and a cover 206, as well as the rotatable frame 208 (not shown) and rotatable magnets 210 (not shown) described above. The magnet apparatus 200*m* also includes a stiff strap 270, with an aperture 260, that may be anchored to bone and may be formed from the materials described above in the context of stiff strap 258.

Here, however, the magnet apparatus 200*m* is configured in such a manner that the stiff strap 270 will extend under the bottom surface the housing antenna portion 26'. To that end, the stiff strap 270 extends radially or otherwise outwardly from the bottom end of the case base 204. The case base 204 and stiff strap 270 may be machined from a common blank or metal injection molded in a common mold, or may be separate elements that are welded (e.g., laser welded) or otherwise secured to one another.

Turning to FIGS. 89-91, the case 202 of the exemplary magnet apparatus 200*m* may be inserted into the bottom end of the aperture 50 of a modified antenna portion 12' by, for example, bending the antenna portion 26' upwardly. When the case 202 is fully inserted, the stiff strap 270 will rest against the bottom wall 48, thereby completing the modified cochlear implant 10*m*. A bone screw 209' or other bone anchor may then be inserted through the aperture 260 and driven into bone to secure the stiff strap 270 and, therefore, the magnet apparatus 200*m*, to the bone.

Figure 92:
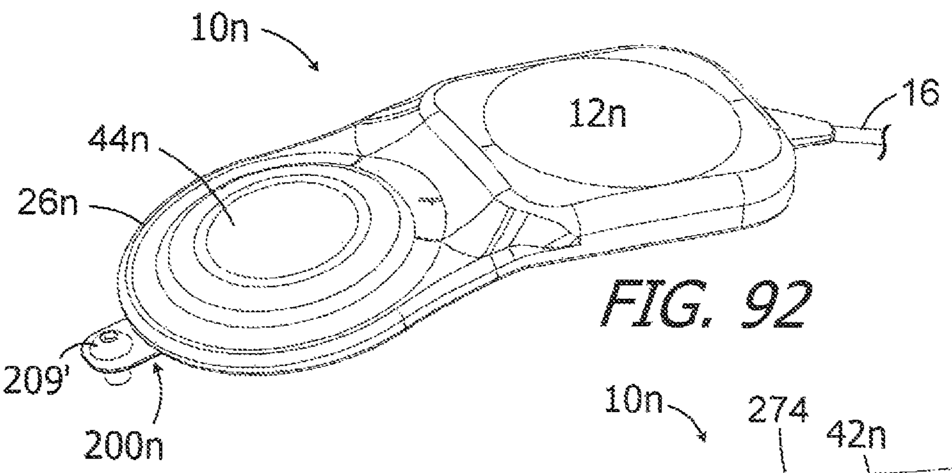
FIG. 92 is a perspective view of a cochlear implant in accordance with one embodiment of a present invention.
Figure 93:
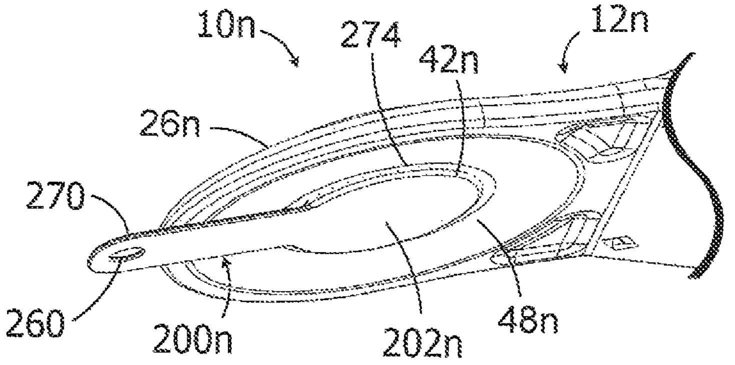
FIG. 93 is a perspective view of the cochlear implant illustrated in FIG. 92.
Figure 94:
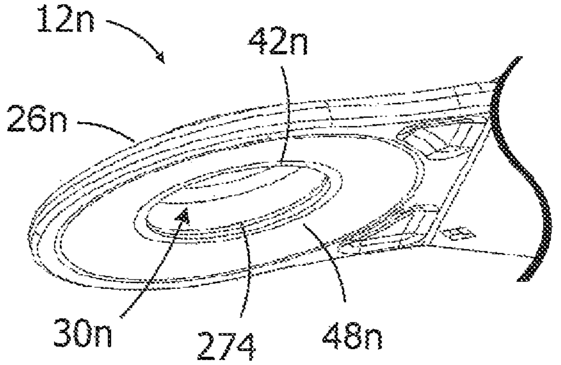
FIG. 94 is a perspective view of a portion of the cochlear implant illustrated in FIG. 92.
Figure 95:
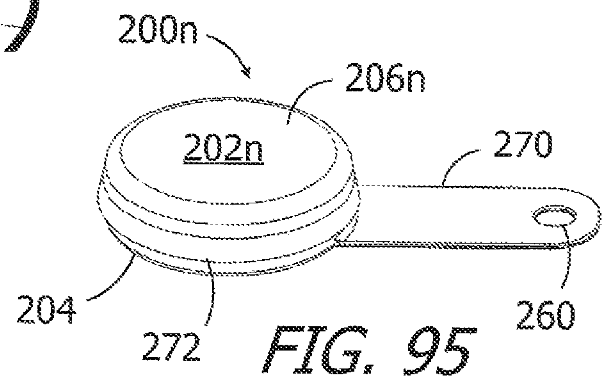
FIG. 95 is a perspective view of a magnet apparatus in accordance with one embodiment of a present invention.
Figure 97:
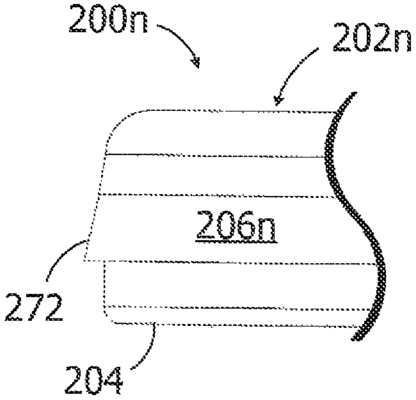
FIG. 97 is a side view of a portion of the magnet apparatus illustrated in FIG. 95.
Figure 96:
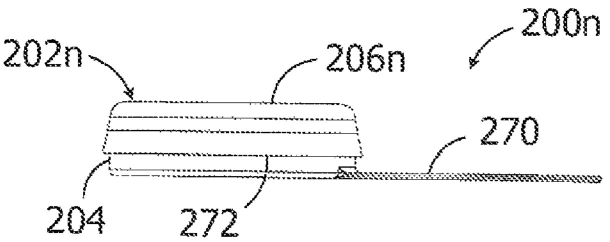
FIG. 96 is a side view of the magnet apparatus illustrated in FIG. 95.

Other cochlear implants may be pre-configured to include a magnet apparatus similar to that illustrated in FIGS. 87 and 88. For example, the exemplary cochlear implant 10*n* illustrated in FIGS. 92 and 93 is substantially similar to cochlear implant 10 and similar elements are represented by similar reference numerals. Here, however, the housing 12*n* includes a housing pocket 30*n* that is accessible by way of a magnet aperture 42*n* that extends through the housing bottom wall 48*n* (FIG. 94). The top wall 44*n* does not include an aperture. The magnet apparatus 200*n* is substantially similar to the magnet apparatus 200*m* in that it includes a case 202*n*, with a base 204 and a cover 206*n*, as well as the rotatable frame 208 (not shown) and rotatable magnets 210 (not shown) described above. The magnet apparatus 200*n* also includes a stiff strap 270, with an aperture 260, that may be anchored to bone. The case 202*n* and strap 270 may be formed using the materials and methods described above.

In other embodiments, the number of stiff straps 270 and/or anchor points may be increased beyond the illustrated single strap. For example, an elongate strap that extends outwardly beyond the case 202*n* in two areas that are offset from one another by 180 degrees about the above-described axis defined by the case may be employed. Other configurations where the straps define, for example, V-shapes, L-shapes and X-shapes, may also be employed.

The housing 12*n* and magnet apparatus 200*n* may also be configured in such a manner that they mechanically interconnect with one another when the case 202*n* is inserted through the aperture 42*n* and into the housing pocket 30*n*.

Referring to FIGS. 94-97, the case cover 206*n* in the illustrated implementation includes a relatively sharp projection 272 and the housing 12*n* includes a lip (or "under-cut') 274. The projection 272 snaps over the lip 274 as the case 202*n* is inserted into the housing pocket 30*n*, thereby securing the magnet apparatus 200*n* to the housing 12*n* and forming the cochlear implant 10*n*. In other implementations, the case base 204 may include the projection, or the case may include a recess and the housing pocket may include a corresponding projection. Regardless of the configuration of the mechanical interconnect, the case 202*n* can be pulled out of the housing 12*n* if desired because the housing material is relatively soft.

Figure 98:
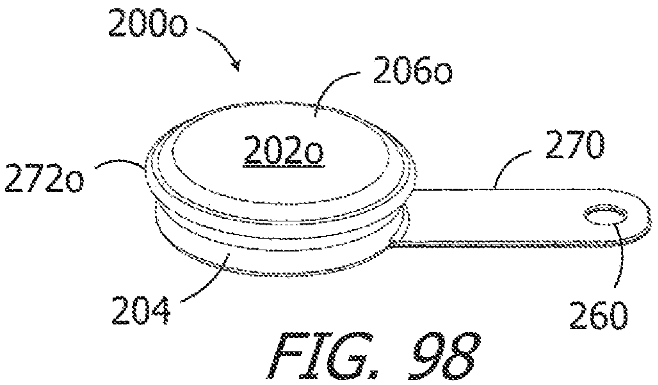
FIG. 98 is a perspective view of a magnet apparatus in accordance with one embodiment of a present invention.
Figure 99:
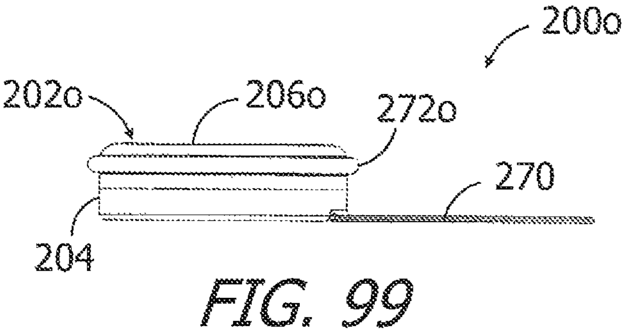
FIG. 99 is a side view of the magnet apparatus illustrated in FIG. 98.
Figure 100:
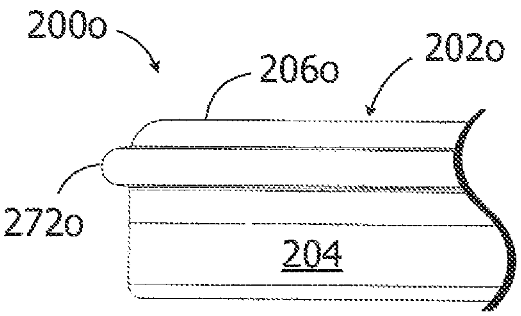
FIG. 100 is a side view of a portion of the magnet apparatus illustrated in FIG. 98.

Turning to FIGS. 98-100, the exemplary magnet apparatus 200*o* illustrated therein is substantially similar to magnet apparatus 200*n* and similar elements are represented by similar reference numerals. The magnet apparatus 200*o* includes a case 202*o*, with a base 204 and a cover 206*o*, as well as the rotatable frame 208 (not shown) and rotatable magnets 210 (not shown) described above. The magnet apparatus 200*o* also includes one or more stiff straps 270, each with an aperture 260, that may be anchored to bone. The case 202*o* and strap 270 may be formed using the materials and methods described above. Here, however, the projection 272*o* is not sharp and has a semi-circular shape. The magnet apparatus 200*o* may be used with a cochlear implant housing with or without a corresponding semi-circular indentation in the housing pocket.

Figure 101:
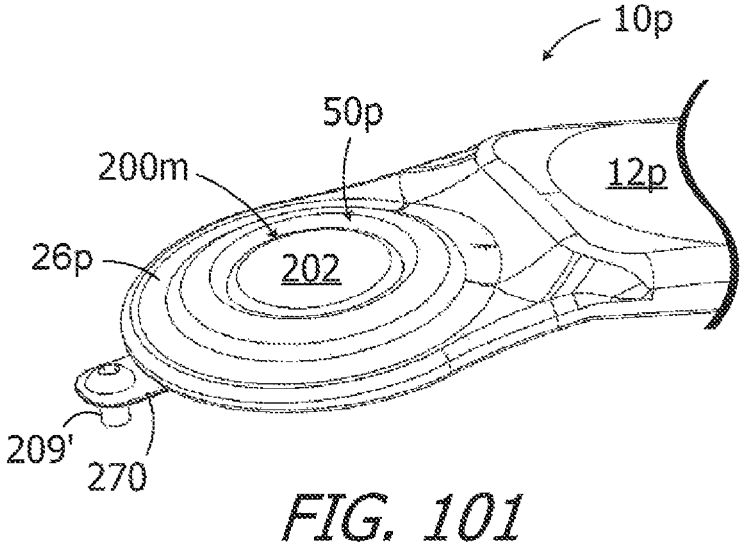
FIG. 101 is a perspective view of a cochlear implant in accordance with one embodiment of a present invention.
Figure 102:
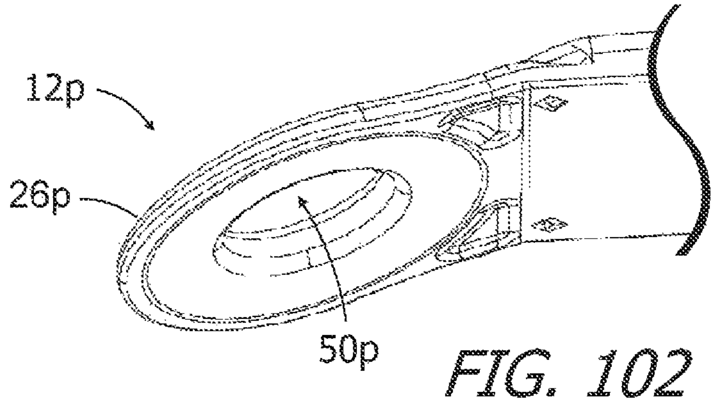
FIG. 102 is a perspective view of a portion of the cochlear implant illustrated in FIG. 101.
Figure 103:
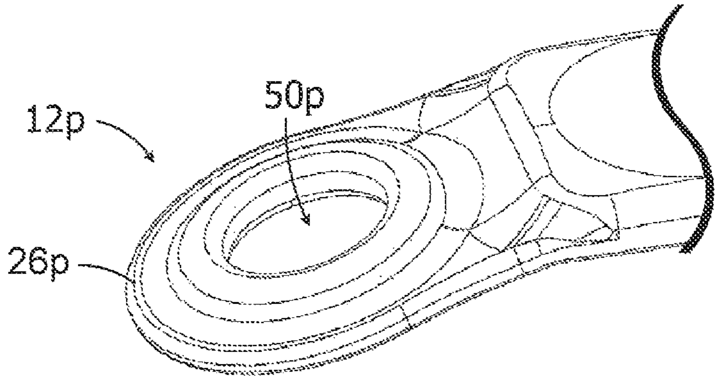
FIG. 103 is a perspective view of a portion of the cochlear implant illustrated in FIG. 101.
Figure 109:
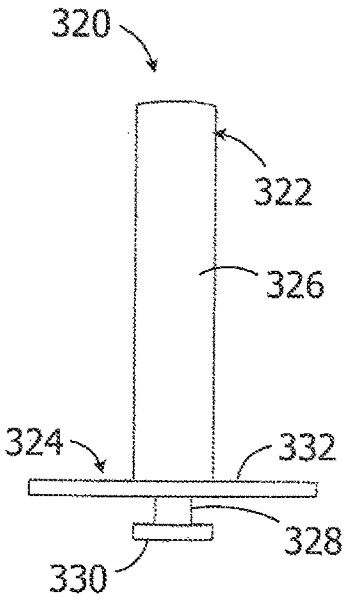
FIG. 109 is a side view of a cutting tool positioner in accordance with one embodiment of a present invention.
Figure 110:
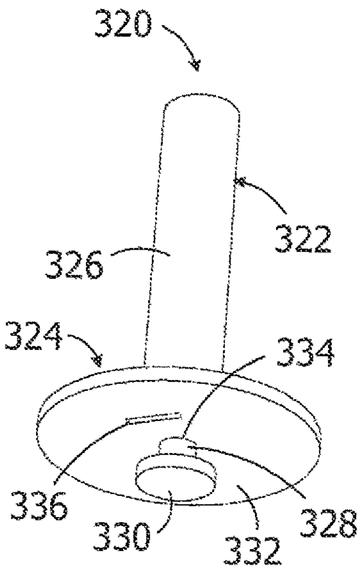
FIG. 110 is a perspective view of a cutting tool positioner illustrated in FIG. 109.
Figure 111:
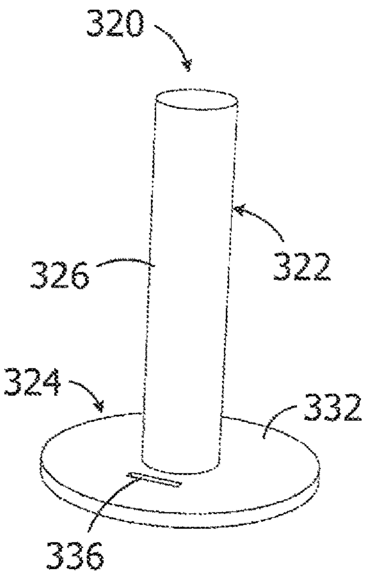
FIG. 111 is a perspective view of a cutting tool positioner illustrated in FIG. 109.
Figure 112:
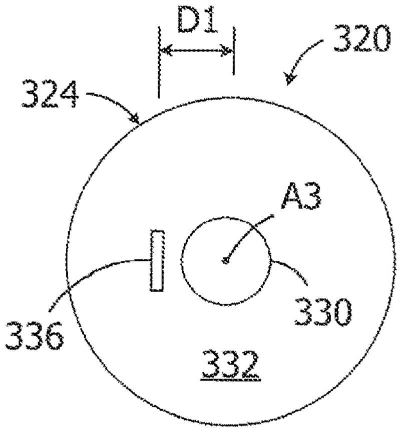
FIG. 112 is a bottom view of a cutting tool positioner illustrated in FIG. 109.

One example of a cochlear implant that is pre-configured to include the magnet apparatus 200*m* (FIGS. 87 and 88) is generally represented by reference numeral 10*p* in FIG. 101. The cochlear implant 10*p* includes, among other things, the above-described magnet apparatus 200*m* and a housing 12*p*. The housing 12*p* (FIGS. 102 and 103) is similar to housing 12*n* (FIGS. 92-94), but lacks the lip 274 and has a magnet aperture 50*p* that extends completely through the antenna portion 26*p*. This arrangement allows the housing 12*p* to be thinner than, for example, the housing 12 because there is no need for material above or below the magnet case 202.

It should be noted here that the present magnet apparatus inserts are not limited to the MRI-compatible magnet apparatus described above or any other particular type of magnet apparatus. The magnet apparatus illustrated in U.S. Pat. No. 8,634,909, which has been proposed for use in an MRI magnetic field, is another example of a magnet apparatus that may be incorporated into the present magnet apparatus inserts.

As alluded to above, a wide variety of tools may be used to remove material in situ from an implanted cochlear implant in the manner described above with reference to, for example, FIGS. 4-13. Examples of such tools are described below in FIGS. 104-152. Such tools may be employed in methods that involve removing the housing material (and magnet) by forming incisions into the cochlear implant housing that originate at the top surface (or "skin side") of the implant as opposed to the bottom surface (or "bone side"). Access to the cochlear implant may be obtained by way of an incision that is made directly over the antenna portion (including directly over the magnet) or by way of an incision that is in front of the antenna portion (i.e., to the left of the antenna portion in FIG. 2) and offset up to +/−30 degrees from directly in front (i.e., from about reference numeral 42 to reference numeral 46 in FIG. 1).

Referring first to FIGS. 104 and 105, the exemplary stencil 300 includes a main body 302 with an antenna portion 304 and a finger rest 306. The antenna portion includes a cutout 308 with first and second semi-circular portions 310 that are separated by gaps 312. The cutout 308 is sized and shaped to guide a scalpel blade 72 (FIG. 107) along a circular cutting path that is located radially inward of the antenna 18 and radially outward of the magnet pocket 30. Suitable materials for the stencil include, but are not limited to, metals such as stainless steel.

Turning to FIGS. 106 and 107, the magnet 28 may remain within the pocket 30 during a procedure involving the stencil 300 to create the modified antenna portion 26' with the aperture 50 (FIGS. 5 and 6). Access to the cochlear implant may, in at least some instances, be provided by an incision that is directly over the antenna portion (including directly over the magnet). The stencil 300 may be positioned over the cochlear implant 10 (or other cochlear implant) in such a manner that the antenna portion 304 is located over the implant housing antenna portion 26 and is centered relative to the magnet 28 and magnet pocket 30. The position of the stencil 300 relative to the cochlear implant 10 may be maintained by applying downward pressure to the finger rest 306. The scalpel blade 72 may then be inserted into one of the semi-circular cutout portions 310, pressed completely or partially through the housing antenna portion 26, and advanced from one end to the other. In those instances where the blade 72 is only pushed partially through the housing antenna portion 26, the process will be repeated until a semi-circular cut is formed from top to bottom. Another semi-circular cut may also be formed with the other cutout portion 310. With respect to the uncut regions under the gaps 312, the stencil 300 may either be rotated slightly so that the cutout portions 310 will be aligned with the uncut regions or the stencil may be removed to expose the uncut portions. In either case, the scalpel blade 72 may then be pushed through the uncut regions to form the severed portion 29 illustrated in FIG. 108. The stencil 300 may also be used to remove the severed portion 29 of the cochlear implant 10 because the magnet 28, which remains in the pocket 30, will be attracted to the metal stencil.

The exemplary cutting tool positioner 320 illustrated in FIGS. 109-113 may be used in conjunction with a sharp tool, such as a scalpel, to form an aperture 50 (FIGS. 5 and 6). The exemplary cutting tool positioner 320 includes a centering post 322 and a rotatable tool guide 324 that is mounted on, and is rotatable to, the centering post. The exemplary centering post 322 includes a handle 326, an axle 328 for the rotatable tool guide 324, and an anchor 330 that is configured to fit into the magnet pocket of the associated cochlear implant (e.g., the magnet pocket 30 of cochlear implant 10). The exemplary rotatable tool guide 324, which rotates around the axis A3 defined by the centering post 322, is in the form of a disk 332 with a central aperture 334 for the axle 328 and a slot 336 for the cutting tool blade. The distance D1 (FIG. 112) from the slot 336 to the axis A results in the cutting tool blade being located radially inward of the antenna 18 and radially outward of the magnet pocket 30.

Figure 113:
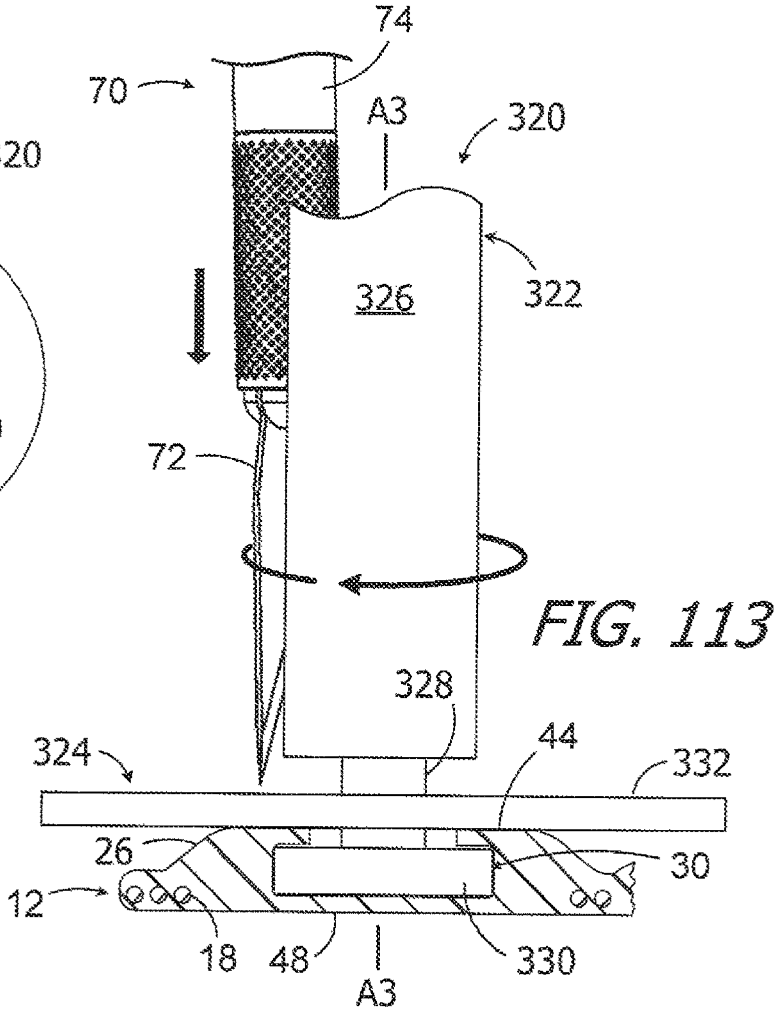
FIG. 113 is a side, partial section view of an aspect of a cochlear implant modification process in accordance with one embodiment of a present invention.

Referring more specifically to FIG. 113, the exemplary cutting tool positioner 320 may be used in conjunction with a scalpel 70 that includes a blade 72 and a handle 74 to, for example, create the partial housing 12' (FIGS. 5 and 6) that includes the modified antenna portion 26' with the aperture 50. Access to the cochlear implant may, in at least some instances, be provided by an incision that is directly over the antenna portion 26 (and magnet 28). After the magnet 28 has been removed, the anchor 330 of the centering post 322 may be inserted into the magnet pocket 30, thereby performing the function of centering the cutting tool positioner 320 relative to the antenna 18 and magnet pocket 30. The rotatable tool guide 324 will rest on the top wall 44 if the cochlear implant housing 12. The scalpel blade 72 may then be inserted through the slot 336 and pressed completely or partially through the housing antenna portion 26. The rotatable tool guide 324 will keep the scalpel blade 72 on a circular path as the blade is moved around the centering post 322 by the surgeon. In those instances where the blade 72 is only pushed partially through the housing antenna portion 26, more than one revolution will be required for the cut to be formed from top to bottom. The centering post 322, which is attached to the severed portion of the housing by way of the anchor 330, may be used to pull the severed portion out of the housing to complete the above-described partial housing 12' with the modified antenna portion 26' (FIGS. 5 and 6).

Figure 114:
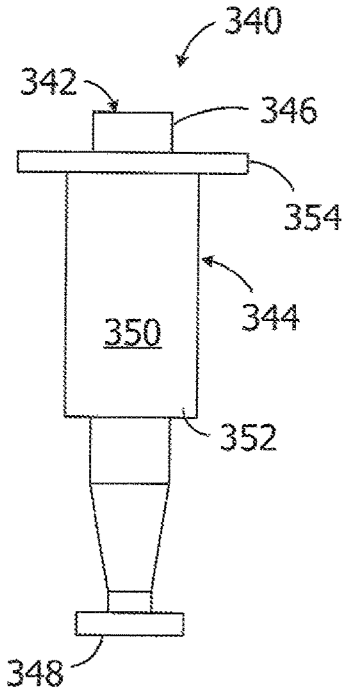
FIG. 114 is a side view of a center punch in accordance with one embodiment of a present invention.
Figure 115:
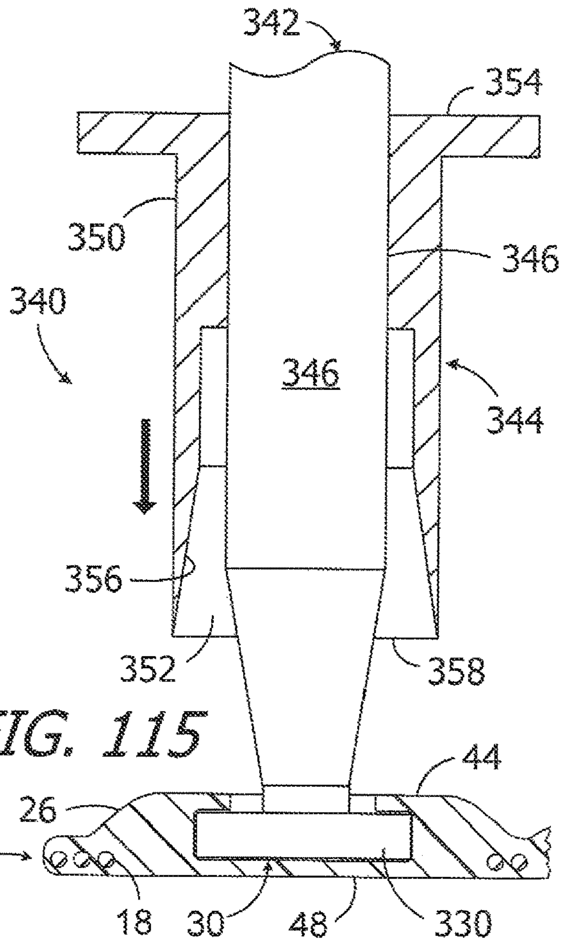
FIG. 115 is a bottom view of the center punch illustrated in FIG. 114.
Figure 116:
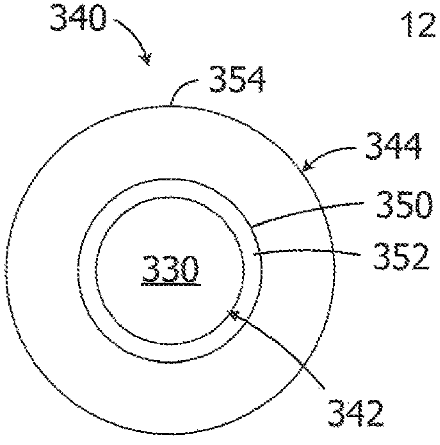
FIG. 116 is a side, partial section view of an aspect of a cochlear implant modification process in accordance with one embodiment of a present invention.
Figure 117:
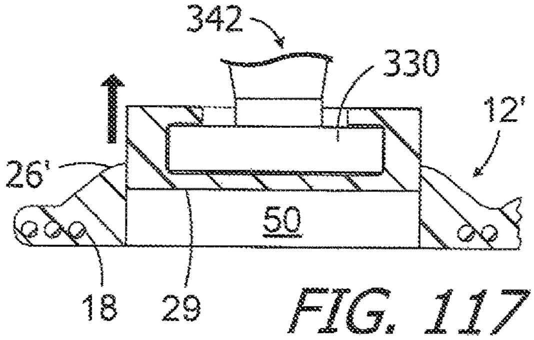
Figure 118:
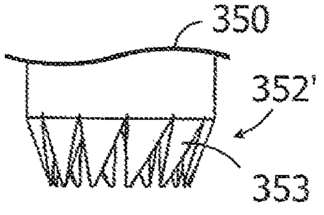
Figure 119:
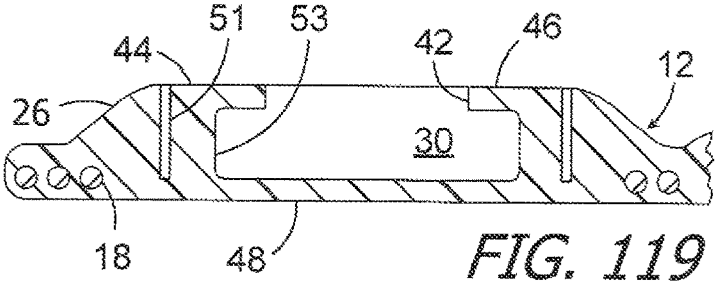

Another tool that may be used to remove a portion of a cochlear implant housing is the center punch 340 illustrated in FIGS. 114-116. The exemplary center punch 340 includes a centering post 342 and a cutter 344 that is mounted on the centering post in such a manner that the cutter may be moved longitudinally and rotationally. The exemplary centering post 342 includes a handle 346 and an anchor 348 that is configured to fit into the magnet pocket of the associated cochlear implant (e.g., the magnet pocket 30 of cochlear implant 10). The exemplary cutter 344 includes a tubular member 350 with a blade 352 on one end and an annular flange 354 at the other end. The inner diameter of the blade 352 is greater than the diameter of the magnet pocket 30 and is less than the diameter of the antenna 18 and, in the illustrated implementation, is the same as the diameter of the aperture 50 (FIG. 5).

A variety of blades with ends having an overall circular shape may be employed. The exemplary blade 352 illustrated in FIGS. 114-116 includes a tapered portion 356 and a continuous sharp circular edge 358. In other implementations of the tool, such as that illustrated in FIG. 118, the blade 352' may include a plurality of spaced teeth 353.

Referring more specifically to FIG. 114, the exemplary center punch 340 may be used to, for example, create the partial housing 12' (FIGS. 5 and 6) that includes the modified antenna portion 26' with the aperture 50. Access to the cochlear implant may, in at least some instances, be provided by an incision that is directly over the antenna portion 26 (including directly over the magnet). After the magnet 28 has been removed, the anchor 348 of the centering post 342 may be inserted into the magnet pocket 30, thereby performing the function of centering the cutter 344 (and cutter blade 352) relative to the antenna 18 and magnet pocket 30. The blade 352 may then be driven completely through the housing antenna portion 26 by pressing on the flange 354 and driving the cutter 344 (and cutter blade 352) longitudinally along the centering post 342. The cutter 344 may also be rotated if necessary or desired. The centering post 342, which is attached to the severed portion of the housing by way of the anchor 348, may be used to pull the severed portion 29 out of the housing (FIG. 117) to complete the above-described partial housing 12' with a modified antenna portion 26' (FIGS. 5 and 6).

Figure 9:
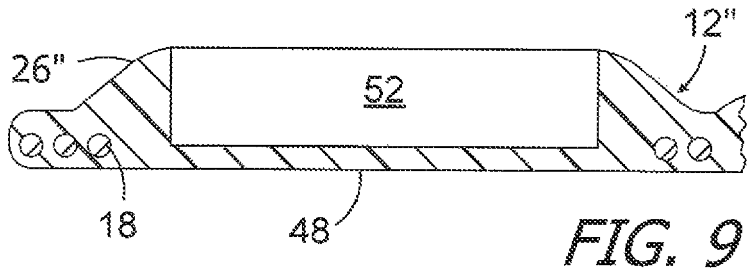
FIG. 9 is a section view of an aspect of a cochlear implant modification process in accordance with one embodiment of a present invention.

The exemplary stencil 300, cutting tool positioner 320, and center punch 340 may also be used in those instances where the surgeon intends to form an aperture that extends partially through the housing, such as the cylindrical aperture 52 illustrated in FIGS. 9 and 10. As illustrated for example in FIG. 119, the cutting implement, e.g., the scalpel blade 72 or cutter blade 352, will be pressed below the top wall 44 of the cochlear implant housing 12 to a depth equal to that of the magnet pocket 30. The circular cut 51 produced by the scalpel blade 72 or cutter blade 352 creates a substantially annular piece of housing material 53 that surrounds the magnet pocket 30 and is connected to the remainder of the housing 12 at the bottom wall 48. The substantially annular piece of housing material 53 may then be cut, torn or otherwise removed from the housing 12 to form the aperture 52 illustrated in FIGS. 9 and 10.

One example of a tool that may be used to enlarge a magnet pocket, e.g., enlarge the magnet pocket 30 into the magnet pocket **30*a* (FIG. 12), is the coring tool 360 illustrated in FIGS. 120-122. Access to the cochlear implant may, in at least some instances, be provided by an incision that is directly over the antenna portion (including directly over the magnet). The coring tool 360 includes a handle 362 and a blade assembly 364, with first and second blades 366 and 368 on a frame 370, which is connected to the handle and performs the function of enlarging the magnet pocket by shaving shave material off of the housing 12 from within the magnet pocket. The distance D2 between the free ends of the blades 366 and 368 is equal to the diameter of the enlarged magnet pocket. The frame 370 has an overall parallelepiped shape, with the blades 366 and 368 located at the acute angles, and includes a top wall 372, a bottom wall 374 and side walls 376 and 378. The walls 372-378 define openings 380 and 382 as well as an internal volume 384**.

The exemplary tool 360 may be used to enlarge a magnet pocket in, for example, the cochlear implant 10 in the manner illustrated in FIG. 123. After the magnet 28 has been removed (FIG. 4), the blade assembly 364 may be inserted into the magnet pocket 30 by way of the magnet aperture 42. The magnet pocket 30 will be stretched out if its circular shape because the distance D2 between the free ends of the blades 366 and 368 is greater than the diameter of the magnet pocket 30. The handle 362 may then be used to rotate the blade assembly 364 within the pocket 30. Such rotation will cause the blades 366 and 368 to shave material off of the housing 12 to create the modified housing 12*c*, which includes a magnet pocket 30*c* (FIG. 12) that is larger in diameter than the pre-modification magnet pocket 30. The shavings are free to enter or exit the volume 384 during rotation of the blade assembly 364 by way of the openings 380 and 382. The blade assembly 364 may then be removed from the pocket 30*c*, and any shavings that remain may be removed by suction.

Figure 124:
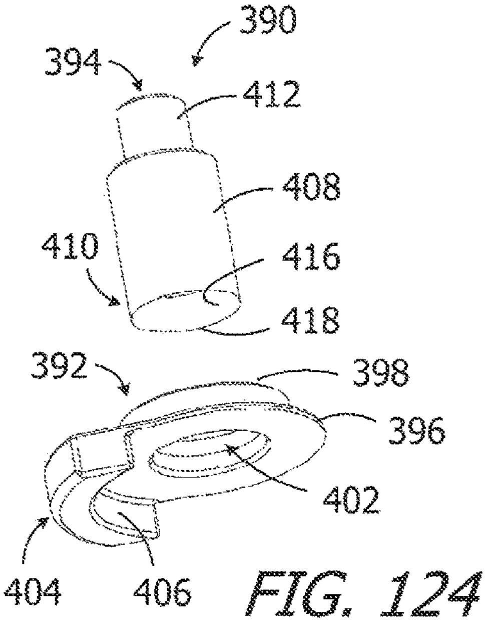
Figure 125:
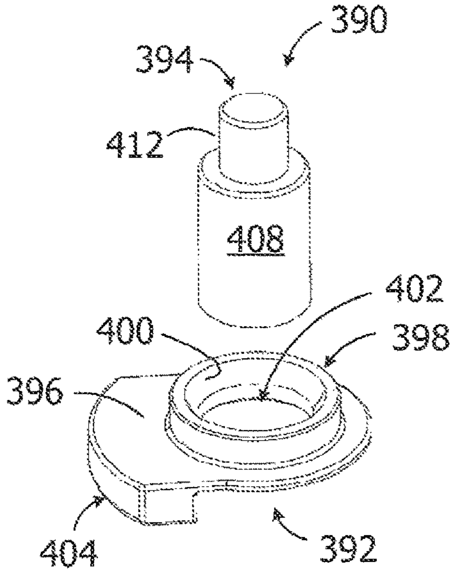
Figure 126:
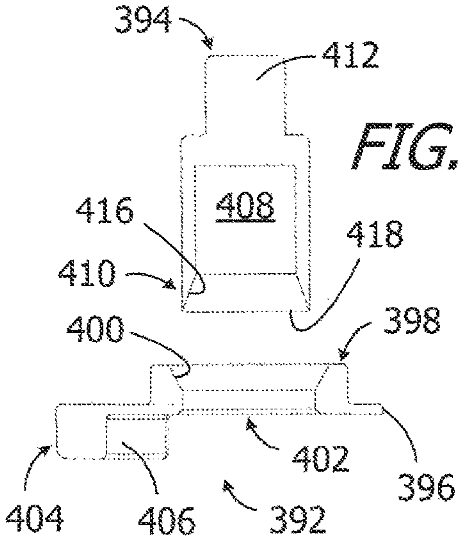

One example of a tool that may be used to remove the magnet and a portion of a cochlear implant housing is the coring and removal tool 390 illustrated in FIGS. 124-126. The exemplary coring and removal tool 390 includes a centering template 392 and a cutter 394 that is movable through the centering template. Access to the cochlear implant may, in at least some instances, be provided by an incision that is directly over the antenna portion (including directly over the magnet). The exemplary centering template 392 includes a base 396, a guide 398 with a tapered inlet surface 400 and an aperture 402 that extends through the base for the cutter 394, and an abutment 404 with a curved surface 406 with a shape that corresponds to the outer edge of the associated housing antenna portion. The exemplary cutter 394 includes a tubular member 408 with a blade 410 on one end and a connector 412 for a handle 414 (FIG. 130) at the other end. Although a variety of blades with ends having an overall circular shape may be employed, the exemplary blade 410 includes a tapered portion 416 and a continuous sharp circular edge 418. The cutter 394 may also be mounted on a screw punch, which will rotate the cutter, as is discussed below with reference to FIGS. 149-153.

Figure 127:
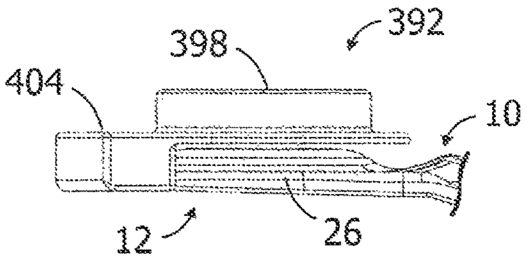
Figure 128:
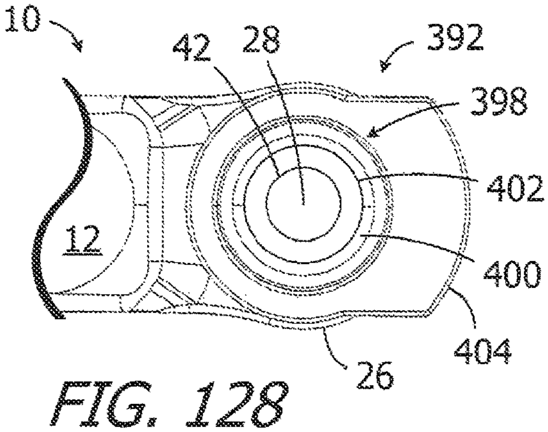

The respective positions of the aperture 402 and curved surface 406 of the exemplary centering template 392 are such that the aperture will be centered relative to the magnet 28 and magnet pocket 30 of the associated cochlear implant 10 when the antenna portion 26 contacts the curved abutment surface 406, as shown in FIGS. 127-129. The inner diameter of the blade 410 is greater than the diameter of the magnet pocket 30 and is less than the diameter of the antenna 18 and, in the illustrated implementation, is the same as the diameter of the aperture 50 (FIG. 5). Additionally, the outer diameter of the tubular member 408 slightly less than the diameter of the template aperture 402, which results the blade 410 being centered relative to the magnet 28 and magnet pocket 30.

Turning to FIGS. 130 and 130A, the exemplary coring and removal tool 390 may be used to, for example, create the partial housing 12' (FIGS. 5 and 6) that includes the modified antenna portion 26' with the aperture 50. After the centering template 392 has been positioned on top of the housing antenna portion 26 and the curved surface of the abutment 404 has been pressed against the end of the antenna portion, thereby centering the aperture 402 relative to the magnet 28, the tubular member 408 of the cutter 394 may be inserted into the template guide 398 and through the aperture 402. The blade 410, which is also centered relative to the magnet 28, may then be pushed through the antenna portion 12 (between the magnet 28 and the antenna 18) until the circular edge 418 passes through the bottom wall 48. The cutter 394 may also be rotated if necessary or desired. In addition to being severed from the remainder of the housing 12, the severed portion 29 (in which the magnet 28 is located) will be wedged into the tapered portion 416 of the blade 410. The severed portion 29 (and magnet 28) may then be removed from the partial housing 12' with the blade 410, which as a modified antenna portion 26' with the aperture 50, as can be seen in FIGS. 131 and 132.

Another tool that may be used to remove a portion of a cochlear implant housing is the coring and removal tool 420 illustrated in FIGS. 133-136. The exemplary coring and removal tool 420 includes a centering template 422, a cutter 424 that is movable relative to the centering template, and an actuator 426 that may be used to drive the cutter through a cochlear implant antenna portion that is located on the centering template. The exemplary centering template 422 includes a base 428, a ramp 430, an abutment 432 with a curved surface 434, and a relief 436 for the cutter 424. The exemplary cutter 424 includes a blade 438 that has a tapered portion 440 and a continuous sharp circular edge 442. The exemplary actuator 426 includes first and second resilient (e.g., metal) elongate members 444 and 446 with first longitudinal ends that are connected to one another at an attachment point 448. The second longitudinal ends, which are spaced apart from one another, support the centering template 422 and the cutter 424. The exemplary actuator 426 also includes a lever 450 that is connected to the first elongate member 444 by a pin 452 that extends through an opening 454 in the second elongate member 446. The lever 450 has a fulcrum 456 that is adjacent to the pin 452 and that rests on the surface of the elongate member 446.

The exemplary actuator 426 functions in a manner similar to the actuator on a finger nail clipper. Referring to FIG. 133, when the user applies downward force (in the illustrated orientation) to the lever 450, force will be applied to the second elongate member 446 by the fulcrum 456, thereby driving the cutter 424 towards the centering template 422. The resilience of the elongate member 446 will cause the elongate member 446 to return to the state illustrated in FIG. 133 when the force is removed.

The respective positions of the cutter 424 and curved surface 434 of the exemplary centering template 422 are such that the cutter blade 438 will be centered relative to the magnet 28 and magnet pocket 30 of the associated cochlear implant 10 when the antenna portion 26 is pressed against the curved surface. The inner diameter of the blade 438 is greater than the diameter of the magnet pocket 30 and is less than the diameter of the antenna 18 and, in the illustrated implementation, is the same as the diameter of the aperture 50 (FIG. 5). Additionally, the outer diameter of the blade 438 is slightly less than the diameter of the template relief 436.

The exemplary coring and removal tool 420 illustrated in FIGS. 133-136 may be used to, for example, create the partial housing 12' (FIGS. 5 and 6) that includes the modified antenna portion 26' with the aperture 50. Access to the cochlear implant may, in at least some instances, be obtained by way of an incision that is in front of the antenna portion and offset up to +/−30 degrees from directly in front of the antenna portion. The low profile of the distal portion of the tool, i.e., the portion with the centering template 422 and the cutter 424, allows the distal portion to be inserted under the skin by way of a relatively small incision. The ramp 430 facilitates sliding of the centering template 422 under the antenna portion of the in situ cochlear implant. The tool 420 can be moved toward the cochlear implant until the antenna portion is in contact with the curved surface 434, thereby centering the blade 438 relative to the magnet. The lever 450 may then be used to drive the cutter 424 downwardly until the circular edge 442 passes completely through the antenna portion (between the magnet and the antenna) and the circular edge engages the surface of the relief 436. In some instances, this will be about 6 mm of travel. The mechanical advantage associated with the fulcrum-based actuator 426 allows the user to drive the blade 438 through the housing with less than the 20-30 lbs. that would otherwise be required. The severed portion of the housing (in which the magnet is located) will be wedged into the tapered portion 440 in the manner described above with reference to FIG. 130A. Releasing the lever 450 will allow the cutter to be returned to its rest position (FIG. 133), thereby pulling the severed portion (and magnet) out of the partial housing.

The exemplary coring and removal tool 460 illustrated in FIGS. 137-141 is similar to tool 420 (FIGS. 133-136) in that tool 460 includes a centering template 422, a cutter 424 that is movable relative to the centering template, and an actuator 462 that may be used to drive the cutter through a cochlear implant antenna portion that is located on the centering template. The centering template 422, which functions in the manner described above, includes a base 428, a ramp 430, a pair of abutments 432' with respective curved surfaces 434', and a relief 436 for the cutter 424. The exemplary cutter 424 includes a blade 438 with a tapered portion 440 and a continuous sharp circular edge 442.

The exemplary actuator 462 includes a cutter carrier 464 that moves along pins 466, an elongate member 468, a lever 470 and a gear assembly 472 that converts motion of the lever into motion of the cutter carrier. The gear assembly 472 in the illustrated implementation includes a gear 474 that is fixedly secured to the lever 470 and that rotates with the lever about a shaft 476, a rack gear 478 that is fixedly secured to the cutter carrier 464, and a pinion gear 480 that engages gears 474 and 478 and that rotates about a shaft 482. The shafts 476 and 482 are mounted on shaft supports 484. Referring to FIGS. 137 and 139, when the user moves the lever 470 downwardly (in the illustrated orientation), the gear assembly 472 will drive the cutter carrier 464 (and cutter 424) towards the centering template 422. Movement of the lever 470 in the opposite direction will drive the cutter carrier 464 (and cutter 424) away from the centering template 422.

The exemplary coring and removal tool 460 illustrated in FIGS. 137-141 may be used to, for example, create the partial housing 12' (FIGS. 5 and 6) that includes the modified antenna portion 26' with the aperture 50. Access to the cochlear implant may, in at least some instances, be obtained by way of an incision that is in front of the antenna portion and offset up to +/−30 degrees from directly in front of the antenna portion. The low profile of the distal portion of the tool, i.e., the portion with the centering template 422 and the cutter 424, allows the distal portion to be inserted under the skin by way of a relatively small incision. The ramp 430 facilitates sliding of the centering template 422 under the antenna portion of the cochlear implant. The tool 460 can be moved toward the cochlear implant until the antenna portion is in contact with the curved surfaces 434', thereby centering the blade 438 relative to the magnet. The lever 470 may then be used to drive the cutter 424 downwardly until the circular edge 442 passes completely through the antenna portion (between the magnet and the antenna) and the circular edge engages the surface of the relief 436. In some instances, this will be about 6 mm of travel. The mechanical advantage associated with the gear-based actuator 462 allows the user to drive the blade 438 through the housing with less than the 20-30 lbs. that would otherwise be required. The severed portion of the housing (in which the magnet is located) will be wedged into the tapered portion 440 in the manner described above with reference to FIG. 130A. Moving the lever 470 in the opposite direction will mover the cutter to the rest position (FIGS. 137 and 139), thereby pulling the severed portion (and magnet) out of the partial housing.

It should also be noted that the cutter 424 in the exemplary tool 460 moves vertically, i.e. perpendicular to the template base and the bottom surface of the housing antenna portion, which results in a precisely formed aperture 50. The vertical movement also reduces the likelihood of antenna damage.

Another tool that may be used to remove a portion of a cochlear implant housing is the coring and removal tool 486 illustrated in FIGS. 142-148. The tool 486 includes a centering template **422*a*, a cutter 424*a* that is movable relative to the centering template, and an actuator 488 that may be used to drive the cutter through a cochlear implant antenna portion that is located on the centering template. The centering template 422*a* includes a base 428*a*, an abutment 432 with a curved surface 434, and a relief 436 for the cutter 424*a*. The centering template 422*a* also includes a cutter guide 490 with an aperture 492. The exemplary cutter 424*a* includes a blade 438 that has a tapered portion 440 and a continuous sharp circular edge 442 (note FIGS. 144-145**).

The exemplary actuator 488 includes a rotatable cam 494, with a cylindrical member 496 and diagonal slots 498, follower pins 500 that extend outwardly from the cutter **424*a*, and a pin guide 502, with a base 504 and vertically extending members 506 with vertical slots 508 (i.e., slots that extend in the direction of cutter movement). The cutter 424*a* is located within the rotatable cam 494, and the follower pins 500 extend through the diagonal cam slots 498 and into the vertical guide slots 508, as shown in FIGS. 146-147. The vertically extending members 506 of the pin guide 502 are secured to the cutter guide 490. As a result, the follower pins 500 will not rotate with the cam 494 and, instead, will move upwardly or downwardly in the diagonal slots 498 in response to rotational movement of the cam relative to the centering template 422*a* and pin guide 502. The length of the diagonal slots 498 may be such that the cutter 424*a* will be in the fully retracted position when the pins 500 are at the top end of the slots (FIGS. 142 and 146) and the cutter 424*a* will be in the fully extended position, with the blade 438 in contact with the surface of the relief 436, when the pins 500 are at the bottom end of the slots. The cutter 424*a* is shown in a partially extended position in FIG. 148**.

In the illustrated embodiment, the relative rotational movement is facilitated by a lever 510, which is secured to the cam 494, and a lever 512, which is secured to the centering template **422*a*. The lever 510 may be moved towards and away from the lever 512 to move the cutter down and up, while the lever 512 is held still so that the centering template 422*a*** does not move relative to the associated cochlear implant.

The exemplary coring and removal tool 486 illustrated in FIGS. 142-148 may be used to, for example, create the partial housing 12' (FIGS. 5 and 6) that includes the modified antenna portion 26' with the aperture 50. Access to the cochlear implant may, in at least some instances, be obtained by way of an incision that is in front of the antenna portion and offset up to +/−30 degrees from directly in front of the antenna portion. The distal portion of the tool, i.e., the portion with the centering template **422*a* and the cutter 424*a*, can be inserted under the skin by way of the incision until the centering template is under the antenna portion of the cochlear implant and the antenna portion is in contact with the curved surface 434. Such positioning will center the blade 438 relative to the magnet. The lever 510 may then be used to drive the cutter 424*a* downwardly until the circular edge 442 passes completely through the antenna portion (between the magnet and the antenna) and the circular edge engages the surface of the relief 436. In some instances, this will be about 6 mm of travel. The mechanical advantage associated with the cam/follower actuator 488 allows the user to drive the blade 438 through the housing with less than the 20-30 lbs. that would otherwise be required. The severed portion of the housing (in which the magnet is located) will be wedged into the tapered portion 440 in the manner described above with reference to FIG. 130A. Moving the lever 510 in the opposite direction will mover the cutter to the retracted position (FIG. 142**), thereby pulling the severed portion (and magnet) out of the partial housing.

It should also be noted that the cutter 424*a* in the exemplary tool 486 moves vertically, i.e. perpendicular to the template base and the bottom surface of the housing antenna portion, which results in a precisely formed aperture 50. The vertical movement also reduces the likelihood of antenna damage.

One example of a tool that may be used to remove the magnet and a portion of a cochlear implant housing is the coring and removal tool 514 illustrated in FIGS. 149-151. The exemplary coring and removal tool 514 includes the centering template 392 and cutter 394 that are described above with reference to FIGS. 124-132, as well as a screw-punch actuator 516 on which the cutter is fixedly mounted. The screw-punch actuator 516 will rotate the cutter 394 as the cutter is pushed through the centering template 392 and cochlear implant antenna portion.

The exemplary screw-punch actuator 516 includes a handle 518 and a shaft 520 that is both rotatable and longitudinally movable relative to the handle. In particular, the shaft 518 includes a pair of spiral grooves 522 and the handle includes a pair of fixed protuberances 524 that are respectively located in one of the grooves. The protuberances 524 are carried on the inner surface of a collar 526 whose rotation is prevented by the illustrated slot 528 and tab 530 arrangement in the illustrated implementation. When the handle 518 is pushed downwardly, and the cutter 394 is on an object that offers some resistance (e.g., a cochlear implant housing), the shaft 520 will move into the handle and, due to the presence of the spiral grooves 522 and protuberances 524, the shaft will rotate. The cutter 394 will rotate with the shaft 520 until the shaft is fully inserted into the handle 518, as shown in FIG. 151. Rotation of cutter 394 reduces the amount of force necessary to cut through an object (as compared to an identical cutter that is not rotating). The amount of force necessary to drive the shaft 520 into the handle 518, i.e., the amount of force that will be applied to the cut object until the actuator reaches the state illustrated in FIG. 151, is controlled by a spring 530 that is located in a lumen 532 within the handle.

Turning to FIG. 152, the exemplary coring and removal tool 514 may be used to, for example, create the partial housing 12' (FIGS. 5 and 6) that includes the modified antenna portion 26' with the aperture 50. Access to the cochlear implant may, in at least some instances, be provided by an incision that is directly over the antenna portion (including directly over the magnet). After the centering template 392 has been positioned on top of the housing antenna portion 26 and the curved surface of the abutment 404 has been pressed against the end of the antenna portion, thereby centering the template aperture relative to the magnet, the tubular member 408 of the cutter 394 may be inserted into the template guide and through the template aperture. The blade 410 (FIG. 150), which is also centered relative to the magnet, may then be pushed through the antenna portion 12 (between the magnet and the antenna) by applying axial force F to the handle 518. The shaft 520 and cutter 394 will rotate (note arrow R) as the shaft moves into handle 518 and the cutter moves through the housing material. The magnitude of the axial force F is controlled by the spring 530. The axial force F may be applied until the circular edge 418 of the cutter blade passes through the bottom wall 48. As described above with reference to FIG. 130A, the severed portion of the housing (in which the magnet is located) will be wedged into the tapered portion 416 of the blade 410 and can be easily removed.

It should also be noted here that the present methods of removing portions of cochlear implant housings are not limited to the tools described above. For example, lasers may be used to ablate portions of a cochlear implant housing to facilitate removal of a portion thereof, such as the severed portion 29 (FIG. 107). Here, the stencil 300 (FIG. 104) may be used as guide and to ensure that the antenna is not damaged by the laser.

Turning to FIG. 153, one example of a system (or "kit") 80 in accordance with at least one of the present inventions includes a magnet apparatus insert with a MRI-compatible magnet apparatus, such as one of the magnet apparatus inserts 60*a* (shown) or 60*b*-60*h* and 60*j*, as well as a tool that facilitates removal of a portion of a cochlear implant housing, such as the stencil 300 (shown), the cutting tool positioner 320, center punch 340 or the one of the coring and removal tools 390, 420, 460, 486 and 514. Other kits may include the coring tool 360 and the MRI-compatible magnet apparatus 200. Still other kits may include a tool that facilitates removal of a portion of a cochlear implant housing, such as the stencil 300 (shown), the cutting tool positioner 320, center punch 340, or the one of the coring and removal tools 390, 420, 460, 486 and 514, in combination with MRI-compatible magnet apparatus such as any of magnet apparatuses 200*b*-200*p*. Some kits may also include one or more bone screws or other bone anchors and/or a screwdriver or other tool that may be used to drive the bone anchor into bone. The components of the kit 80 may be housed in a sterile package 82 that has a flat rigid bottom portion 84 and a top transparent top cover 86, thereby providing a ready to use surgical kit. The bottom portion 84 may be formed from a material which allows the contents of the package to be sterilized after being sealed within the package.

The present inventions have application in a wide variety of systems including, but not limited to, those that provide sound (i.e., either sound or a perception of sound) to the hearing impaired. One example of such a system is an ICS system where an external sound processor communicates with a cochlear implant. Turning to FIG. 154, the exemplary cochlear implant system 90 includes the above-described modified cochlear implant 10*a*, a sound processor, such as the illustrated body worn sound processor 700 or a behind-the-ear sound processor, and a headpiece 800.

As noted above, the exemplary modified cochlear implant 10*a* includes a modified flexible housing 12', a processor assembly 14, a cochlear lead 16 with an electrode array, an antenna 18, and an MRI-compatible magnet apparatus 200.

The exemplary body worn sound processor 700 includes a housing 702 in which and/or on which various components are supported. Such components may include, but are not limited to, sound processor circuitry 704, a headpiece port 706, an auxiliary device port 708 for an auxiliary device such as a mobile phone or a music player, a control panel 710, one or more microphones 712, and a power supply receptacle 714 for a removable battery or other removable power supply 716 (e.g., rechargeable and disposable batteries or other electrochemical cells). The sound processor circuitry 704 converts electrical signals from the microphone 712 into stimulation data. The exemplary headpiece 800 includes a housing 802 and various components, e.g., a RF connector 804, a microphone 806, an antenna (or other transmitter) 808 and a disk-shaped positioning magnet 810, that are carried by the housing. The headpiece 800 may be connected to the sound processor headpiece port 706 by a cable 812. The positioning magnet 810 is attracted to the magnet apparatus 200 of the cochlear stimulator 10*a*, thereby aligning the antenna 808 with the antenna 18.

The stimulation data and, in many instances power, is supplied to the headpiece 800. The headpiece 800 transcutaneously transmits the stimulation data, and in many instances power, to the cochlear implant 10*a* by way of a wireless link between the antennas. The stimulation processor 38 (FIG. 1) converts the stimulation data into stimulation signals that stimulate the electrodes of the electrode array on the cochlear lead 16.

In at least some implementations, the cable 812 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 712 on the sound processor 700, the microphone 806 may be also be omitted in some instances. The functionality of the sound processor 700 and headpiece 800 may also be combined into a single head wearable sound processor. Examples of head wearable sound processors are illustrated and described in U.S. Pat. Nos. 8,811,643 and 8,983,102, which are incorporated herein by reference in their entirety.

Although the inventions disclosed herein have been described in terms of the preferred embodiments above, numerous modifications and/or additions to the above-described preferred embodiments would be readily apparent to one skilled in the art. By way of example, but not limitation, the present inventions may be used to simply replace the magnet within a cochlear implant with a larger magnet (as opposed to a larger MRI-compatible magnet apparatus). The present inventions include any combination of the elements from the various species and embodiments disclosed in the specification that are not already described. It is intended that the scope of the present inventions extend to all such modifications and/or additions and that the scope of the present inventions is limited solely by the claims set forth below.

I claim:

1. A magnet apparatus for use with an implantable medical device, the magnet apparatus comprising:

a case including a top surface, a bottom surface and a cylindrical side surface located between the top surface and the bottom surface;

a projection, located between the top surface and the bottom surface, that projects outwardly from the cylindrical side surface and is configured to interconnect with a portion of the implantable medical device;

at least one magnetic element within the case that is rotatable relative to the case;

a stiff strap, secured to the case, that includes an anchor aperture; and a bone anchor configured to extend through the anchor aperture of the stiff strap and anchor the case to bone.

2. The magnet apparatus claimed in claim 1, wherein the bone anchor comprises a bone screw.

3. The magnet apparatus claimed in claim 1, wherein the case includes a top; and the stiff strap is secured to the top of the case.

4. The magnet apparatus claimed in claim 1, wherein the case includes a bottom; and the stiff strap is secured to the bottom of the case.

5. The magnet apparatus claimed in claim 1, wherein the projection is configured to mechanically interconnect the case to a portion of the implantable medical device.

6. The magnet apparatus claimed in claim 5, wherein the projection has a semi-circular shape.

7. The magnet apparatus claimed in claim 5, wherein the projection is not sharp.

8. The magnet apparatus claimed in claim 5, wherein the case is disk-shaped and defines a perimeter; and the projection extends completely around the perimeter.

9. The magnet apparatus claimed in claim 1, wherein the case defines a central axis;

a magnet frame is located within the case and rotatable relative to the case about the central axis; and the at least one magnetic element comprises a plurality of elongate diametrically magnetized magnets that are located in the magnet frame, the magnets defining a longitudinal axis and a N-S direction and being freely rotatable about the longitudinal axis relative to the magnet frame.

10. The magnet apparatus claimed in claim 9, wherein the magnets each define a N-S rotational orientation; and the magnets are magnetically attracted to one another in such manner that, absent the presence of a dominant magnetic field, the N-S rotational orientation of the magnets is perpendicular to the central axis of the case.

11. The magnet apparatus claimed in claim 1, wherein at least one magnetic element comprises a plurality of magnetic material particles that are moveable relative to the case and to one another.

12. The magnet apparatus claimed in claim 1, wherein at least one magnetic element comprises a diametrically magnetized disk-shaped magnet.

13. A cochlear implant, comprising:

a cochlear implant housing, formed from a resilient elastomer, including an antenna portion and an aperture within the antenna portion that extends through the cochlear implant housing;

a cochlear lead;

an antenna within the antenna portion;

a stimulation processor within the cochlear implant housing operably connected to the antenna and to the cochlear lead; and a magnet apparatus as claimed in claim 1 at least partially within the cylindrical aperture.

* * * * *